United States Patent
Carroll et al.

(10) Patent No.: US 12,054,474 B2
(45) Date of Patent: *Aug. 6, 2024

(54) SULFONYL PIPERIDINE DERIVATIVES AND THEIR USE FOR TREATING PROKINETICIN MEDIATED DISEASES

(71) Applicant: Takeda Pharmaceutical Company Limited, Osaka (JP)

(72) Inventors: Colm Carroll, Brussels (BE); Anne Goldby, Cambridgeshire (GB); Martin Teall, Cambridgeshire (GB)

(73) Assignee: Takeda Pharmaceutical Company Limited (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/962,781

(22) Filed: Oct. 10, 2022

(65) Prior Publication Data

US 2023/0073334 A1  Mar. 9, 2023

Related U.S. Application Data

(60) Continuation of application No. 16/707,079, filed on Dec. 9, 2019, now Pat. No. 11,512,066, which is a continuation of application No. 16/194,762, filed on Nov. 19, 2018, now Pat. No. 10,544,126, which is a division of application No. 15/262,436, filed on Sep. 12, 2016, now Pat. No. 10,167,273, which is a continuation of application No. 14/402,751, filed as application No. PCT/GB2013/051415 on May 29, 2013, now Pat. No. 9,475,795.

(30) Foreign Application Priority Data

May 30, 2012  (GB) ..................... 1209587

(51) Int. Cl.
| | | |
|---|---|---|
| A61K 31/454 | (2006.01) | |
| A61K 31/4545 | (2006.01) | |
| A61K 45/06 | (2006.01) | |
| C07D 211/96 | (2006.01) | |
| C07D 401/12 | (2006.01) | |
| C07D 401/14 | (2006.01) | |

(52) U.S. Cl.
CPC .......... C07D 401/12 (2013.01); A61K 31/454 (2013.01); A61K 31/4545 (2013.01); A61K 45/06 (2013.01); C07D 211/96 (2013.01); C07D 401/14 (2013.01)

(58) Field of Classification Search
CPC ..................................................... C07D 401/12
See application file for complete search history.

(56) References Cited

U.S. PATENT DOCUMENTS

| | | |
|---|---|---|
| 2005/0256159 A1 | 11/2005 | Barton |
| 2008/0009514 A1 | 1/2008 | Stoit |
| 2013/0324576 A1 | 12/2013 | Carroll et al. |

FOREIGN PATENT DOCUMENTS

| | | |
|---|---|---|
| CA | 2501611 | 4/2004 |
| CA | 2516234 | 9/2004 |
| CA | 2590666 | 7/2006 |
| EP | 1227090 | 7/2002 |
| EP | 1302463 | 4/2003 |
| EP | 1657240 | 5/2006 |
| EP | 1676844 | 7/2006 |
| EP | 2153832 | 2/2010 |
| JP | 2006-506451 | 2/2006 |
| WO | WO 96/06098 | 2/1996 |
| WO | WO 97/23466 | 7/1997 |
| WO | WO 97/30998 | 8/1997 |
| WO | WO 99/03859 | 1/1999 |
| WO | WO 99/05134 | 2/1999 |
| WO | WO 00/42044 | 7/2000 |
| WO | WO 01/29034 | 4/2001 |
| WO | WO 01/36417 | 5/2001 |
| WO | WO 01/60821 | 8/2001 |
| WO | WO 01/62757 | 8/2001 |
| WO | WO 02/08212 | 1/2002 |
| WO | WO 02/094794 | 11/2002 |
| WO | WO 02/096912 | 12/2002 |
| WO | WO 03/087102 | 10/2003 |
| WO | WO 03/087103 | 10/2003 |

(Continued)

OTHER PUBLICATIONS

E.S.W. Ngan, P.K.H. Tam / The International Journal of Biochemistry & Cell Biology 40 (2008) 1679-1684.*

(Continued)

*Primary Examiner* — David K O'Dell

(74) *Attorney, Agent, or Firm* — BARNES & THORNBURG LLP; Scott D. Rothenberger

(57) ABSTRACT

The present invention provides compounds of formula (I) and pharmaceutically acceptable salts thereof.

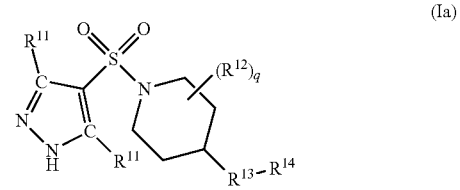

(Ia)

in which q, $R^{11}$, $R^{12}$, $R^{13}$ and $R^{14}$ are as defined in the specification, for use in therapy.

1 Claim, No Drawings

(56) References Cited

FOREIGN PATENT DOCUMENTS

| WO | WO 03/087104 | 10/2003 |
|---|---|---|
| WO | WO 2004/016616 | 2/2004 |
| WO | WO 2004/016617 | 2/2004 |
| WO | WO 2004/019947 | 3/2004 |
| WO | WO 2004/033427 A1 | 4/2004 |
| WO | WO 2004/043929 | 5/2004 |
| WO | WO 2004/074283 A1 | 9/2004 |
| WO | WO 2005/100349 | 10/2005 |
| WO | WO 2007/079163 | 7/2007 |
| WO | WO 2007/079214 | 7/2007 |
| WO | 2008/130718 | 10/2008 |
| WO | WO 2010/077976 | 7/2010 |
| WO | 2010/114909 | 10/2010 |
| WO | WO 2013/179024 | 12/2013 |

OTHER PUBLICATIONS

Negri "Targeting the Prokineticin System to Control Chronic Pain and Inflammation" Current Medicinal Chemistry, 2018, 25, 3883-3894, p. 3885.*
Freye "Opioids in Medicine" A Comprehensive Review on the Mode of Action and the Use of Analgesics in Different Clinical Pain States, Springer:Dordrecht, 2008.*
Lee "Comparison of complex regional pain syndrome and fibromyalgia" Medicine (2019) 98:7.*
International Search Report and Written Opinion from related International Application PCT/GB2013/051415, dated Jul. 4, 2013, 17 pages.
International Preliminary Report on Patentability from related International Application PCT/GB2013/051415, dated Dec. 2, 2014, 14 pages.
Lizarzaburu, et al., "Convenient preparation of aryl ether derivatives using a sequence of functionalized polymers", Tetrahedron Letters, No. 44, 2003, pp. 4873-4876.
Medhurst, et al., "GSK189254, a novel H3 receptor antagonist that binds to histamine H3 receptors in Alzheimer's disease brain and improves cognitive performance in preclinical models", Journal of Pharmacology and Experimental Therapeutics, No. 321, 2007, p. 1032.
Orjales, et al., "Syntheses and binding studies of new [(aryl)(aryloxy)methyl]piperidine derivatives and related compounds as potential antidepressant drugs with high affinity for serotonin (5-HT) and norepinephrine (NE) transporters" J. Med. Chem., No. 46, 2003, pp. 5512-5532.
Tu, et al., "Synthesis and in vitro and in vivo evaluation of 18F-labeled positron emission tomography (PET) ligands for imaging the vesicular acetylcholine transporter", J. Med. Chem., No. 52, 2009, pp. 1358-1369.
Online http:/web.archive.org/web/20070630171813/http://www.enamine.net/index.php?option=comconent&task=view&id=22 &menuid=51&PHPSESSID=64a4f248f69d671a413f487bb62c4d90 dated Jun. 30, 2007, accessed Apr. 1, 2015.
Online http:/web.archive.org/web/20130122020518/http://www.chembridge.com/screening_libraries/ 2011, accessed Dec. 15, 2015.
STN-Chemical database registry # RN 1378011-79-0, CN 4-(2-fluoro-5-methylphenoxy)-1-[(1-methyl-1H-pyrazol-4-yl)sulfonyl]-4-Piperidinecarboxylic acid, ED Entered STN: Jun. 13, 2012.
STN-Chemical database registry # RN 1445603-90-6, 1-[(1,2-dimethyl-1H-imidazol-4-y)sulfonyl]-alpha.-phenyl-4-Piperidinemethanol, Entered STN: Jun. 18, 2013.
Database Registry, Chemical Abstracts Service, Columbus, OH, US; Sep. 20, 2013, XP002734305, Database accession No. 1452884-03-5 rn 1452884-03-5, SciFinder®, 1 page.
Database Registry, Chemical Abstracts Service, Columbus, OH, US: Sep. 22, 2013, XP002734306, Database accession No. 1452939-05-7 rn 1452939-05-7, SciFider®, 1 page.
Database Registry, Chemical Abstracts Service, Columbus, OH, US: Sep. 22, 2013, XP002734307, Database accession No. 1452992-07-2 rn 1452992-07-2, SciFinder®, 1 page.
Database Registry, Chemical Abstracts Service, Columbus, OH UF: Sep. 22, 2013, XP002734308, Database accession No. 1453017-19-0 rn 1452017-189-0, SciFinder®, 1 page.
FDA Guidelines for drug interaction studies, Federal Register, Notices vol. 71, No. 176, Tuesday, Sep. 12, 2006, 53696-53697.
International Search Report from related International Application PCT/GB2014/051900, dated Jul. 24, 2014.
International Search Report and Written Opinion from related International Application PCT/GB2014/052428, dated Oct. 2, 2014, 6 pages.
International Search Report and Written Opinion from related International Application PCT/GB2014/053499, dated Jan. 27, 2015, 13 pages.
Kovalskiy et al, Synthesis of 3-(3-piperidyl)-isoquinoline and 3-(4-piperidyl)-isoquinoline, Chemistry of Heterocyclic Compounds, VI. 45, No. 8, Nov. 20, 2009, pp. 957-964.
National Center for Biotechnology Information, PubChem Compound database: CID=5204150, https://pubchem.mcbi.nim.nih.gov/compound/5204150, available Oct. 7, 2005, 10 pages.
Office Action from related Application U.S. Appl. No. 13/904,198, dated Aug. 28, 2015, 18 pages.
OECD Guidelines for testing of chemicals: 432 In Vitro 3T3 Neutral Red Uptake phototoxicity test, Apr. 2004, 15 pages.
Amendment and Response to Office Action from related application U.S. Appl. No. 13/904,198, dated Aug. 28, 2015, 17 pages.
Trujillo, et al. "Novel Tetrahydro-beta-carboline-1-carboxylic acids as inhibitors of mitogen activated protein kinase-activated protein kinase 2 (KD-2)", Bioorganic & Medicinal Chemistry Letters, vol. 17, No. 16, Jul. 17, 2007, pp. 4657-4663.
Civelli, Q.-Y. Zhou in Orphan G Protein-Coupled Receptors and Novel Neuropeptides, Springer-Veriag: Berlin Heidelberg, 2008, 181-199.
Hook V. Y. H. "Neuroproteases in Peptide Neurotrnasmission and Neurodegenerative Diseases Applications to Drug Discovery Research", Biodrugs 2006, 20, 105-119.
Eric R. Marcotte J "Animal models of schizophrenia: a critical review" Psychiatry Neuroscience 2001; 26(5):395-410.
Negri "Bv8/PK2 and prokineticin receptors: a druggable pronociceptive system" Current Opinion in Pharmacology 2012, 12:62-66.
Quock et al., "The delta-Opiod receptor: Molecular Pharamacology, Signal Transduction, and the Determination of Drug Efficacy" Pharmacological Reviews 1999, 51(3), 503-532.
Le Bars, et al, "Animal Models of Nociception" Pharmacological Reviews 2001, 53, 597-652.
Exam report for EP application No. EP13728238.0 dated Dec. 23, 2015.
Exam report for EP application No. EP13728238.0 dated Aug. 11, 2016.
Restriction requirement for U.S. Appl. No. 13/904,198 dated Mar. 20, 2015.
Office action for U.S. Appl. No. 13/904,198 dated Feb. 11, 2016.
Restriction requirement for U.S. Appl. No. 14/402,751 dated Mar. 6, 2015.
Office action for U.S. Appl. No. 14/402,751 dated Jun. 9, 2015.
Office action for U.S. Appl. No. 14/402,751 dated Dec. 21, 2015.
Office action for U.S. Appl. No. 14/402,751 dated Apr. 19, 2016.
Restriction requirement for U.S. Appl. No. 15/262,436 dated Apr. 5, 2017.
Office action for U.S. Appl. No. 15/262,436 dated Aug. 11, 2017.
Office action for U.S. Appl. No. 15/262,436 dated Jan. 3, 2018.
Chemical Abstract Registry No. 1006322-80-0; Entered STN: Mar. 3, 2008; Piperidine, 1-[(1-(difluoromethyl)-5-methyl-1H-pyrazol-4-yl]sulfonyl]-4-(phenylmethyl).
Chemical Abstract Registry No. 902869-85-6; Entered STN: Aug. 21, 2006; 1H-Pyrrole-2-carboxylic acid, 1-methyl-4-[[4-(phenylmethyl)-1-piperidinyl]sulfonyl]-, methyl ester.
Response to Restriction Requirement dated Mar. 20, 2015, for US Appl. No. 13/904,198, filed Apr. 23, 2015.
Response to Restriction Requirement dated Mar. 6, 2016, for U.S. Appl. No. 14/402,751, filed Apr. 23, 2015.
Response to Office Action dated Jun. 9, 2015, for U.S. Appl. No. 14/402,751, filed Nov. 6, 2015.

(56) References Cited

OTHER PUBLICATIONS

Response to Office Action mailed Dec. 21, 2015, for U.S. Appl. No. 14/402,751, filed Mar. 21, 2016.
Response to Office Action mailed Apr. 19, 2016 for U.S. Appl. No. 14/402,751, filed May 26, 2016.
Response to Restriction Requirement mailed Apr. 5, 2017, for U.S. Appl. No. 15/262,436, filed Jul. 5, 2017.
Response to Office Action mailed Aug. 11, 2017, for U.S. Appl. No. 15/262,436, filed Nov. 13, 2017.
Response to Office Action mailed Jan. 3, 2018, for U.S. Appl. No. 15/262,436, filed May 1, 2018.
Response to Exam Report for EP application No. EP13728238.0 dated Dec. 23, 2015, filed Mar. 1, 2016.
Response to Exam Report for EP application No. EP13728238.0 dated Aug. 11, 2016, filed Dec. 15, 2016.
Amendment and Response to Office Action dated Sep. 28, 2021, filed Feb. 3, 2022 for U.S. Appl. No. 16/707,079.
Office Action issued Sep. 28, 2021 for U.S. Appl. No. 16/707,079, filed Dec. 9, 2019.
Amendment and Response to Office Action Made Final dated Nov. 23, 2020 and Advisory Action dated Mar. 10, 2021 for U.S. Appl. No. 16/707,079, filed Dec. 19, 2019.
Advisory Action issued Mar. 10, 2021 for U.S. Appl. No. 16/707,079, filed Dec. 9, 2019.
Amendment and Response to Office Action Made Final dated Nov. 23, 2020, for U.S. Appl. No. 16/77,079.
Office Action issued Nov. 23, 2020 for U.S. Appl. No. 16/707,079, filed Dec. 9, 2019.
Amendment and Response to Office Action dated Apr. 23, 2020 for U.S. Appl. No. 16/707,079.
Office Action issued Apr. 23, 2020 for U.S. Appl. No. 16/707,079, filed Dec. 9, 2019.
Chemical Abstract Registry No. 1333813-97-0; Entered STN: Sep. 29, 2011; Piperidine, 4-[(2-fluorophenyl) methyl]-1-[(1-methyl-1H-pyrazol-4-yl) sulfonyl].
Chemical Abstract Registry No. 1323224-43-6; Entered STN; Aug. 25, 2011; Methanone, [1-[(3,5-dimethyl-1H-pyrazol-4-yl) sulfonyl]-4-piperidyinyl] (4-methylphenyl).
Chemical Abstract Registry No. 1323220-07-0; Entered STN: Aug. 25, 2011; Methanone, (2,4-dimethylphenyl) [1-[(3,5-dimethyl-1H-pyrazol-4-yl) sulfonyl]-4-piperidinyl).
Chemical Abstract Registry No. 1323220-00-3; Entered STN: Aug. 25, 2011; Methanone, [1-[(3,5-dimethyl-1H-pyrazol-4-yl) sulfonyl]-4-piperidinyl] (4-fluoro-3-methylphenyl).
Chemical Abstract Registry No. 1323216-70-1; Entered STN: Aug. 25, 2011; Methanone, [1-[(3,5-dimethyl-1H-pyrazol-4-yl) sulfonyl)-4-piperidinyl]phenyl.
Chemical Abstract Registry No. 1323215-12-8; Entered STN: Aug. 25, 2011; Methanone, (4-chlorphenyl)([1-[(3,5-dimethyl-1H-pyrazol-4-yl) sulfonyl]-4-piperidinyl].
Chemical Abstract Registry No. 1323212-97-0; Entered STN Aug. 25, 2011; Methanone, [1-[(3,5-dimethyl-1H-pyrazol-4-yl) sulfonyl)-4-piperidinyl] (4-fluorophenyl).
Chemical Abstract Registry No. 1323135-27-8; Entered STN: Aug. 25, 2011; Piperidine, 1-[(3,5-dimethyl-1H-pyrazol-4-yl) sulfonyl)-4-(4-methoxyphenoxy).
Chemical Abstract Registry No. 1323135-26-7; Entered STN: Aug. 25, 2011; Piperidine, 1-[(3,5-dimethyl-1H-pyrazol-4-yl) sulfonyl]-4-(4-phenoxy).
Chemical Abstract Registry No. 1323128-78-4; Entered STN: Aug. 25, 2011; Methanone, [1-[(3,5-dimethyl-1H-pyrazol 4-yl) sulfonyl)-4-piperidinyl] (4-methoxyphenyl).
Chemical Abstract Registry No. 1323128-17-1; Entered STN: Aug. 25, 2011; Methanone, [3,4-dimethylphenyl) [1-[(3,5-dimethyl-1H-pyrazol-4-yl) sulfonyl)-4-piperidinyl].
Chemical Abstract Registry No. 1323126-76-6; Entered STN: Aug. 25, 2011; Piperidine, [1-[(3,5-dimethyl-1H-pyrazol-4-yl) sulfonyl]-4-(methoxyphenylmethyl).
Chemical Abstract Registry No. 1323099-36-0; Entered STN: Aug. 25, 2011; Piperidine, [1-[(3,5-dimethyl-1H-pyrazol-4-yl) sulfonyl]-4-(3-ethylphenoxy).
Chemical Abstract Registry No. 1311701-67-3; Entered STN: Jul. 7, 2011; Piperidine, 4-[4-fluorphenyl) methyl]-1-(1-methyl-1H-pyrazol-4-yl) sulfonyl].
Chemical Abstract Registry No. 1311596-41-4; Entered STN: Jul. 7, 2011; 4-Piperidinamine, N-(4-methylphenyl)-1-[(1-methyl-1H-pyrazol-4-yl) sulfonyl].
Chemical Abstract Registry No. 1295533-32-2; Entered STN: May 16, 2011; Methanone, [1-[(5-chloro-1-methyl-1H-midazol-4-yl)sulfonyl]-4-piperidinyl]phenyl.
Chemical Abstract Registry No. 1295151-61-9; Entered STN: May 15, 2011; Methanone, phenyl [1-[1,3,5-trimethyl-1H-pyrazol-4-yl)sulfonyl]-4-piperidinyl].
Chemical Abstract Registry No. 1279467-77-4; Entered STN: Apr. 13, 2011; Methanone, [1-[(5-chloro-1-methyl-1H-midazol-4-yl) sulfonyl]-4-piperidinyl](4-methoxyphenyl).
Chemical Abstract Registry No. 1278419-32-1; Entered STN: Apr. 11, 2011; Methanone, [2,5-difluorophenyl) [1-[(1-methyl-1H-pyrazol-4-yl)sulfonyl)-4-piperidinyl).
Chemical Abstract Registry No. 1277904-25-2; Entered STN: Apr. 10, 2011; Methanone, [1-[(5-chloro-1,3-dimethyl-1H-pyrazol-4-yl)sulfonyl]-4-piperidinyl)phenyl.
Chemical Abstract Registry No. 1257654-94-6; Entered STN: Dec. 28, 2010; Piperidine, 1-[(3,5-dimethyl-1H-pyrazol-4-yl)sulfonyl]-4-[(4-flurophenyl)methyl].
Chemical Abstract Registry No. 1239969-98-2; Entered STN: Sep. 3, 2010; Piperidine, 4-[(3,4-dimethoxyphenyl) methyl]-1-[(3,5-dimethyl-1H-pyrazol-4-yl)sulfonyl].
Chemical Abstract Registry No. 1178477-87-6; Entered STN: Aug. 31, 2009; Piperidine, 4-(phenylmethyl)-1-(1H-pyrazol-4-yl-sulfonyl).
Chemical Abstract Registry No. 1172497-37-8; Entered STN; Aug. 4, 2009; Piperidine, 1-[(3-(1,1-dimethylethyl)-1-(1-methylethyl)-1H-pyrazol-4-yl]sulfonyl-4-(phenylmethyl).
Chemical Abstract Registry No. 1172397-77-1; Entered STN: Aug. 4, 2009; Piperidine, 1-[(3-methyl-1-(1-methylethyl)-1H-pyrazol-4-yl)sulfonyl]-4-(phenylmethyl).
Chemical Abstract Registry No. 1171347-09-3; Entered STN: Aug. 2, 2009; Piperidine, 1-[(3-(1,1-dimethylethyl)-1-methyl-1H-pyrazol-4-yl]sulfonyl]-4-(phenylmethyl).
Chemical Abstract Registry No. 1039046-34-8; Entered STN: Aug. 6, 2008; Piperidine, 1-[(3,5-dimethyl-1H-pyrazol-4-yl)sulfonyl]-4-(phenylmethyl).
Chemical Abstract Registry No. 1006331-86-7; Entered STN: Mar. 3, 2008; Piperidine, 1-[(1-difluromethyl)-1H-pyrazol-4-yl)sulfonyl]-4-(phenylmethyl).
Chemical Abstract Registry No. 1006322-04-8; Entered STN: Mar. 3, 2008; Piperidine, 1-[(1-methyl-1H-pyrazol-4-yl) sulfonyl]-4-(phenylmethyl).
Chemical Abstract Registry No. 932300-77-1; Entered STN: Apr. 24, 2007; Piperidine, 1-[(1-methyl-1H-imidazol-4-yl) sulfonyl]-4-(phenylmethyl).
Chemical Abstract Registry No. 897449-22-8; Entered STN: Jul. 31, 2006; Piperidine, 1-[(1-ethyl-1H-pyrazol-4-yl) sulfonyl]-4-(phenylmethyl).
Chemical Abstract Registry No. 897449-21-7; Entered STN: Jul. 31, 2006; Piperidine, 1-[(1-ethyl-5-methyl-1H-pyrazol-4-yl)sulfonyl]-4-(phenylmethyl).
Chemical Abstract Registry No. 897449-19-3; Entered STN: Jul. 31, 2006; Piperidine, 1-[(1, 5-dimethyl-1H-pyrazol-4-yl) sulfonyl]-4-(phenylmethyl).
Chemical Abstract Registry No. 897449-16-0; Entered STN Jul. 31, 2006; Piperidine, 1-[(1-ethyl-3-methyl-1H-pyrazol-4-yl)sulfonyl]-4-(phenylmethyl).
Chemical Abstract Registry No. 588713-26-2; Entered STN Sep. 19, 2003; Piperidine, 1-[(1,3-dimethyl-1H-pyrazol-4-yl) sulfonyl-4-(phenylmethyl).
Chemical Abstract Registry No. 1340862-71-6; Entered STN: Nov. 4, 2011;2-Pyrazinamine, N-[1-(1H-imidazol-5-ylsulfonyl)-4-piperidinyl]-3-methoxy.

(56) References Cited

OTHER PUBLICATIONS

Chemical Abstract Registry No. 1340845-67-1; Entered STN: Nov. 4, 2011; 2-Pyrazinamine, 3-methoxy-N-[1-[(1-methyl-1H-imidazol-4-yl)sulfonyl]-4-piperidinyl].
Chemical Abstract Registry No. 1323239-42-4; Entered STN: Aug. 25, 2011; Methanone, [1-[(3,5-dimethyl-1H-pyrazol-4-yl)sulfonyl]-4-piperidinyl]-1H-indol-3-yl.
Chemical Abstract Registry No. 1323227-50-4; Entered STN: Aug. 25, 2011; Piperidine, 1-[(3,5-dimethyl-1H-pyrazol-4-yl)sulfonyl]-4-(4-methylphenoxy).
Chemical Abstract Registry No. 1323227-49-1; Entered STN: Aug. 25, 2011; Piperidine, 1-[(3,5-dimethyl-1H-pyrazol-4-yl)sulfonyl]-4-(4-fluorophenoxy).
Chemical Abstract Registry No. 1323216-62-1; Entered STN : Aug. 25, 2011; Methanone, [1-[(3,5-dimethyl-1H-pyrazol-4-yl)sulfonyl]-4-piperidinyl]-2-thienyl.
Chemical Abstract Registry No. 1323117-02-7; Entered STN: Aug. 25, 2011; Methanone, (2,5-dimethylphenyl)[1-[(3,5,-dimethyl-1H-pyrazol-4-yl)sulfonyl]-4-piperidinyl].
Chemical Abstract Registry No. 1322731-93-0; Entered STN: Aug. 24, 2011; 1H-Pyrazole-4-carboxylic acid, 3-ethyl-5-[[4-(phenylmethyl)-1-piperidinyl]sulfonyl]-, methyl ester.
Chemical Abstract Registry No. 1321169-17-8; Entered STN: Aug. 21, 2011; 1H-indole-5-carboxylic acid, 1-[[1-[(1,2-dimethyl-1H-imidazol-4-yl)sulfonyl]-4-piperidinyl]carbonyl]-2,3-dihydro-, methyl ester.
Chemical Abstract Registry No. 1319209-07-8; Entered STN: Aug. 17, 2011; Methanone, (2,3-dihydro-1H-indol-1-yl)[1-[(3,5-dimethyl-1H-pyrazol-4-yl)sulfonyl]-4-piperidinyl].
Chemical Abstract Registry No. 1304090-43-4; Entered STN Jun. 1, 2011; Piperidine, 4-phenoxy-1-(1H-pyrazol-4-ylsulfonyl).
Chemical Abstract Registry No. 1296530-04-5; Entered STN: May 18, 2011; Methanone, (6,7-difluoro-3,4-dihydro-1(2H)-quinolinyl)[1-[(1,2-dimethyl-1H-imidazol-4-yl)sulfonyl]-4-piperidinyl].
Chemical Abstract Registry No. 1296311-49-3; Entered STN: May 18, 2011; Piperidine, 4-(3-chlorophenoxy)-1-[(3,5-dimethyl-1H-pyrazol-4-yl)sulfonyl].
Chemical Abstract Registry No. 1294643-21-2; Entered STN: May 15, 2011; Methanone, [1-[(5-chloro-1,3-dimethyl-1H-pyrazol-4-yl)sulfonyl]-4-piperidinyl](4-methoxyphenyl).
Chemical Abstract Registry No. 1287971-72-5; Entered STN: May 1, 2011; Methanone, (6-bromo-3,4-dihydro-1(2H)-quinolinyl)[1-[(1,2-dimethyl-1H-imidazol-4-yl)sulfonyl]-4-piperidinyl].
Chemical Abstract Registry No. 1287425-89-1; Entered STN; Apr. 29, 2011; Piperidine, 1-[(3,5-dimethyl-1H-pyrazol-4-yl)sulfonyl]-4-(2-methylphenoxy).
Chemical Abstract Registry No. 1287425-22-2; Entered STN; Apr. 29, 2011; Pyrazine, 2-[[1-[(3,5-dimethyl-1H-pyrazol-4-yl)sulfonyl]-4-piperidinyl]oxy].
Chemical Abstract Registry No. 1281006-56-1; Entered STN: Apr. 17, 2011; Benzonitrile, 4-[[1-[(1-methyl-1H-pyrazol-4-yl)sulfonyl]-4-piperidinyl]oxy].
Chemical Abstract Registry No. 1268995-59-0; Entered STN: Mar. 21, 2011; 3H-1,2,4-Triazol-3-one, 5-[[1-[(1,3-dimethyl-1H-pyrazol-4-yl)sulfonyl]-4-piperidinyl]methyl]-4-ethyl-2,4-dihydro.
Chemical Abstract Registry No. 1257650-64-8; Entered STN: Dec. 28, 2010; 1H-Benzimidazole, 1-[[1-[(3,5-dimethyl-1H-pyrazol-4-yl)sulfonyl]-4-piperidinyl]methyl]-2-methyl.
Chemical Abstract Registry No. 1257150-69-8; Entered STN: Dec. 20, 2010; 4H-1,2,4-Triazole-3-methanol, 5-[[1-[(1-ethyl-1H-pyrazol-4-yl)sulfonyl]-4-piperidinyl]methyl]-4-methyl].
Chemical Abstract Registry No. 1240937-76-1; Entered STN: Sep. 14, 2010; 4-Piperidinamine, N-(2-methylphenyl)-1-[(1,3,5-trimethyl-1H-pyrazol-4-yl)sulfonyl].

Chemical Abstract Registry No. 1239154-09-6; Entered STN: Aug. 26, 2010; Piperidine, 1-[(3,5-dimethyl-1H-pyrazol-4-yl)sulfonyl]-4-(2-thienylmethyl).
Chemical Abstract Registry No. 1214598-32-9; Entered STN: Mar. 25, 2010; Piperidine, 1-[[1-(difluoromethyl)-3-methyl-1H-pyrazol-4-yl]sulfonyl]-4-(4-fluorophenoxy).
Chemical Abstract Registry No. 1214526-09-6; Entered STN; Mar. 25, 2010; Piperidine, 4-(3-fluorophenoxy)-1-[(3-methyl-1-propyl-1H-pyrazol-4-yl)sulfonyl].
Chemical Abstract Registry No. 1214489-16-3; Entered STN: Mar. 25, 2010; Piperidine, 1-[[1-(difluoromethyl)-3,5-dimethyl-1H-pyrazol-4-yl]sulfonyl]-4-(2-fluorophenoxy).
Chemical Abstract Registry No. 1185032-17-0; Entered STN: Sep. 16, 2009; Methanone, (2,3-dihydro-1H-indol-1-yl)[1-[(1-ethyl-1H-imidazol-4-yl)sulfonyl]-4-piperidinyl].
Chemical Abstract Registry No. 1023041-18-0; Entered STN: May 27, 2008; Piperidine, 1-[(5-chloro-1,3-dimethyl-1H-pyrazol-4-yl)sulfonyl]-4-(phyenylmethyl).
Chemical Abstract Registry No. 1006353-31-6; Entered STN: Mar. 3, 2008; Piperidine, 1-[[1-(difluoromethyl)-3-methyl-1H-pyrazol-4-yl]sulfonyl]-4-(phenylmethyl).
Chemical Abstract Registry No. 1006341-60-1; Entered STN: Mar. 3, 2008; Piperidine, 1-[[1-(difluoromethyl)-3,5-dimethyl-1H-pyrazol-4-yl]sulfonyl]-4-(phenylmethyl).
Chemical Abstract Registry No. 1006322-40-2; Entered STN: Mar. 3, 2008; Piperidine, 1-[(1-ethyl-3,5-dimethyl-1H-pyrazol-4-yl)sulfonyl]-4-(phenylmethyl).
Chemical Abstract Registry No. 958563-03-06, Entered STN: Dec. 18, 2007; Piperidine, 1-(1H-imidazol-5-ylsulfonyl)-4-(phenylmethyl).
Chemical Abstract Registry No. 902845-89-0; Entered STN: Aug. 20, 2006; 1H-Pyrrole-2-carboxylic acid, 1-methyl-4-[[4-(phenylmethyl)-1-piperidinyl]sulfonyl]-, ethyl ester.
Chemical Abstract Registry No. 897449-18-2; Entered STN: Jul. 31, 2006; Piperidine, 4-(phenylmethyl)-1-[(1,3,5-trimethyl-1H-pyrazol-4-yl)sulfonyl].
Chemical Abstract Registry No. 894894-29-2; Entered STN: Jul. 20, 2006; 1H-Pyrrole-3-carboxylic acid, 1,2,5-trimethyl-4-[[4-(phenylmethyl)-1-piperidinyl]sulfonyl]-, ethyl ester.
Chemical Abstract Registry No. 894579-46-5; Entered STN: Jul. 19, 2006; 1H-Pyrrole-3-carboxylic acid, 2,5-dimethyl-4-[[4-(phenylmethyl)-1-piperidinyl]sulfonyl]-, ethyl ester.
Chemical Abstract Registry No. 892087-67-1; Entered STN: Jul. 11, 2006; 1H-Pyrrole-2-carboxylic acid, 4-[[4-(phenylmethyl)-1-piperidinyl]sulfonyl]-, methyl ester.
Stoit, et al., "7-Azaindole derivatives as potential partial nicotinic agonists", Bioorganic & Medicinal Chemistry Letters, vol. 18, No. 1, Nov. 1, 2008, pp. 188-193.
Wang, et al., "Synthesis and Evaluation of 3-aryl piperidine analogs as potent and efficacious dopamine D4 receptor agonists", Bioorganic & Medicinal Chemistry, vol. 13, No. 15, May 17, 2005, pp. 4667-4678.
Chemistry Abstract Registry No. 1006341-60-1; Entered STN: Mar. 3, 2008, Piperidine 1-[[1-(difluoromethyl)-3,5-dimethyl-1H-pyrazol-4-yl]sulfonyl]-4-(phenylmethyl).
Chemical Abstract Registry No. 1006311-40-2; Entered STN: Mar. 3, 2008; Piperidine, 1-[(1-ethyl-3,5-dimethyl-1H-pyrazol-4-yl)sulfonyl]-4-(phenylmethyl).
Chemistry Abstract Registry No. 958563-03-6; Entered STN: Dec. 18, 2007, Piperidine, 1-(1H-imidazol-5-ylsulfonyl)-4-(phenylmethyl).
English translation of an Office Action in related Taiwanese Patent Application No. 102117795, filed May 20, 2013. Office Action dated Feb. 24, 2017 (3 Pages).

\* cited by examiner

SULFONYL PIPERIDINE DERIVATIVES AND THEIR USE FOR TREATING PROKINETICIN MEDIATED DISEASES

CROSS REFERENCE TO RELATED APPLICATIONS

This application claims priority to U.S. Ser. No. 16/707,079, entitled "Sulfonyl Piperidine Derivatives and Their Use for Treating Prokineticin Mediated Diseases", filed on Dec. 9, 2019 and is a divisional application of U.S. Ser. No. 15/262,436, entitled "Sulfonyl Piperidine Derivatives and Their Use for Treating Prokineticin Mediated Diseases", filed on Sep. 12, 2016, which is a continuation application of U.S. Ser. No. 14/402,751, entitled "Sulfonyl Piperidine Derivatives and Their Use for Treating Prokineticin Mediated Diseases", filed on Nov. 21, 2014, which claims priority to National Stage application under 35 U.S.C. 371 of PCT/GB2013/051415, filed on May 29, 2013 and published as WO 2013/179024 A1 on Dec. 5, 2013, which claims the benefit GB 1209587.3, filed May 30, 2012, the contents of which are incorporated herein by reference in its entirety.

The present invention relates to the use of piperidine derivatives in therapy, particularly for the treatment or prevention of psychiatric and neurological conditions.

Prokineticins are cysteine-rich regulatory peptides that are thought to exert signaling activity via two highly conserved G protein-coupled receptors (GPCR), the prokineticin receptor 1 (PKR1 or PROKR1) and the prokineticin receptor 2 (PKR2 or PROKR2), that belong to the 7-transmembrane domain, G protein-coupled receptor (GPCR) superfamily.

Prokineticin receptor 1 (also known as GPR73) shows 87% homology to Prokineticin Receptor 2 (also known as GPR73L1). Prokineticins (PK1 and PK2) contain 86 and 81 amino acids respectively, sharing 45% amino acid identity. Both prokineticins activate the two prokineticin receptors, PKR1 and PKR2, with similar potency.

PKR1 receptors couple to $G_q/G_{11}$ proteins leading to phospholipase C activation, inositol phosphate production and calcium mobilization. In addition, activation of the mitogen-activated protein kinase (MAPK) pathways has also been described.

PKR1 is broadly distributed throughout peripheral tissues including the intestinal tract, testis, uterus, lung, mouse dorsal root ganglia, macrophage, bone, heart, rectum, white adipose and peripheral blood leukocytes. In addition, the receptor is expressed in the brain particularly in olfactory regions as well as in dorsal root ganglion (DRG) neurons, house hippocampus, dentate gyrus, cerebellar cortex, cerebral cortex, human hippocampus, amygdala, medulla oblongata and spinal cord.

Prokineticins were originally identified as potent agents mediating gut motility, but were later shown to promote angiogenesis in steroidogenic glands (e.g. adrenal gland), heart and reproductive systems. They also modulate neurogenesis, circadian rhythms, nociception, haematopoiesis as well as the immune response. Prokineticins are thought to be associated with pathologies of the reproductive and nervous systems, myocardial infarction and tumorigenesis.

Consequently, antagonisim of the functions of the prokineticins may have utility in the treatment of disorders or diseases including gastrointestinal motility, angiogenesis, hematopoiesis, diabetes (e.g. as described in International Patent Application Publication No. WO 2010/077976) and pain (e.g. as described in International Patent Application Publication No. WO 2007/079214).

We have now discovered a new class of compounds that are prokineticin receptor modulators which have desirable activity profiles. The compounds of this invention have beneficial potency, selectivity and/or pharmacokinetic properties.

In accordance with the present invention, there is therefore provided a compound of formula (I)

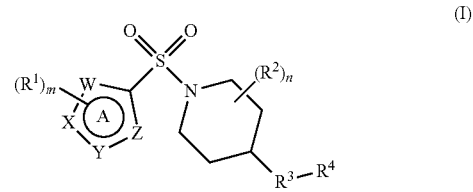

or a pharmaceutically acceptable salt thereof for use in therapy, in particular for treating a disease or condition mediated by a prokineticin, specifically prokineticin 1 (PK1) and/or prokineticin 2 (PK2), wherein in formula (I)

W, X, Y and Z each independently represent N, NH or CH, with the proviso that W, X, Y and Z do not each simultaneously represent a moiety CH;

m is 0, 1, 2 or 3;

each $R^1$ independently represents halogen, cyano, $C_1$-$C_6$ alkoxy, $C_1$-$C_6$ alkoxycarbonyl, $C_1$-$C_6$ haloalkyl, $C_1$-$C_6$ haloalkoxy, $C_1$-$C_6$ alkylthio, $C_1$-$C_6$ alkylcarbonyl, or $C_1$-$C_6$ alkyl optionally substituted by carboxyl or $C_1$-$C_6$ alkoxycarbonyl;

n is 0, 1, 2, 3 or 4;

each $R^2$ independently represents halogen, cyano, carboxyl, hydroxyl, $C_1$-$C_6$ alkyl, $C_1$-$C_6$ haloalkyl, $C_1$-$C_6$ alkoxy, $C_1$-$C_6$ hydroxyalkyl, $C_1$-$C_6$ alkoxycarbonyl, $C_1$-$C_6$ alkoxy$C_1$-$C_6$ alkyl or a 5- to 9-membered heterocyclic ring system;

$R^3$ represents an oxygen or sulphur atom, or a group C=O, $NR^5$ or $CR^6R^7$;

$R^5$ represents a hydrogen atom or a $C_1$-$C_6$ alkyl group;

$R^6$ and $R^7$ each independently represent a hydrogen or halogen atom or cyano, carboxyl, hydroxyl, $C_1$-$C_6$ alkyl, $C_1$-$C_6$ haloalkyl, $C_1$-$C_6$ alkoxy, $C_1$-$C_6$ hydroxyalkyl, $C_1$-$C_6$ alkoxycarbonyl, $C_1$-$C_6$ alkoxy$C_1$-$C_6$ alkyl or a 5- to 9-membered heterocyclic ring system;

$R^4$ represents a 6- to 10-membered aromatic or heteroaromatic ring system, the ring system itself being optionally substituted by at least one substituent selected from halogen, hydroxyl, cyano, oxo (=O), $C_1$-$C_6$ alkyl, $C_2$-$C_6$ alkenyl, $C_2$-$C_6$ alkynyl, $C_1$-$C_6$ haloalkyl, $C_1$-$C_6$ hydroxyalkyl, $C_1$-$C_6$ alkoxy, $C_1$-$C_6$ haloalkoxy, $C_1$-$C_6$ alkylthio, $C_1$-$C_6$ alkylsulphinyl, $C_1$-$C_6$ alkylsulphonyl, $C_1$-$C_6$ alkylcarbonyl, $C_1$-$C_6$ alkylcarbonyloxy, $C_1$-$C_6$ alkoxycarbonyl, amino (—$NH_2$), —CON($R^8$)$_2$, $C_1$-$C_6$ alkylamino, di-($C_1$-$C_6$ alkyl)amino, $C_3$-$C_6$ cycloalkyl, $C_3$-$C_6$ cycloalkyloxy or $C_3$-$C_6$ cycloalkylmethyl; and each $R^8$ independently represents a hydrogen atom or a $C_1$-$C_6$ alkyl group.

Certain compounds of formula (I) are novel compounds. Therefore the present invention further provides a compound of formula (Ia), or a pharmaceutically acceptable salt thereof,

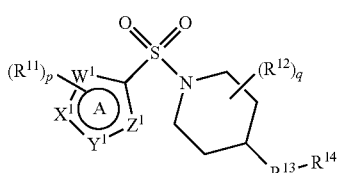

(Ia)

wherein
$W^1$, $X^1$, $Y^1$ and $Z^1$ each independently represent N, NH or CH, with the proviso that $W^1$, $X^1$, $Y^1$ and $Z^1$ do not each simultaneously represent a moiety CH;

p is 0, 1, 2 or 3;

each $R^{11}$ independently represents halogen, cyano, $C_1$-$C_6$ alkoxy, $C_1$-$C_6$ haloalkyl, $C_1$-$C_6$ haloalkoxy, $C_1$-$C_6$ alkylthio, $C_1$-$C_6$ alkylcarbonyl, or $C_1$-$C_6$ alkyl optionally substituted by carboxyl or $C_1$-$C_6$ alkoxycarbonyl;

q is 0, 1, 2, 3 or 4;

each $R^{12}$ independently represents halogen, cyano, carboxyl, hydroxyl, $C_1$-$C_6$ alkyl, $C_1$-$C_6$ haloalkyl, $C_1$-$C_6$ alkoxy, $C_1$-$C_6$ hydroxyalkyl, $C_1$-$C_6$ alkoxycarbonyl, $C_1$-$C_6$ alkoxy$C_1$-$C_6$ alkyl or a 5- to 9-membered heterocyclic ring system;

$R^{13}$ represents an oxygen atom, or a group C=O, $NR^{15}$ or $CR^{16}R^{17}$, with the provisos that (i) when $R^{13}$ represents CO or NH and ring A represents pyrazol-4-yl or imidazol-4-yl, then p must be 3 and $R^{14}$ represents a substituted 6- to 10-membered aromatic or heteroaromatic ring system, and (ii) when $R^{13}$ represents $CH_2$ and ring A represents pyrazol-4-yl or imidazol-4-yl, then either p is 3, or, p is 2 and q is at least 1;

$R^{15}$ represents a hydrogen atom or a $C_1$-$C_6$ alkyl group;

$R^{16}$ and $R^{17}$ each independently represent a hydrogen or halogen atom or cyano, carboxyl, hydroxyl, $C_1$-$C_6$ alkyl, $C_1$-$C_6$ haloalkyl, $C_1$-$C_6$ alkoxy, $C_1$-$C_6$ hydroxyalkyl, $C_1$-$C_6$ alkoxycarbonyl, $C_1$-$C_6$ alkoxy$C_1$-$C_6$ alkyl or a 5- to 9-membered heterocyclic ring system;

$R^{14}$ represents a 6- to 10-membered aromatic or heteroaromatic ring system, the ring system itself being optionally substituted by at least one substituent selected from halogen, hydroxyl, cyano, oxo (=O), $C_1$-$C_6$ alkyl, $C_2$-$C_6$ alkenyl, $C_2$-$C_6$ alkynyl, $C_1$-$C_6$ haloalkyl, $C_1$-$C_6$ hydroxyalkyl, $C_1$-$C_6$ alkoxy, $C_1$-$C_6$ haloalkoxy, $C_1$-$C_6$ alkylthio, $C_1$-$C_6$ alkylsulphinyl, $C_1$-$C_6$ alkylsulphonyl, $C_1$-$C_6$ alkylcarbonyl, $C_1$-$C_6$ alkylcarbonyloxy, $C_1$-$C_6$ alkoxycarbonyl, amino (—$NH_2$), —$CON(R^{18})_2$, $C_1$-$C_6$ alkylamino, di-($C_1$-$C_6$ alkyl)amino, $C_3$-$C_6$ cycloalkyl, $C_3$-$C_6$ cycloalkyloxy or $C_3$-$C_6$ cycloalkylmethyl; and each $R^{18}$ independently represents a hydrogen atom or a $C_1$-$C_6$ alkyl group; but excluding the following compounds:

1) 1-[(3,5-dimethyl-1H-pyrazol-4-yl)sulfonyl]-4-(4-methylphenoxy)piperidine,
2) 1-[(3,5-dimethyl-1H-pyrazol-4-yl)sulfonyl]-4-(4-fluorophenoxy)piperidine,
3) 1-[(3,5-dimethyl-1H-pyrazol-4-yl)sulfonyl]-4-(4-methoxyphenoxy)piperidine,
4) 1-[(3,5-dimethyl-1H-pyrazol-4-yl)sulfonyl]-4-phenoxypiperidine,
5) 1-[(3,5-dimethyl-1H-pyrazol-4-yl)sulfonyl]-4-(3-ethylphenoxy)piperidine,
6) 4-phenoxy-1-(1H-pyrazol-4-ylsulfonyl)piperidine,
7) 4-(3-chlorophenoxy)-1-[(3,5-dimethyl-1H-pyrazol-4-yl)sulfonyl]piperidine,
8) [1-[(5-chloro-1,3-dimethyl-1H-pyrazol-4-yl)sulfonyl]-4-piperidinyl](4-methoxyphenyl)methanone,
9) 1-[(3,5-dimethyl-1H-pyrazol-4-yl)sulfonyl]-4-(2-methylphenoxy)piperidine,
10) 1-[(3,5-dimethyl-1H-pyrazol-4-yl)sulfonyl]-4-[[2-(trifluoromethyl)phenyl]methyl]-4-piperidinemethanol,
11) 1-[(3,5-dimethyl-1H-pyrazol-4-yl)sulfonyl]-4-[(4-methoxyphenyl)methyl]-4-piperidinecarboxylic acid, ethyl ester,
12) 4-[[1-[(1-methyl-1H-pyrazol-4-yl)sulfonyl]-4-piperidinyl]oxy]benzonitrile,
13) N-(2-methylphenyl)-1-[(1,3,5-trimethyl-1H-pyrazol-4-yl)sulfonyl]-4-piperidineamine,
14) 1-[[1-(difluoromethyl)-3-methyl-1H-pyrazol-4-yl]sulfonyl]-4-(4-fluorophenoxy)piperidine,
15) 4-(3-fluorophenoxy)-1-[(3-methyl-1-propyl-1H-pyrazol-4-yl)sulfonyl]piperidine,
16) 1-[[1-(difluoromethyl)-3,5-dimethyl-1H-pyrazol-4-yl]sulfonyl]-4-(2-fluorophenoxy)piperidine,
17) 1-[(5-chloro-1,3-dimethyl-1H-pyrazol-4-yl)sulfonyl]-4-(phenylmethyl)piperidine,
18) 1-[[1-(difluoromethyl)-3,5-dimethyl-1H-pyrazol-4-yl]sulfonyl]-4-(phenylmethyl)piperidine,
19) 1-[(1-ethyl-3,5-dimethyl-1H-pyrazol-4-yl)sulfonyl]-4-(phenylmethyl)piperidine, 20) (4-(4-Methoxybenzyl)-1-(1,3,5-trimethyl-1H-pyrazol-4-yl)sulfonyl)piperidin-4-yl)methanol,
21) (4-(4-Chlorobenzyl)-1-(1,3,5-trimethyl-1H-pyrazol-4-yl)sulfonyl)piperidin-4-yl)methanol,
22) 1-[(5-chloro-1,3-dimethyl-1H-pyrazol-4-yl)sulfonyl]-4-[(4-methoxyphenyl)methyl]-4-piperidinemethanol,
23) 4-(phenylmethyl)-1-[(1,3,5-trimethyl-1H-pyrazol-4-yl)sulfonyl]piperidine,
24) [1-[(5-chloro-1,3-dimethyl-1H-pyrazol-4-yl)sulfonyl]-4-piperidinyl](4-fluorophenyl)methanone, and
25) 2-[[1-[3,5-dimethyl-1H-pyrazol-4-yl)sulfonyl]-4-piperidinyl]oxy]pyrazine.

In the context of the present specification, unless otherwise stated, an alkyl, alkenyl or alkynyl substituent group or an alkyl, alkenyl or alkynyl moiety in a substituent group may be linear or branched. Examples of $C_1$-$C_6$ alkyl groups/moieties include methyl, ethyl, propyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, tert-butyl, n-pentyl, isopentyl, neopentyl and n-hexyl. Examples of $C_2$-$C_6$ alkenyl groups/moieties include ethenyl, propenyl, 1-butenyl, 2-butenyl, 1-pentenyl, 1-hexenyl, 1,3-butadienyl, 1,3-pentadienyl, 1,4-pentadienyl and 1-hexadienyl. Examples of $C_2$-$C_6$ alkynyl groups/moieties include ethynyl, propynyl, 1-butynyl, 2-butynyl, 1-pentynyl and 1-hexynyl.

A $C_1$-$C_6$ haloalkyl or $C_1$-$C_6$ haloalkoxy substituent group/moiety will comprise at least one halogen atom, e.g. one, two, three, four or five halogen atoms, examples of which include trifluoromethyl, trifluoromethoxy or pentafluoroethyl.

A $C_1$-$C_6$ hydroxyalkyl substituent group/moiety will comprise at least one hydroxyl group, e.g. one, two, three or four hydroxyl groups, examples of which include —$CH_2OH$, —$CH_2CH_2OH$, —$CH_2CH_2CH_2OH$, —$CH(OH)CH_2OH$, —$CH(CH_3)OH$ and —$CH(CH_2OH)_2$.

The alkyl groups in a di-$C_1$-$C_6$ alkylamino group/moiety may be the same as, or different from, one another.

The ring A in formula (I) or (Ia) is a 5-membered heteroaromatic ring containing from 1 to 4 ring nitrogen atoms, examples of which include pyrrolyl, imidazolyl, pyrazolyl, triazolyl and tetrazolyl.

A heterocyclic ring system means a saturated, partially unsaturated or fully unsaturated hydrocarbyl group containing from 5 to 9 ring atoms in which one or more (e.g. one, two, three or four) ring carbon atoms are replaced by a corresponding number of ring heteroatoms independently selected from nitrogen, oxygen and sulphur, particularly nitrogen and oxygen. Examples of heterocyclic ring systems include tetrahydrofuranyl, piperidinyl, pyrrolidinyl, tetrahydropyranyl, morpholinyl, thiamorpholinyl, dihydrobenzofuranyl, dihydrobenzothienyl and indolyl.

When any chemical moiety or group in formula (I) or (Ia) is described as being optionally substituted, it will be appreciated that the moiety or group may be either unsubstituted or substituted by one or more of the specified substituents. It will be appreciated that the number and nature of substituents will be selected so as to avoid sterically undesirable combinations.

In ring A of the compounds of formula (I), at least one of W, X, Y and Z represents N or NH. In one aspect of the invention, Y represents N or NH and W, X and Z each independently represent N, NH or CH. In a further aspect, Y represents N and W, X and Z each represent CH.

In one embodiment of the invention, at least two of W, X, Y and Z represent N or NH. Particularly advantageous compounds are those in which (i) X and Y each independently represent N or NH and W and Z both represent CH, or (ii) Y and Z each independently represent N or NH and W and X both represent CH, or (iii) W and X each independently represent N or NH and Y and Z both represent CH.

In another embodiment, at least three of W, X, Y and Z independently represent N or NH.

Specific examples of ring A, in which m and $R^1$ are as previously defined, include:

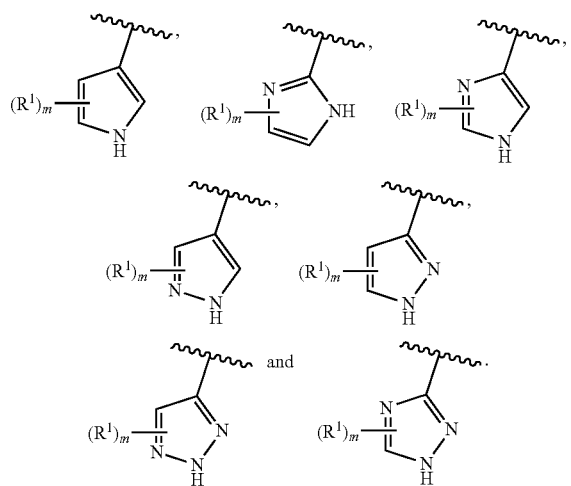

Advantageously, the ring A (where the substituents $R^1$, which may be the same or different, are as previously defined) is selected from the following moieties:

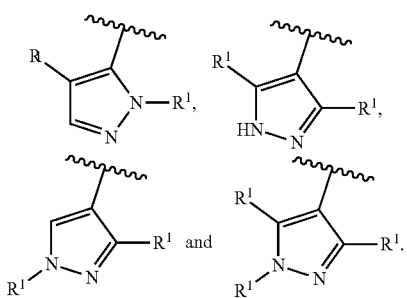

In particular, the ring A may be selected from one of the following moieties:

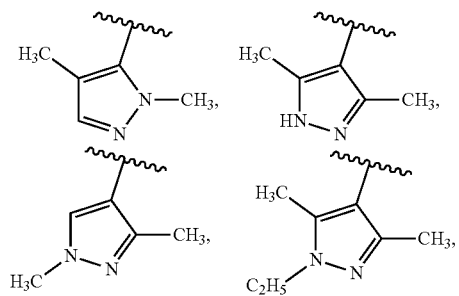

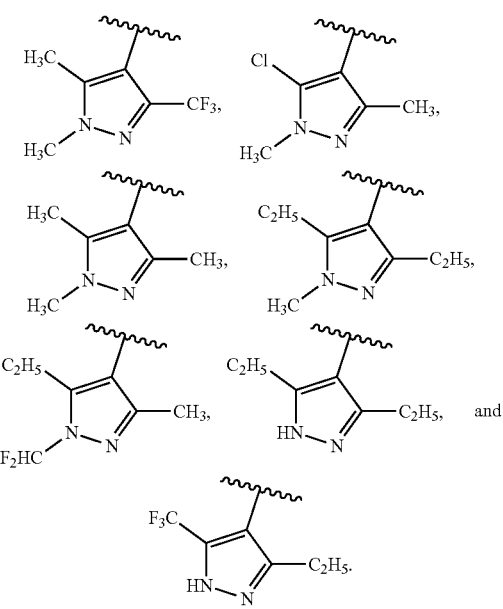

The number (m) of substituents $R^1$ on ring A may be 0, 1, 2 or 3, preferably 2 or 3.

If present on ring A, each $R^1$ independently represents halogen (e.g. fluorine, chlorine or bromine), cyano, $C_1$-$C_6$, or $C_1$-$C_4$, or $C_1$-$C_2$ alkoxy, $C_1$-$C_6$, or $C_1$-$C_4$, or $C_1$-$C_2$ alkoxycarbonyl, $C_1$-$C_6$, or $C_1$-$C_4$, or $C_1$-$C_2$ haloalkyl, $C_1$-$C_6$, or $C_1$-$C_4$, or $C_1$-$C_2$ haloalkoxy, $C_1$-$C_6$, or $C_1$-$C_4$, or $C_1$-$C_2$ alkylthio, $C_1$-$C_6$, or $C_1$-$C_4$, or $C_1$-$C_2$ alkylcarbonyl, or $C_1$-$C_6$, or $C_1$-$C_4$, or $C_1$-$C_2$ alkyl optionally substituted by one or more (e.g. one, two, three or four) substituents independently selected from carboxyl and $C_1$-$C_6$, or $C_1$-$C_4$, or $C_1$-$C_2$ alkoxycarbonyl.

In an embodiment of the invention, each $R^1$ independently represents halogen (e.g. fluorine, chlorine or bromine), cyano, $C_1$-$C_2$ alkoxy, $C_1$-$C_2$ alkoxycarbonyl, $C_1$-$C_2$ haloalkyl (e.g. difluoromethyl or trifluoromethyl), $C_1$-$C_2$ haloalkoxy (e.g. difluoromethoxy or trifluoromethoxy), $C_1$-$C_2$ alkylthio, $C_1$-$C_2$ alkylcarbonyl, or $C_1$-$C_6$, or $C_1$-$C_4$, or $C_1$-$C_2$ alkyl optionally substituted by one or more (e.g. one, two, three or four) substituents independently selected from carboxyl and $C_1$-$C_6$, or $C_1$-$C_4$, or $C_1$-$C_2$ alkoxycarbonyl.

In another embodiment, each $R^1$ independently represents halogen (e.g. fluorine, chlorine or bromine, especially chlorine), $C_1$-$C_2$ haloalkyl (e.g. difluoromethyl or trifluoromethyl) or $C_1$-$C_6$, or $C_1$-$C_4$, or $C_1$-$C_2$ alkyl (especially methyl or ethyl).

The number (n) of substituents $R^2$ on the piperidine ring may be 0, 1, 2, 3 or 4, and is preferably 0 or 1. A substituent $R^2$ may be attached at any suitable position on the piperidine ring but is preferably attached at the 4-position relative to the ring nitrogen atom, i.e. the substituent $R^2$ is preferably attached to the same ring carbon atom as the group $R^3$.

If present, each $R^2$ independently represents halogen (e.g. fluorine, chlorine or bromine), cyano, carboxyl, hydroxyl, $C_1$-$C_6$, or $C_1$-$C_4$, or $C_1$-$C_2$ alkyl, $C_1$-$C_6$, or $C_1$-$C_4$, or $C_1$-$C_2$ haloalkyl, $C_1$-$C_6$, or $C_1$-$C_4$, or $C_1$-$C_2$ alkoxy, $C_1$-$C_6$, or $C_1$-$C_4$, or $C_1$-$C_2$ hydroxyalkyl, $C_1$-$C_6$, or $C_1$-$C_4$, or $C_1$-$C_2$ alkoxycarbonyl, $C_1$-$C_6$, or $C_1$-$C_4$, or $C_1$-$C_2$ alkoxy$C_1$-$C_6$ alkyl or a 5-, 6-, 7-, 8- or 9-membered heterocyclic ring system.

In one embodiment, each $R^2$ independently represents halogen (e.g. fluorine, chlorine or bromine), cyano, carboxyl, hydroxyl, $C_1$-$C_2$ alkyl (especially methyl), $C_1$-$C_2$ haloalkyl (e.g. difluoromethyl or trifluoromethyl), $C_1$-$C_2$ alkoxy (especially methoxy), $C_1$-$C_2$ hydroxyalkyl (e.g. hydroxymethyl), $C_1$-$C_2$ alkoxycarbonyl (especially ethoxycarbonyl), $C_1$-$C_2$ alkoxy$C_1$-$C_6$ alkyl (preferably $C_1$-$C_2$ alkoxy$C_1$-$C_2$ alkyl) or a 5- to 6-membered heterocyclic ring system containing one or two ring heteroatoms independently selected from nitrogen and oxygen.

In another embodiment, each $R^2$ independently represents halogen (especially fluorine), cyano, hydroxyl, $C_1$-$C_2$ alkyl (especially methyl), $C_1$-$C_2$ alkoxy (especially methoxy), $C_1$-$C_2$ alkoxycarbonyl (especially ethoxycarbonyl), or $C_1$-$C_2$ alkoxy$C_1$-$C_2$ alkyl (particularly methoxymethyl).

In still another embodiment, each $R^2$ independently represents cyano, hydroxyl, $C_1$-$C_2$ alkyl (especially methyl), $C_1$-$C_2$ alkoxy (especially methoxy), $C_1$-$C_2$ alkoxycarbonyl (especially ethoxycarbonyl), or $C_1$-$C_2$ alkoxy$C_1$-$C_2$ alkyl (particularly methoxymethyl).

$R^3$ represents an oxygen or sulphur atom, or a group C=O, $NR^5$ or $CR^6R^7$ where $R^5$ represents a hydrogen atom or a $C_1$-$C_6$, or $C_1$-$C_4$, or $C_1$-$C_2$ alkyl (preferably methyl) group and $R^6$ and $R^7$ each independently represent a hydrogen or halogen (e.g. fluorine, chlorine or bromine) atom, cyano, carboxyl, hydroxyl, $C_1$-$C_6$, or $C_1$-$C_4$, or $C_1$-$C_2$ alkyl, $C_1$-$C_6$, or $C_1$-$C_4$, or $C_1$-$C_2$ haloalkyl, $C_1$-$C_6$, or $C_1$-$C_4$, or $C_1$-$C_2$ alkoxy, $C_1$-$C_6$, or $C_1$-$C_4$, or $C_1$-$C_2$ hydroxyalkyl, $C_1$-$C_6$, or $C_1$-$C_4$, or $C_1$-$C_2$ alkoxycarbonyl, $C_1$-$C_6$, or $C_1$-$C_4$, or $C_1$-$C_2$ alkoxy$C_1$-$C_6$ alkyl or a 5-, 6-, 7-, 8- or 9-membered heterocyclic ring system.

In one embodiment, $R^6$ and $R^7$ each independently represent a hydrogen or halogen (e.g. fluorine, chlorine or bromine) atom, cyano, hydroxyl, $C_1$-$C_2$ alkyl (preferably methyl), $C_1$-$C_2$ haloalkyl (e.g. difluoromethyl or trifluoromethyl), $C_1$-$C_2$ alkoxy, $C_1$-$C_2$ hydroxyalkyl (e.g. hydroxymethyl), or $C_1$-$C_2$ alkoxy$C_1$-$C_2$ alkyl (particularly methoxymethyl).

In one aspect of the invention, $R^3$ represents an oxygen atom or a group C=O, $NR^5$ or $CR^6R^7$.

In another aspect, $R^3$ represents an oxygen atom or a group $NR^5$ or $CR^6R^7$.

In yet another aspect, $R^3$ represents an oxygen atom or a group C=O, NH, N(CH$_3$), CH$_2$, CHF, CHCN, CH(OH), CH(OCH$_3$), CH(OC$_2$H$_5$), CH(CH$_2$OH), C(OH)CH$_3$, CH(CH$_3$), CH(CH$_2$OCH$_3$) or CH(CHF$_2$).

In a further aspect, $R^3$ represents an oxygen atom or a group NH, N(CH$_3$), CH$_2$, CHF, CHCN, CH(OH), CH(OCH$_3$), CH(OC$_2$H$_5$), CH(CH$_2$OH), C(OH)CH$_3$, CH(CH$_3$), CH(CH$_2$OCH$_3$) or CH(CHF$_2$).

In a still further aspect, $R^3$ represents an oxygen atom or a group C=O, NH, N(CH$_3$) or CH$_2$.

Compounds of formula (I) in which $R^3$ is an oxygen atom are particularly preferred.

$R^4$ represents a 6-, 7-, 8-, 9- or 10-membered aromatic or heteroaromatic ring system, the ring system itself being optionally substituted by at least one substituent (e.g. one, two, three or four substituents independently) selected from halogen (e.g. fluorine, chlorine or bromine), hydroxyl, cyano, oxo (=O), $C_1$-$C_6$, or $C_1$-$C_4$, or $C_1$-$C_2$ alkyl, $C_2$-$C_6$ or $C_2$-$C_4$ alkenyl, $C_2$-$C_6$ or $C_2$-$C_4$ alkynyl, $C_1$-$C_6$, or $C_1$-$C_4$, or $C_1$-$C_2$ haloalkyl, $C_1$-$C_6$, or $C_1$-$C_4$, or $C_1$-$C_2$ hydroxyalkyl, $C_1$-$C_6$, or $C_1$-$C_4$, or $C_1$-$C_2$ alkoxy, $C_1$-$C_6$, or $C_1$-$C_4$, or $C_1$-$C_2$ haloalkoxy, $C_1$-$C_6$, or $C_1$-$C_4$, or $C_1$-$C_2$ alkylthio, $C_1$-$C_6$, or $C_1$-$C_4$, or $C_1$-$C_2$ alkylsulphinyl, $C_1$-$C_6$, or $C_1$-$C_4$, or $C_1$-$C_2$ alkylsulphonyl, $C_1$-$C_6$, or $C_1$-$C_4$, or $C_1$-$C_2$ alkylcarbonyl, $C_1$-$C_6$, or $C_1$-$C_4$, or $C_1$-$C_2$ alkylcarbonyloxy, $C_1$-$C_6$, or $C_1$-$C_4$, or $C_1$-$C_2$ alkoxycarbonyl, amino (—NH$_2$), —CON(R$^8$)$_2$, $C_1$-$C_6$, or $C_1$-$C_4$, or $C_1$-$C_2$ alkylamino, di-($C_1$-$C_6$ alkyl)amino, $C_3$-$C_6$ cycloalkyl, $C_3$-$C_6$ cycloalkyloxy and $C_3$-$C_6$ cycloalkylmethyl.

The heteroaromatic ring system will comprise at least one ring heteroatom (e.g. one, two, three or four ring heteroatoms independently) selected from nitrogen, sulphur and oxygen. Preferably the ring heteroatoms are selected from nitrogen and oxygen.

Examples of 6- to 10-membered aromatic or heteroaromatic ring systems that may be used, which may be monocyclic or polycyclic (e.g. bicyclic) in which the two or more rings are fused, include one or more (in any combination) of phenyl, pyridinyl, naphthyl, benzofuranyl, benzothienyl, quinolinyl, imidazo[1,2-a]pyridinyl, pyrazinyl, indolyl, pyrimidinyl, thiophenyl and benzimidazolyl. Preferred ring systems include phenyl, naphthyl and pyridinyl.

In one embodiment of the invention, $R^4$ represents a 6-, 7-, 8-, 9- or 10-membered aromatic or heteroaromatic ring system, the ring system itself being optionally substituted by at least one substituent (e.g. one, two, three or four substituents independently) selected from halogen (e.g. fluorine, chlorine or bromine), hydroxyl, cyano, oxo, $C_1$-$C_4$ alkyl (e.g. methyl or ethyl), $C_2$-$C_4$ alkenyl (e.g. ethenyl), $C_2$-$C_4$ alkynyl (e.g. ethynyl), $C_1$-$C_2$ haloalkyl (e.g. trifluoromethyl), $C_1$-$C_2$ hydroxyalkyl (e.g. hydroxymethyl), $C_1$-$C_4$ alkoxy (e.g. methoxy or ethoxy), $C_1$-$C_2$ haloalkoxy (e.g. trifluoromethoxy), $C_1$-$C_4$ alkylthio (e.g. methylthio or ethylthio), $C_1$-$C_4$ alkylsulphinyl (e.g. methylsulphinyl or ethylsulphinyl), $C_1$-$C_4$ alkylsulphonyl (e.g. methylsulphonyl or ethylsulphonyl), $C_1$-$C_4$ alkylcarbonyl (e.g. methylcarbonyl or ethylcarbonyl), $C_1$-$C_4$ alkylcarbonyloxy (e.g. methylcarbonyloxy), $C_1$-$C_4$ alkoxycarbonyl (e.g. methoxycarbonyl), amino, —CON(R$^8$)$_2$, $C_1$-$C_4$ alkylamino (e.g. methylamino or ethylamino), di-($C_1$-$C_4$ alkyl)amino (e.g. dimethylamino), $C_3$-$C_5$ cycloalkyl, $C_3$-$C_5$ cycloalkyloxy and $C_3$-$C_5$ cycloalkylmethyl.

In another embodiment of the invention, $R^4$ represents a 6-, 7-, 8-, 9- or 10-membered, particularly 6-membered, aromatic or heteroaromatic (particularly a nitrogen-containing heteroaromatic) ring system, the ring system itself being optionally substituted by at least one substituent (e.g. one, two, three or four substituents independently) selected from halogen (e.g. fluorine, chlorine or bromine), cyano, $C_1$-$C_4$ alkyl (e.g. methyl or ethyl), $C_1$-$C_2$ haloalkyl (e.g. trifluoromethyl), $C_1$-$C_4$ alkoxy (e.g. methoxy or ethoxy) and $C_1$-$C_2$ haloalkoxy (e.g. trifluoromethoxy).

In still another embodiment of the invention, $R^4$ represents a 6-, 7-, 8-, 9- or 10-membered, particularly 6-membered, aromatic or heteroaromatic (particularly a nitrogen-containing heteroaromatic) ring system, the ring system itself being optionally substituted by at least one substituent (preferably up to three, most preferably one or two, substituents independently) selected from halogen (e.g. fluorine, chlorine or bromine), cyano, methyl, trifluoromethyl, methoxy and trifluoromethoxy.

Each $R^8$ independently represents a hydrogen atom or a $C_1$-$C_6$, or $C_1$-$C_4$, or $C_1$-$C_2$ alkyl, particularly methyl, group.

In the compounds of formula (Ia), the definitions of $W^1$, $X^1$, $Y^1$ and $Z^1$ correspond respectively to the definitions of W, X, Y and Z in the compounds of formula (I) as described above. Similarly the definitions of p and q correspond respectively to the definitions of m and n in the compounds of formula (I) as previously described.

If present on ring A, each $R^{11}$ independently represents halogen (e.g. fluorine, chlorine or bromine), cyano, $C_1$-$C_6$, or $C_1$-$C_4$, or $C_1$-$C_2$ alkoxy, $C_1$-$C_6$, or $C_1$-$C_4$, or $C_1$-$C_2$ haloalkyl, $C_1$-$C_6$, or $C_1$-$C_4$, or $C_1$-$C_2$ haloalkoxy, $C_1$-$C_6$, or $C_1$-$C_4$, or $C_1$-$C_2$ alkylthio, $C_1$-$C_6$, or $C_1$-$C_4$, or $C_1$-$C_2$ alkylcarbonyl, or $C_1$-$C_6$, or $C_1$-$C_4$, or $C_1$-$C_2$ alkyl optionally substituted by one or more (e.g. one, two, three or four) substituents independently selected from carboxyl and $C_1$-$C_6$, or $C_1$-$C_4$, or $C_1$-$C_2$ alkoxycarbonyl.

In an embodiment of the invention, each $R^{11}$ independently represents halogen (e.g. fluorine, chlorine or bromine), cyano, $C_1$-$C_2$ alkoxy, $C_1$-$C_2$ haloalkyl (e.g. difluoromethyl or trifluoromethyl), $C_1$-$C_2$ haloalkoxy (e.g. difluoromethoxy or trifluoromethoxy), $C_1$-$C_2$ alkylthio, $C_1$-$C_2$ alkylcarbonyl, or $C_1$-$C_6$, or $C_1$-$C_4$, or $C_1$-$C_2$ alkyl optionally substituted by one or more (e.g. one, two, three or four) substituents independently selected from carboxyl and $C_1$-$C_6$, or $C_1$-$C_4$, or $C_1$-$C_2$ alkoxycarbonyl.

In another embodiment, each $R^{11}$ independently represents halogen (e.g. fluorine, chlorine or bromine, especially chlorine), $C_1$-$C_2$ haloalkyl (e.g. difluoromethyl or trifluoromethyl) or $C_1$-$C_6$, or $C_1$-$C_4$, or $C_1$-$C_2$ alkyl (especially methyl or ethyl).

The group $R^{12}$ in formula (Ia) corresponds to and has the same meanings as the group $R^2$ in formula (I). Thus, if present, each $R^{12}$ independently represents halogen (e.g. fluorine, chlorine or bromine), cyano, carboxyl, hydroxyl, $C_1$-$C_6$, or $C_1$-$C_4$, or $C_1$-$C_2$ alkyl, $C_1$-$C_6$, or $C_1$-$C_4$, or $C_1$-$C_2$ haloalkyl, $C_1$-$C_6$, or $C_1$-$C_4$, or $C_1$-$C_2$ alkoxy, $C_1$-$C_6$, or $C_1$-$C_4$, or $C_1$-$C_2$ hydroxyalkyl, $C_1$-$C_6$, or $C_1$-$C_4$, or $C_1$-$C_2$ alkoxycarbonyl, $C_1$-$C_6$, or $C_1$-$C_4$, or $C_1$-$C_2$ alkoxy$C_1$-$C_6$ alkyl or a 5-, 6-, 7-, 8- or 9-membered heterocyclic ring system.

In one embodiment, each $R^{12}$ independently represents halogen (e.g. fluorine, chlorine or bromine), cyano, carboxyl, hydroxyl, $C_1$-$C_2$ alkyl (especially methyl), $C_1$-$C_2$ haloalkyl (e.g. difluoromethyl or trifluoromethyl), $C_1$-$C_2$ alkoxy (especially methoxy), $C_1$-$C_2$ hydroxyalkyl (e.g. hydroxymethyl), $C_1$-$C_2$ alkoxycarbonyl (especially ethoxycarbonyl), $C_1$-$C_2$ alkoxy$C_1$-$C_6$ alkyl (preferably $C_1$-$C_2$ alkoxy$C_1$-$C_2$ alkyl) or a 5- to 6-membered heterocyclic ring system containing one or two ring heteroatoms independently selected from nitrogen and oxygen.

In another embodiment, each $R^{12}$ independently represents halogen (especially fluorine), cyano, hydroxyl, $C_1$-$C_2$ alkyl (especially methyl), $C_1$-$C_2$ alkoxy (especially methoxy), $C_1$-$C_2$ alkoxycarbonyl (especially ethoxycarbonyl), or $C_1$-$C_2$ alkoxy$C_1$-$C_2$ alkyl (particularly methoxymethyl).

In still another embodiment, each $R^{12}$ independently represents cyano, hydroxyl, $C_1$-$C_2$ alkyl (especially methyl), $C_1$-$C_2$ alkoxy (especially methoxy), $C_1$-$C_2$ alkoxycarbonyl (especially ethoxycarbonyl), or $C_1$-$C_2$ alkoxy$C_1$-$C_2$ alkyl (particularly methoxymethyl).

$R^{13}$ represents an oxygen atom, or a group C=O, $NR^{15}$ or $CR^{16}R^{17}$, with the provisos that (i) when $R^{13}$ represents CO or NH and ring A represents pyrazol-4-yl or imidazol-4-yl, then p must be 3 and $R^{14}$ represents a substituted (but not an unsubstituted) 6- to 10-membered aromatic or heteroaromatic ring system, and (ii) when $R^{13}$ represents $CH_2$ and ring A represents pyrazol-4-yl or imidazol-4-yl, then either p is 3 or, alternatively, p is 2 and q is at least 1.

$R^{15}$ represents a hydrogen atom or a $C_1$-$C_6$, or $C_1$-$C_4$, or $C_1$-$C_2$ alkyl (preferably methyl) group and $R^{16}$ and $R^{17}$ each independently represent a hydrogen or halogen (e.g. fluorine, chlorine or bromine) atom, cyano, carboxyl, hydroxyl, $C_1$-$C_6$, or $C_1$-$C_4$, or $C_1$-$C_2$ alkyl, $C_1$-$C_6$, or $C_1$-$C_4$, or $C_1$-$C_2$ haloalkyl, $C_1$-$C_6$, or $C_1$-$C_4$, or $C_1$-$C_2$ alkoxy, $C_1$-$C_6$, or $C_1$-$C_4$, or $C_1$-$C_2$ hydroxyalkyl, $C_1$-$C_6$, or $C_1$-$C_4$, or $C_1$-$C_2$ alkoxycarbonyl, $C_1$-$C_6$, or $C_1$-$C_4$, or $C_1$-$C_2$ alkoxy$C_1$-$C_6$ alkyl or a 5-, 6-, 7-, 8- or 9-membered heterocyclic ring system.

In one embodiment, $R^{16}$ and $R^{17}$ each independently represent a hydrogen or halogen (e.g. fluorine, chlorine or bromine) atom, cyano, hydroxyl, $C_1$-$C_2$ alkyl (preferably methyl), $C_1$-$C_2$ haloalkyl (e.g. difluoromethyl or trifluoromethyl), $C_1$-$C_2$ alkoxy, $C_1$-$C_2$ hydroxyalkyl (e.g. hydroxymethyl), or $C_1$-$C_2$ alkoxy$C_1$-$C_2$ alkyl (particularly methoxymethyl).

Subject to the above provisos, in one aspect, $R^{13}$ represents an oxygen atom or a group $NR^{15}$ or $CR^{16}R^{17}$. In a second aspect, $R^{13}$ represents an oxygen atom or a group C=O, NH, $N(CH_3)$, $CH_2$, CHF, CHCN, CH(OH), $CH(OCH_3)$, $CH(OC_2H_5)$, $CH(CH_2OH)$, $C(OH)CH_3$, $CH(CH_3)$, $CH(CH_2OCH_3)$ or $CH(CHF_2)$. In a third aspect, $R^{13}$ represents an oxygen atom or a group NH, $N(CH_3)$, $CH_2$, CHF, CHCN, CH(OH), $CH(OCH_3)$, $CH(OC_2H_5)$, $CH(CH_2OH)$, $C(OH)CH_3$, $CH(CH_3)$, $CH(CH_2OCH_3)$ or $CH(CHF_2)$. In a fourth aspect, $R^{13}$ represents an oxygen atom. In a fifth aspect, $R^{13}$ represents $CH_2$.

The group $R^{14}$ in formula (Ia) corresponds to and has the same meanings as the group $R^4$ in formula (I).

Thus, $R^{14}$ represents a 6-, 7-, 8-, 9- or 10-membered aromatic or heteroaromatic ring system, the ring system itself being optionally substituted by at least one substituent (e.g. one, two, three or four substituents independently) selected from halogen (e.g. fluorine, chlorine or bromine), hydroxyl, cyano, oxo (=O), $C_1$-$C_6$, or $C_1$-$C_4$, or $C_1$-$C_2$ alkyl, $C_2$-$C_6$ or $C_2$-$C_4$ alkenyl, $C_2$-$C_6$ or $C_2$-$C_4$ alkynyl, $C_1$-$C_6$, or $C_1$-$C_4$, or $C_1$-$C_2$ haloalkyl, $C_1$-$C_6$, or $C_1$-$C_4$, or $C_1$-$C_2$ hydroxyalkyl, $C_1$-$C_6$, or $C_1$-$C_4$, or $C_1$-$C_2$ alkoxy, $C_1$-$C_6$, or $C_1$-$C_4$, or $C_1$-$C_2$ haloalkoxy, $C_1$-$C_6$, or $C_1$-$C_4$, or $C_1$-$C_2$ alkylthio, $C_1$-$C_6$, or $C_1$-$C_4$, or $C_1$-$C_2$ alkylsulphinyl, $C_1$-$C_6$, or $C_1$-$C_4$, or $C_1$-$C_2$ alkylsulphonyl, $C_1$-$C_6$, or $C_1$-$C_4$, or $C_1$-$C_2$ alkylcarbonyl, $C_1$-$C_6$, or $C_1$-$C_4$, or $C_1$-$C_2$ alkylcarbonyloxy, $C_1$-$C_6$, or $C_1$-$C_4$, or $C_1$-$C_2$ alkoxycarbonyl, amino (—$NH_2$), —$CON(R^{18})_2$, $C_1$-$C_6$, or $C_1$-$C_4$, or $C_1$-$C_2$ alkylamino, di-($C_1$-$C_6$ alkyl)amino, $C_3$-$C_6$ cycloalkyl, $C_3$-$C_6$ cycloalkyloxy and $C_3$-$C_6$ cycloalkylmethyl.

In one embodiment of the invention, $R^{14}$ represents a 6-, 7-, 8-, 9- or 10-membered aromatic or heteroaromatic ring system, the ring system itself being optionally substituted by at least one substituent (e.g. one, two, three or four substituents independently) selected from halogen (e.g. fluorine, chlorine or bromine), hydroxyl, cyano, oxo, $C_1$-$C_4$ alkyl (e.g. methyl or ethyl), $C_2$-$C_4$ alkenyl (e.g. ethenyl), $C_2$-$C_4$ alkynyl (e.g. ethynyl), $C_1$-$C_2$ haloalkyl (e.g. trifluoromethyl), $C_1$-$C_2$ hydroxyalkyl (e.g. hydroxymethyl), $C_1$-$C_4$ alkoxy (e.g. methoxy or ethoxy), $C_1$-$C_2$ haloalkoxy (e.g. trifluoromethoxy), $C_1$-$C_4$ alkylthio (e.g. methylthio or ethylthio), $C_1$-$C_4$ alkylsulphinyl (e.g. methylsulphinyl or ethylsulphinyl), $C_1$-$C_4$ alkylsulphonyl (e.g. methylsulphonyl or ethylsulphonyl), $C_1$-$C_4$ alkylcarbonyl (e.g. methylcarbonyl or ethylcarbonyl), $C_1$-$C_4$ alkylcarbonyloxy (e.g. methylcarbonyloxy), $C_1$-$C_4$ alkoxycarbonyl (e.g. methoxycarbonyl), amino, —CON($R^{18}$)$_2$, $C_1$-$C_4$ alkylamino (e.g. methylamino or ethylamino), di-($C_1$-$C_4$ alkyl)amino (e.g. dimethylamino), $C_3$-$C_5$ cycloalkyl, $C_3$-$C_5$ cycloalkyloxy and $C_3$-$C_5$ cycloalkylmethyl.

In another embodiment of the invention, $R^{14}$ represents a 6-, 7-, 8-, 9- or 10-membered, particularly 6-membered, aromatic or heteroaromatic (particularly a nitrogen-containing heteroaromatic) ring system, the ring system itself being optionally substituted by at least one substituent (e.g. one, two, three or four substituents independently) selected from halogen (e.g. fluorine, chlorine or bromine), cyano, $C_1$-$C_4$ alkyl (e.g. methyl or ethyl), $C_1$-$C_2$ haloalkyl (e.g. trifluoromethyl), $C_1$-$C_4$ alkoxy (e.g. methoxy or ethoxy) and $C_1$-$C_2$ haloalkoxy (e.g. trifluoromethoxy).

In still another embodiment of the invention, $R^{14}$ represents a 6-, 7-, 8-, 9- or 10-membered, particularly 6-membered, aromatic or heteroaromatic (particularly a nitrogen-containing heteroaromatic) ring system, the ring system itself being optionally substituted by at least one substituent (preferably up to three, most preferably one or two, substituents independently) selected from halogen (e.g. fluorine, chlorine or bromine), cyano, methyl, trifluoromethyl, methoxy and trifluoromethoxy.

Each $R^{18}$ independently represents a hydrogen atom or a $C_1$-$C_6$, or $C_1$-$C_4$, or $C_1$-$C_2$ alkyl, particularly methyl, group.

In a preferred embodiment of the invention, compounds of formula (I) are those in which:
W, X, Y and Z each independently represent a nitrogen atom or a moiety NH or CH, with the proviso that W, X, Y and Z do not each simultaneously represent a moiety CH;
m is 2 or 3;
each $R^1$ independently represents halogen, $C_1$-$C_6$ haloalkyl or $C_1$-$C_6$ alkyl;
n is 0 or 1;
$R^2$ represents cyano, hydroxyl, $C_1$-$C_6$ alkyl, $C_1$-$C_6$ alkoxy, $C_1$-$C_6$ alkoxycarbonyl, or $C_1$-$C_6$ alkoxy$C_1$-$C_6$ alkyl;
$R^3$ represents an oxygen atom, or a group C=O, $NR^5$ or $CR^6R^7$;
$R^5$ represents a hydrogen atom or a $C_1$-$C_6$ alkyl group;
$R^6$ and $R^7$ each independently represent a hydrogen or halogen atom or a cyano, hydroxyl, $C_1$-$C_6$ alkyl, $C_1$-$C_6$ haloalkyl, $C_1$-$C_6$ alkoxy, $C_1$-$C_6$ hydroxyalkyl or $C_1$-$C_6$ alkoxy$C_1$-$C_6$ alkyl group; and
$R^4$ represents a 6- to 10-membered aromatic or heteroaromatic ring system, the ring system itself being optionally substituted by at least one substituent selected from halogen, cyano, $C_1$-$C_6$ alkyl, $C_1$-$C_6$ haloalkyl, $C_1$-$C_6$ alkoxy and $C_1$-$C_6$ haloalkoxy.

In another preferred embodiment of the invention, compounds of formula (I) are those in which:
W, X, Y and Z each independently represent a nitrogen atom or a moiety NH or CH, with the proviso that W, X, Y and Z do not each simultaneously represent a moiety CH;
m is 2 or 3;
each $R^1$ independently represents halogen, $C_1$-$C_6$ haloalkyl or $C_1$-$C_6$ alkyl;
n is 0 Or 1;
$R^2$ represents cyano, hydroxyl, $C_1$-$C_6$ alkyl, $C_1$-$C_6$ alkoxy, $C_1$-$C_6$ alkoxycarbonyl, or $C_1$-$C_6$ alkoxy$C_1$-$C_6$ alkyl;
$R^3$ represents an oxygen atom, or a group C=O, $NR^5$ or $CR^6R^7$;
$R^5$, $R^6$ and $R^7$ each independently represent a hydrogen atom or a $C_1$-$C_6$ alkyl group; and
$R^4$ represents a 6- to 10-membered aromatic or heteroaromatic ring system, the ring system itself being optionally substituted by at least one substituent selected from halogen, cyano, $C_1$-$C_6$ alkyl, $C_1$-$C_6$ haloalkyl, $C_1$-$C_6$ alkoxy and $C_1$-$C_6$ haloalkoxy.

In a preferred embodiment of the invention, compounds of formula (Ia) are those in which:
$W^1$, $X^1$, $Y^1$ and $Z^1$ each independently represent a nitrogen atom or a moiety NH or CH, with the proviso that $W^1$, $X^1$, $Y^1$ and $Z^1$ do not each simultaneously represent a moiety CH;
p is 2 or 3;
each $R^1$ independently represents halogen, $C_1$-$C_6$ haloalkyl or $C_1$-$C_6$ alkyl;
q is 0 or 1;
each $R^{12}$ represents cyano, hydroxyl, $C_1$-$C_6$ alkyl, $C_1$-$C_6$ alkoxy, $C_1$-$C_6$ alkoxycarbonyl, or $C_1$-$C_6$ alkoxy$C_1$-$C_6$ alkyl;
$R^{13}$ represents an oxygen atom or a group C=O, $NR^{15}$ or $CR^{16}R^{17}$, with the provisos that (i) when $R^{13}$ represents CO or NH and ring A represents pyrazol-4-yl or imidazol-4-yl, then p must be 3 and $R^{14}$ represents a substituted 6- to 10-membered aromatic or heteroaromatic ring system, and (ii) when $R^{13}$ represents $CH_2$ and ring A represents pyrazol-4-yl or imidazol-4-yl, then either p is 3, or, p is 2 and q is at least 1;
$R^{15}$, $R^{16}$ and $R^{17}$ each independently represent a hydrogen atom or a $C_1$-$C_6$ alkyl group; and
$R^{14}$ represents a 6- to 10-membered aromatic or heteroaromatic ring system, the ring system itself being optionally substituted by at least one substituent selected from halogen, cyano, $C_1$-$C_6$ alkyl, $C_1$-$C_6$ haloalkyl, $C_1$-$C_6$ alkoxy and $C_1$-$C_6$ haloalkoxy; but excluding compounds numbered 1) to 5), 7) to 9), 11) and 13) to 25) as hereinbefore defined.

In another preferred embodiment of the invention, compounds of formula (Ia) are those in which:
$W^1$, $X^1$, $Y^1$ and $Z^1$ each independently represent a nitrogen atom or a moiety NH or CH, with the proviso that $W^1$, $X^1$, $Y^1$ and $Z^1$ do not each simultaneously represent a moiety CH;
p is 2 or 3;
each $R^1$ independently represents halogen, $C_1$-$C_6$ haloalkyl or $C_1$-$C_6$ alkyl;
q is 0 or 1;
each $R^{12}$ represents cyano, hydroxyl, $C_1$-$C_6$ alkyl, $C_1$-$C_6$ alkoxy, $C_1$-$C_6$ alkoxycarbonyl, or $C_1$-$C_6$ alkoxy$C_1$-$C_6$ alkyl;
$R^{13}$ represents an oxygen atom or a group C=O, $NR^{15}$ or $CR^{16}R^{17}$, with the provisos that (i) when $R^{13}$ represents CO or NH and ring A represents pyrazol-4-yl or imidazol-4-yl, then p must be 3 and $R^{14}$ represents a substituted 6- to 10-membered aromatic or heteroaromatic ring system, and (ii) when $R^{13}$ represents $CH_2$ and ring A represents pyrazol-4-yl or imidazol-4-yl, then either p is 3, or, p is 2 and q is at least 1;

$R^{15}$ represents a hydrogen atom or a $C_1$-$C_6$ alkyl group;

$R^{16}$ and $R^{17}$ each independently represent a hydrogen or halogen atom or a cyano, hydroxyl, $C_1$-$C_6$ alkyl, $C_1$-$C_6$ haloalkyl, $C_1$-$C_6$ alkoxy, $C_1$-$C_6$ hydroxyalkyl or $C_1$-$C_6$ alkoxy$C_1$-$C_6$ alkyl group; and $R^{14}$ represents a 6- to 10-membered aromatic or heteroaromatic ring system, the ring system itself being optionally substituted by at least one substituent selected from halogen, cyano, $C_1$-$C_6$ alkyl, $C_1$-$C_6$ haloalkyl, $C_1$-$C_6$ alkoxy and $C_1$-$C_6$ haloalkoxy; but excluding compounds numbered 1) to 5), 7) to 9), 11) and 13) to 25) as hereinbefore defined.

In still another preferred embodiment of the invention, compounds of formula (Ia) are those in which:

$W^1$, $X^1$, $Y^1$ and $Z^1$ each independently represent a nitrogen atom or a moiety NH or CH, with the proviso that $W^1$, $X^1$, $Y^1$ and $Z^1$ do not each simultaneously represent a moiety CH;

p is 2 or 3;

each $R^1$ independently represents halogen, $C_1$-$C_6$ haloalkyl or $C_1$-$C_6$ alkyl;

q is 0 or 1;

each $R^{12}$ represents cyano, hydroxyl, $C_1$-$C_6$ alkyl, $C_1$-$C_6$ alkoxy, $C_1$-$C_6$ alkoxycarbonyl, or $C_1$-$C_6$ alkoxy$C_1$-$C_6$ alkyl;

$R^{13}$ represents an oxygen atom or a group $NR^{15}$ or $CR^{16}R^{17}$, with the provisos that (i) when $R^{13}$ represents NH and ring A represents pyrazol-4-yl or imidazol-4-yl, then p must be 3 and $R^{14}$ represents a substituted 6- to 10-membered aromatic or heteroaromatic ring system, and (ii) when $R^{13}$ represents $CH_2$ and ring A represents pyrazol-4-yl or imidazol-4-yl, then either p is 3, or, p is 2 and q is at least 1;

$R^{15}$ represents a hydrogen atom or a $C_1$-$C_6$ alkyl group;

$R^{16}$ and $R^{17}$ each independently represent a hydrogen or halogen atom or a cyano, hydroxyl, $C_1$-$C_6$ alkyl, $C_1$-$C_6$ haloalkyl, $C_1$-$C_6$ alkoxy, $C_1$-$C_6$ hydroxyalkyl or $C_1$-$C_6$ alkoxy$C_1$-$C_6$ alkyl group; and $R^{14}$ represents a 6- to 10-membered aromatic or heteroaromatic ring system, the ring system itself being optionally substituted by at least one substituent selected from halogen, cyano, $C_1$-$C_6$ alkyl, $C_1$-$C_6$ haloalkyl, $C_1$-$C_6$ alkoxy and $C_1$-$C_6$ haloalkoxy; but excluding compounds numbered 1) to 5), 7), 9), 11), 13) to 23) and 25) as hereinbefore defined.

Examples of novel compounds of formula (Ia) according to the invention include:

4-(3,4-Dichlorophenoxy)-1-((1,3,5-trimethyl-1H-pyrazol-4-yl)sulfonyl)piperidine,
4-(3,4-Dichlorophenoxy)-1-[(3,5-dimethyl-1H-pyrazol-4-yl)sulfonyl]piperidine,
4-[4-(Trifluoromethoxy)phenoxy]-1-[(1,3,5-trimethyl-1H-pyrazol-4-yl)sulfonyl]piperidine,
4-(4-Methylphenoxy)-1-[(1,3,5-trimethyl-1H-pyrazol-4-yl)sulfonyl]piperidine,
4-(4-Chlorophenoxy)-1-[(1,3,5-trimethyl-1H-pyrazol-4-yl)sulfonyl]piperidine,
4-(3-Chlorophenoxy)-1-[(1,3,5-trimethyl-1H-pyrazol-4-yl)sulfonyl]piperidine,
4-({1-[(1,3,5-Trimethyl-1H-pyrazol-4-yl)sulfonyl]piperidin-4-yl}oxy)benzonitrile,
4-(4-Chlorophenoxy)-1-[(3,5-dimethyl-1H-pyrazol-4-yl)sulfonyl]piperidine,
1-[(1-Ethyl-3,5-dimethyl-1H-pyrazol-4-yl)sulfonyl]-4-(4-methylphenoxy)piperidine,
1-{[1,5-Dimethyl-3-(trifluoromethyl)-1H-pyrazol-4-yl]sulfonyl}-4-(4-methylphenoxy)piperidine,
1-[(5-Chloro-1,3-dimethyl-1H-pyrazol-4-yl)sulfonyl]-4-(4-methylphenoxy)piperidine,
4-[4-(Trifluoromethyl)phenoxy]-1-[(1,3,5-trimethyl-1H-pyrazol-4-yl)sulfonyl]piperidine,
4-(2,4-Dichlorophenoxy)-1-[(1,3,5-trimethyl-1H-pyrazol-4-yl)sulfonyl]piperidine,
4-(4-Bromo-2-fluorophenoxy)-1-[(1,3,5-trimethyl-1H-pyrazol-4-yl)sulfonyl]piperidine,
1-[(5-Chloro-1,3-dimethyl-1H-pyrazol-4-yl)sulfonyl]-4-(4-chlorophenoxy)piperidine,
4-(4-Chlorophenoxy)-1-{[1,5-dimethyl-3-(trifluoromethyl)-1H-pyrazol-4-yl]sulfonyl}piperidine,
4-(3-Methoxyphenoxy)-1-[(1,3,5-trimethyl-1H-pyrazol-4-yl)sulfonyl]piperidine,
4-(4-Methoxyphenoxy)-1-[(1,3,5-trimethyl-1H-pyrazol-4-yl)sulfonyl]piperidine,
4-Phenoxy-1-[(1,3,5-trimethyl-1H-pyrazol-4-yl)sulfonyl]piperidine,
4-(4-Fluorophenoxy)-1-[(1,3,5-trimethyl-1H-pyrazol-4-yl)sulfonyl]piperidine,
4-(4-Chlorophenoxy)-3-methyl-1-[(1,3,5-trimethyl-1H-pyrazol-4-yl)sulfonyl]piperidine,
4-(2,4-Dichlorophenoxy)-1-[(3,5-dimethyl-1H-pyrazol-4-yl)sulfonyl]piperidine,
4-(Naphthalen-2-yloxy)-1-[(1,3,5-trimethyl-1H-pyrazol-4-yl)sulfonyl]piperidine,
4-(4-Chlorophenoxy)-2-methyl-1-[(1,3,5-trimethyl-1H-pyrazol-4-yl)sulfonyl]piperidine,
1-[(5-Chloro-1,3-dimethyl-1H-pyrazol-4-yl)sulfonyl]-4-(2,4-dichlorophenoxy)piperidine,
4-(2,4-Dichlorophenoxy)-1-{[1,3-dimethyl-5-(trifluoromethyl)-1H-pyrazol-4-yl]sulfonyl}piperidine,
4-(2,4-Dichlorophenoxy)-1-[(1,3-dimethyl-1H-pyrazol-4-yl)sulfonyl]piperidine,
4-(2,4-Dichlorophenoxy)-1-[(3,5-diethyl-1-methyl-1H-pyrazol-4-yl)sulfonyl]piperidine,
4-(2,4-Dichlorophenoxy)-1-{[1-(difluoromethyl)-3,5-dimethyl-1H-pyrazol-4-yl]sulfonyl}piperidine,
4-(4-Chloro-2-fluorophenoxy)-1-(trimethyl-1H-pyrazole-4-sulfonyl)piperidine,
5-Chloro-2-{[1-(trimethyl-1H-pyrazole-4-sulfonyl)piperidin-4-yl]oxy}benzonitrile,
1-[(3,5-Dimethyl-1H-pyrazol-4-yl)sulfonyl]-4-[4-(trifluoromethoxy)phenoxy]piperidine,
1-[(3,5-Dimethyl-1H-pyrazol-4-yl)sulfonyl]-4-(naphthalen-2-yloxy)piperidine,
5-Chloro-2-{[1-(3,5-dimethyl-1H-pyrazole-4-sulfonyl)piperidin-4-yl]oxy}benzonitrile,
4-(4-Chloro-2-fluorophenoxy)-1-(3,5-dimethyl-1H-pyrazole-4-sulfonyl)piperidine,
4-(2,4-Dichlorophenoxy)-1-(1,4-dimethyl-1H-pyrazole-5-sulfonyl)piperidine,
4-(4-Chlorophenoxy)-1-(1,4-dimethyl-1H-pyrazole-5-sulfonyl)piperidine,
1-(3,5-Dimethyl-1H-pyrazole-4-sulfonyl)-4-(2,6-dimethylphenoxy)piperidine,
4-[4-Chloro-2-(trifluoromethyl)phenoxy]-1-(trimethyl-1H-pyrazole-4-sulfonyl)piperidine,
4-[4-Chloro-2-(trifluoromethyl)phenoxy]-1-(3,5-dimethyl-1H-pyrazole-4-sulfonyl)piperidine, 1-(3,5-Dimethyl-1H-pyrazole-4-sulfonyl)-4-(3-fluoro-4-methoxyphenoxy)piperidine,
4-(3,5-Difluoro-4-methoxyphenoxy)-1-(3,5-dimethyl-1H-pyrazole-4-sulfonyl)piperidine,
4-(3-Fluoro-4-methoxyphenoxy)-1-(trimethyl-1H-pyrazole-4-sulfonyl)piperidine,
4-(3,5-Difluoro-4-methoxyphenoxy)-1-(trimethyl-1H-pyrazole-4-sulfonyl)piperidine,
4-(4-Chloro-3-fluorophenoxy)-1-(trimethyl-1H-pyrazole-4-sulfonyl)piperidine,
4-(4-Chloro-2,6-difluorophenoxy)-1-(trimethyl-1H-pyrazole-4-sulfonyl)piperidine,
4-(4-Chloro-3-fluorophenoxy)-1-(3,5-dimethyl-1H-pyrazole-4-sulfonyl)piperidine,
5-Chloro-2-((1-((1,3,5-trimethyl-1H-pyrazol-4-yl)sulfonyl)piperidin-4-yl)oxy)pyridine,
(4-Chlorophenyl)(1-((1,3,5-trimethyl-1H-pyrazol-4-yl)sulfonyl)piperidin-4-yl)methanone,
(3,4-Dichlorophenyl)(1-((1,3,5-trimethyl-1H-pyrazol-4-yl)sulfonyl)piperidin-4-yl)methanone,
N-(4-Chlorophenyl)-1-((1,3,5-trimethyl-1H-pyrazol-4-yl)sulfonyl)piperidin-4-amine,
N-(3,4-Dichlorophenyl)-1-((1,3,5-trimethyl-1H-pyrazol-4-yl)sulfonyl)piperidin-4-amine,
4-Chloro-N-{[1-(trimethyl-1H-pyrazole-4-sulfonyl)piperidin-4-yl]methyl}aniline,
3,4-Dichloro-N-{[1-(trimethyl-1H-pyrazole-4-sulfonyl)piperidin-4-yl]methyl}aniline,
4-(4-Chlorobenzyl)-1-((1,3,5-trimethyl-1H-pyrazol-4-yl)sulfonyl)piperidine,
4-(3,4-Dichlorobenzyl)-1-((1,3,5-trimethyl-1H-pyrazol-4-yl)sulfonyl)piperidine,
4-(4-Chlorobenzyl)-1-((1,3,5-trimethyl-1H-pyrazol-4-yl)sulfonyl)piperidin-4-ol,
4-(4-Chlorobenzyl)-4-methoxy-1-((1,3,5-trimethyl-1H-pyrazol-4-yl)sulfonyl)piperidine,
4-(2,4-Dichlorobenzyl)-1-((1,3,5-trimethyl-1H-pyrazol-4-yl)sulfonyl)piperidin-4-ol,
4-(4-Chlorobenzyl)-4-(methoxymethyl)-1-((1,3,5-trimethyl-1H-pyrazol-4-yl)sulfonyl)piperidine,
Ethyl 4-(4-chlorobenzyl)-1-((1,3,5-trimethyl-1H-pyrazol-4-yl)sulfonyl)piperidine-4-carboxylate,
Ethyl 4-(4-bromobenzyl)-1-((3,5-dimethyl-1H-pyrazol-4-yl)sulfonyl)piperidine-4-carboxylate,
Ethyl 4-(4-bromobenzyl)-1-((1,3,5-trimethyl-1H-pyrazol-4-yl)sulfonyl)piperidine-4-carboxylate,
4-(4-Chlorobenzyl)-1-((3,5-dimethyl-1H-pyrazol-4-yl)sulfonyl)piperidine-4-carbonitrile,
4-(2,4-Dichlorobenzyl)-1-((3,5-dimethyl-1H-pyrazol-4-yl)sulfonyl)piperidine-4-carbonitrile,
1-((5-Chloro-1,3-dimethyl-1H-pyrazol-4-yl)sulfonyl)-4-(4 chlorobenzyl)piperidine,
4-(3,4-Dichlorobenzyl)-1-((1,3,5-trimethyl-1H-pyrazol-4-yl)sulfonyl)piperidin-4-ol,
4-(3,4-Dichlorobenzyl)-1-((3,5-dimethyl-1H-pyrazol-4-yl)sulfonyl)piperidin-4-ol,
4-(4-Chloro-3-fluorobenzyl)-1-((1,3,5-trimethyl-1H-pyrazol-4-yl)sulfonyl)piperidine,
4-(4-Chloro-2-methoxyphenoxy)-1-((3,5-dimethyl-1H-pyrazol-4-yl)sulfonyl)piperidine,
4-(4-Chloro-2-methoxyphenoxy)-1-((1,3,5-trimethyl-1H-pyrazol-4-yl)sulfonyl)piperidine,
4-(4-Chloro-2-fluorobenzyl)-1-((3,5-dimethyl-1H-pyrazol-4-yl)sulfonyl)piperidin-4-ol,
1-((3,5-Dimethyl-1H-pyrazol-4-yl)sulfonyl)-4-(2-fluorophenoxy)piperidine,
5-Chloro-3-fluoro-2-((1-((1,3,5-trimethyl-1H-pyrazol-4-yl)sulfonyl)piperidin-4-yl)oxy)pyridine,
4-(4-Chloro-2-methoxybenzyl)-1-((1,3,5-trimethyl-1H-pyrazol-4-yl)sulfonyl)piperidine,
4-(4-Chloro-2-fluorobenzyl)-1-((3,5-dimethyl-1H-pyrazol-4-yl)sulfonyl)-4-fluoropiperidine,
4-(4-Chloro-2-fluorobenzyl)-4-fluoro-1-((1,3,5-trimethyl-1H-pyrazol-4-yl)sulfonyl)piperidine,
4-(4-Chloro-2-fluorobenzyl)-1-((1,3,5-trimethyl-1H-pyrazol-4-yl)sulfonyl)piperidine,
5-Chloro-3-methoxy-2-((1-((1,3,5-trimethyl-1H-pyrazol-4-yl)sulfonyl)piperidin-4-yl)oxy)pyridine,
5-Chloro-2-((1-((3,5-dimethyl-1H-pyrazol-4-yl)sulfonyl)piperidin-4-yl)oxy)-3-methoxypyridine,
4-(4-Chloro-2-methoxybenzyl)-1-((3,5-dimethyl-1H-pyrazol-4-yl)sulfonyl)-4-methoxypiperidine,
4-(4-Chloro-2-methoxybenzyl)-4-methoxy-1-((1,3,5-trimethyl-1H-pyrazol-4-yl)sulfonyl)piperidine,
4-(4-Chloro-2-methoxybenzyl)-1-((1,3,5-trimethyl-1H-pyrazol-4-yl)sulfonyl)piperidin-4-ol,
4-(4-Chloro-2-methoxybenzyl)-1-((3,5-dimethyl-1H-pyrazol-4-yl)sulfonyl)piperidin-4-ol,
4-(4-Chloro-2-methoxybenzyl)-1-((3,5-dimethyl-1H-pyrazol-4-yl)sulfonyl)-4-fluoropiperidine,
4-(4-Chloro-2-methoxybenzyl)-4-fluoro-1-((1,3,5-trimethyl-1H-pyrazol-4-yl)sulfonyl)piperidine,
2-(4-Chloro-2-fluorophenyl)-2-(1-((3,5-dimethyl-1H-pyrazol-4-yl)sulfonyl)piperidin-4-yl)acetonitrile,
2-(4-Chlorophenyl)-2-(1-((3,5-dimethyl-1H-pyrazol-4-yl)sulfonyl)piperidin-4-yl)acetonitrile,
(4-Chlorophenyl)(1-((3,5-dimethyl-1H-pyrazol-4-yl)sulfonyl)piperidin-4-yl)methanol,
(4-Chlorophenyl)(1-((1,3,5-trimethyl-1H-pyrazol-4-yl)sulfonyl)piperidin-4-yl)methanol,
4-((4-Chlorophenyl)(methoxy)methyl)-1-((3,5-dimethyl-1H-pyrazol-4-yl)sulfonyl)piperidine,
4-((4-Chlorophenyl)(methoxy)methyl)-1-((1,3,5-trimethyl-1H-pyrazol-4-yl)sulfonyl)piperidine,
2-(4-Chlorophenyl)-2-(1-((3,5-dimethyl-1H-pyrazol-4-yl)sulfonyl)piperidin-4-yl)ethanol,
1-(4-Chlorophenyl)-1-(1-((3,5-dimethyl-1H-pyrazol-4-yl)sulfonyl)piperidin-4-yl)ethanol,
4-(1-(4-Chlorophenyl)ethyl)-1-((3,5-dimethyl-1H-pyrazol-4-yl)sulfonyl)piperidine,
4-((4-Chlorophenyl)(ethoxy)methyl)-1-((3,5-dimethyl-1H-pyrazol-4-yl)sulfonyl)piperidine,
4-((4-Chlorophenyl)fluoromethyl)-1-((3,5-dimethyl-1H-pyrazol-4-yl)sulfonyl)piperidine,
4-(4-Chlorobenzyl)-1-((3,5-dimethyl-1H-pyrazol-4-yl)sulfonyl)piperidin-4-ol,
4-(1-(4-Chlorophenyl)-2-methoxyethyl)-1-((3,5-dimethyl-1H-pyrazol-4-yl)sulfonyl)piperidine,
1-((3,5-Dimethyl-1H-pyrazol-4-yl)sulfonyl)-4-(methoxy(phenyl)methyl)piperidine,
4-(1-(4-Chlorophenyl)-2,2-difluoroethyl)-1-((3,5-dimethyl-1H-pyrazol-4-yl)sulfonyl)piperidine, and pharmaceutically acceptable salts of any one thereof.

It should be noted that each of the chemical compounds listed above represents a particular and independent aspect of the invention.

Compounds of formula (I) and pharmaceutically acceptable salts thereof as defined above may be prepared by a process comprising (i) reacting a compound of formula

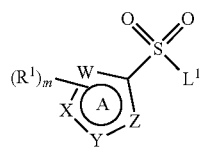

(II)

wherein L¹ represents a leaving group (e.g. a halogen atom) and m, W, X, Y, Z and are as defined in formula (I), with a compound of formula

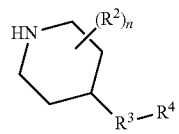

(III)

or a suitable salt (e.g. a hydrochloride salt) thereof, wherein n, R², R³ and R⁴ are as defined in formula (I); or (ii) reacting a compound of formula

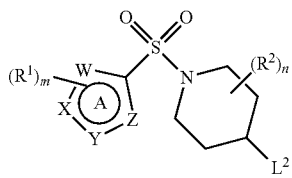

(IV)

wherein L2 represents a leaving group (e.g. mesylate) and m, n, W, X, Y, Z, R¹ and R² are as defined in formula (I), with a compound of formula $L^3$-$R^3$-$R^4$ (V) wherein $L^3$ represents a leaving group (e.g. mesylate) and R³ and R⁴ are as defined in formula (I);

and optionally thereafter carrying out one or more of the following procedures:

converting a compound of formula (I) into another compound of formula (I)

removing any protecting groups forming a pharmaceutically acceptable salt.

Process (i) above may conveniently be carried out in the presence of an organic solvent such as dichloromethane, acetonitrile or tetrahydrofuran and a suitable base such as triethylamine, pyridine or diisopropylethylamine, at a temperature in the range from 20° C. to 40° C., e.g. at ambient temperature (20° C.).

Process (ii) above may conveniently be carried out as for process (i) but at temperatures in the range from 20 to 80° C.

It will be appreciated that compounds of formula (Ia) may be prepared by processes analogous to those described above for the preparation of compounds of formula (I), that is, by a process comprising (i) reacting a compound of formula

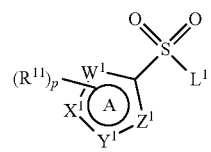

(IIa)

wherein L¹, p, W¹, X¹, Y¹, Z¹ and R¹¹ have the meanings defined above, with a compound of formula

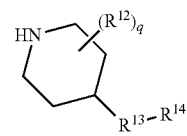

(IIIa)

or a suitable salt thereof, wherein q, R¹², R¹³ and R¹⁴ have the meanings defined above; or (ii) reacting a compound of formula

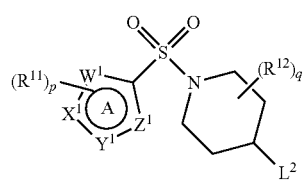

(IVa)

wherein L², p, q, W¹, X¹, Y¹, Z¹, R¹ and R¹¹ and R¹² have the meanings define above, with a compound of formula $L^3$-$R^{13}$-$R^{14}$ (Va) wherein $L^3$, R¹³ and R¹⁴ have the meanings defined above.

Compounds of formula (II) in which L¹ represents a halogen atom may be prepared by reacting a compound of formula

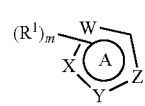

(VI)

wherein m, W, X, Y, Z and R¹ are as defined in formula (I), with sulphur dioxide in the present of an organometallic reagent (e.g. an organolithium reagent such as n-butyl lithium), followed by reaction with a halogenating agent, e.g. N-chlorosuccinimide.

The first step of the process is conveniently carried out in the presence of an organic polar solvent such as ether, chloroform or dichloromethane under a nitrogen atmosphere at low temperature, e.g. from 0° C. to −70° C. The second step of the process may be carried out using a biphasic solvent mixture, e.g. dichloromethane/water mixture, at ambient temperature (20° C.).

Compounds of formula (IIa) may be prepared in an analogous manner to the compounds of formula (II).

Compounds of formula (III) in which R³ represents an oxygen atom may be prepared by reacting a compound of formula

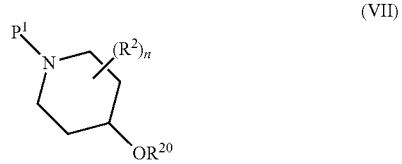

(VII)

wherein P¹ represents a nitrogen-protecting group (e.g. tert-butoxy carbonyl group), R²⁰ represents a hydrogen atom or a leaving group (e.g. —SO₂Me) and n and R² are as defined in formula (I), with a compound of formula (VIII), HO—R⁴, wherein R⁴ is as defined in formula (I), in the presence of a coupling agent (e.g. diisopropyl azodicarboxylate).

Compounds of formula (III) in which R³ represents a sulphur atom may be prepared as described in European Patent Application Publication No. EP 1 227 090 (Kato et al).

Compounds of formula (III) in which R³ represents C═O may be prepared by processes analogous to those described by Orjales et al, *J. Med. Chem.*, 2003, 46, 5512-5532 and Zhudu Tu et al, *J. Med. Chem.*, 2009, 52, 1358-1369.

Compounds of formula (III) in which R³ represents NR⁵ may be prepared as described in International Patent Application Publication No. WO 01/62757 (Hansen et al).

Compounds of formula (III) in which R³ represents CR⁶R⁷ may be prepared as described in European Patent Application Publication No. EP 1 227 090 (Kato et al).

Compounds of formula (IIIa) may be prepared by processes analogous to those used to prepare compounds of formula (III).

Compounds of formulae (IV), (IVa), (V), (Va), (VI), (VII) and (VIII) are either commercially available, are well known in the literature or may be prepared using known techniques.

It will be appreciated by those skilled in the art that in the above processes certain functional groups such as phenol, hydroxyl or amino groups in the reagents may need to be protected by protecting groups. Thus, the preparation of compounds of formula (I) or (Ia) may involve, at an appropriate stage, the removal of one or more protecting groups.

The protection and deprotection of functional groups is described in 'Protective Groups in Organic Chemistry', edited by J. W. F. McOmie, Plenum Press (1973) and 'Protective Groups in Organic Synthesis', 3rd edition, T. W. Greene and P. G. M. Wuts, Wiley-Interscience (1999).

The compounds of formula (I) or (Ia) above may be converted to a pharmaceutically acceptable salt thereof, preferably an acid addition salt such as a hydrochloride, hydrobromide, benzenesulphonate (besylate), saccharin (e.g. monosaccharin), trifluoroacetate, sulphate, nitrate, phosphate, acetate, fumarate, maleate, tartrate, lactate, citrate, pyruvate, succinate, valerate, propanoate, butanoate, malonate, oxalate, 1-hydroxy-2-napthoate (xinafoate), methanesulphonate or p-toluenesulphonate salt.

In one aspect of the invention, compounds of formula (I) or (Ia) defined above may bear one or more radiolabels. Such radiolabels may be introduced by using radiolabel-containing reagents in the synthesis of the compounds of formula (I) or (Ia), or may be introduced by coupling the compounds of formula (I) or (Ia) to chelating moieties capable of binding to a radioactive metal atom. Such radiolabeled versions of the compounds may be used, for example, in diagnostic imaging studies.

Compounds of formula (I) or (Ia) and their salts may be in the form of hydrates or solvates which form an aspect of the present invention. Such solvates may be formed with common organic solvents, including but not limited to, alcoholic solvents e.g. methanol, ethanol or isopropanol.

Compounds of formula (I) or (Ia) above are capable of existing in stereoisomeric forms. It will be understood that the invention encompasses the use of all geometric and optical isomers (including atropisomers) of the compounds of formula (I) or (Ia) and mixtures thereof including racemates. The use of tautomers and mixtures thereof also form an aspect of the present invention. Enantiomerically pure forms are particularly desired.

The compounds of formula (I) or (Ia) and their pharmaceutically acceptable salts have activity as pharmaceuticals, in particular as prokineticin receptor modulators, and thus may be used in the treatment of schizophrenia and other psychotic disorders (e.g., psychotic disorder, psychosis), dementia and other cognitive disorders, anxiety disorders (e.g., generalized anxiety disorder), mood disorders (e.g., depressive disorders, major depressive disorders, bipolar disorders including bipolar I and II, bipolar mania, bipolar depression), sleep disorders, disorders usually first diagnosed in infancy, childhood, or adolescence (e.g., attention-deficit disorder and disruptive behaviour disorders), pain (e.g. neuropathic pain), inflammatory conditions and neurodegenerative disorders (e.g. Parkinson's or Alzheimer's disease).

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disorder or condition in question. Persons at risk of developing a particular disorder or condition generally include those having a family history of the disorder or condition, or those who have been identified by genetic testing or screening to be particularly susceptible to developing the disorder or condition or those in the prodromal phase of a disorder.

In particular, the compounds of formula (I) or (Ia) and their pharmaceutically acceptable salts as defined above may be used in the treatment of the positive symptoms of schizophrenia, schizophreniform disorder or schizoaffective disorder (e.g. voices or hallucinations), cognitive disorders (such as dementia and impaired learning) and also pain (such as neuropathic pain).

The invention also provides a method of treating at least one symptom or condition associated with schizophrenia, schizophreniform disorder, schizoaffective disorder and other psychotic disorders (e.g., psychotic disorder, psychosis), dementia and other cognitive disorders, anxiety disorders (e.g., generalized anxiety disorder), mood disorders (e.g., depressive disorders, major depressive disorders, bipolar disorders including bipolar I and II, bipolar mania, bipolar depression), sleep disorders, disorders usually first diagnosed in infancy, childhood, or adolescence (e.g., attention-deficit disorder, autistic spectrum disorders and disruptive behaviour disorders), pain (e.g. neuropathic pain) and neurodegenerative disorders (e.g. Parkinson's or Alzheimer's disease) which comprises administering to a patient in need thereof a therapeutically effective amount of a compound of formula (I) or (Ia) or a pharmaceutically acceptable salt thereof as hereinbefore defined.

Such symptoms and conditions include, but are not limited to, anxiety, agitation, hostility, panic, an eating disorder, an affective symptom, a mood symptom, a negative and positive psychotic symptom commonly associated with psychosis and neurodegenerative disorder.

For the above-mentioned therapeutic uses the dosage administered will, of course, vary with the compound employed, the mode of administration, the treatment desired and the disorder indicated. For example, the daily dosage of a compound according to the invention (i.e. a compound of formula (I) or (Ia) or a pharmaceutically acceptable salt thereof), if inhaled, may be in the range from 0.05 micrograms per kilogram body weight (μg/kg) to 100 micrograms per kilogram body weight (μg/kg). Alternatively, if the compound is administered orally, then the daily dosage of the compound of the invention may be in the range from 0.01 micrograms per kilogram body weight (μg/kg) to 100 milligrams per kilogram body weight (mg/kg).

The compounds of formula (I) or (Ia) and pharmaceutically acceptable salts thereof may be used on their own but will generally be administered in the form of a pharmaceutical composition in which the formula (I) or (Ia) compound/salt (active ingredient) is in association with a pharmaceutically acceptable adjuvant, diluent or carrier.

Therefore the present invention further provides a pharmaceutical composition comprising a compound of formula (I) or (Ia) or a pharmaceutically acceptable salt thereof as hereinbefore defined, in association with a pharmaceutically acceptable adjuvant, diluent or carrier. The invention still further provides a process for the preparation of a pharmaceutical composition of the invention which comprises mixing a compound of formula (I) or (Ia) or a pharmaceutically acceptable salt thereof as hereinbefore defined with a pharmaceutically acceptable adjuvant, diluent or carrier.

Conventional procedures for the selection and preparation of suitable pharmaceutical formulations are described in, for example, "Pharmaceuticals—The Science of Dosage Form Designs", M. E. Aulton, Churchill Livingstone, 1988.

Pharmaceutically acceptable adjuvants, diluents or carriers that may be used in the pharmaceutical compositions of the invention are those conventionally employed in the field of pharmaceutical formulation, and include, but are not limited to, sugars, sugar alcohols, starches, ion exchangers, alumina, aluminium stearate, lecithin, serum proteins, such as human serum albumin, buffer substances such as phosphates, glycerine, sorbic acid, potassium sorbate, partial glyceride mixtures of saturated vegetable fatty acids, water, salts or electrolytes, such as protamine sulphate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of the present invention may be administered orally, parenterally, by inhalation spray, rectally, nasally, buccally, vaginally or via an implanted reservoir. Oral administration is preferred. The pharmaceutical compositions of the invention may contain any conventional non-toxic pharmaceutically acceptable adjuvants, diluents or carriers. The term parenteral as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. The suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable diluents and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant such as that described in Ph. Helv. or a similar alcohol.

The pharmaceutical compositions of this invention may be orally administered in any orally acceptable dosage form including, but not limited to, capsules, tablets, powders, granules, and aqueous suspensions and solutions. These dosage forms are prepared according to techniques well-known in the art of pharmaceutical formulation. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavouring and/or colouring agents may be added.

The pharmaceutical compositions of the invention may also be administered in the form of suppositories for rectal administration. These compositions can be prepared by mixing the active ingredient with a suitable non-irritating excipient which is solid at room temperature but liquid at the rectal temperature and therefore will melt in the rectum to release the active ingredient. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilising or dispersing agents known in the art.

Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The compounds of formula (I) or (Ia) and pharmaceutically acceptable salts thereof as defined above may also be administered in conjunction with other compounds used for the treatment of the above conditions.

The invention therefore further relates to combination therapies wherein a compound of formula (I) or (Ia) or a pharmaceutically acceptable salt thereof as previously defined or a pharmaceutical composition or formulation comprising a compound of formula (I) or (Ia) or a pharmaceutically acceptable salt thereof as previously defined is administered with another therapeutic agent or agents, for the treatment of one or more of the conditions previously indicated. Such therapeutic agents may be selected from the following:

(i) antidepressants such as, for example, amitriptyline, amoxapine, bupropion, citalopram, clomipramine, desipramine, doxepin duloxetine, elzasonan, escitalopram, fluvoxamine, fluoxetine, gepirone, imipramine, ipsapirone, maprotiline, nortriptyline, nefazodone, paroxetine, phenelzine, protriptyline, reboxetine, robaizotan, sertraline, sibutramine, thionisoxetine, tranylcypromaine, trazodone, trimipramine, venlafaxine, and equivalents and pharmaceutically active isomer(s) and/or metabolite(s) thereof;

(ii) atypical antipsychotics including, for example, quetiapine and pharmaceutically active isomer(s) and/or metabolite(s) thereof;

(iii) antipsychotics including, for example, amisulpride, aripiprazole, asenapine, benzisoxidil, bifeprunox, carbamazepine, clozapine, chlorpromazine, debenzapine, divalproex, duloxetine, eszopiclone, haloperidol, iloperidone, lamotrigine, loxapine, mesoridazine, olanzapine, paliperidone, perlapine, perphenazine, phenothiazine, phenylbutlypiperidine, pimozide, prochlorperazine, risperidone, sertindole, sulpiride, suproclone, suriclone, thioridazine, trifluoperazine, trimetozine, valproate, valproic acid, zopiclone, zotepine, ziprasidone, and equivalents and pharmaceutically active isomer(s) and/or metabolite(s) thereof;

(iv) anxiolytics including, for example, alnespirone, azapirones, benzodiazepines, barbiturates, and equivalents and pharmaceutically active isomer(s) and/or metabolite(s) thereof. Example anxiolytics include adinazolam, alprazolam, balezepam, bentazepam, bromazepam, brotizolam, buspirone, clonazepam, clorazepate, chlordiazepoxide, cyprazepam, diazepam, diphenhydramine, estazolam, fenobam, flunitrazepam, flurazepam, fosazepam, lorazepam, lormetazepam, meprobamate, midazolam, nitrazepam, oxazepam, prazepam, quazepam, reclazepam, tracazolate, trepipam, temazepam, triazolam, uldazepam, and zolazepam; and equivalents and pharmaceutically active isomer(s) and/or metabolite(s) thereof;

(v) anticonvulsants including, for example, carbamazepine, valproate, lamotrogine, and gabapentin, and equivalents and pharmaceutically active isomer(s) and/or metabolite(s) thereof;

(vi) Alzheimer's therapies including, for example, donepezil, memantine, tacrine, and equivalents and pharmaceutically active isomer(s) and/or metabolite(s) thereof;

(vii) Parkinson's therapies including, for example, deprenyl, L-dopa, Requip, Mirapex, MAOB inhibitors such as selegine and rasagiline, comP inhibitors such as Tasmar, A-2 inhibitors, dopamine reuptake inhibitors, NMDA antagonists, Nicotine agonists, and Dopamine agonists and inhibitors of neuronal nitric oxide synthase, and equivalents and pharmaceutically active isomer(s) and/or metabolite(s) thereof;

(viii) migraine therapies including, for example, almotriptan, amantadine, bromocriptine, butalbital, cabergoline, dichloralphenazone, eletriptan, frovatriptan, lisuride, naratriptan, pergolide, pramipexole, rizatriptan, ropinirole, sumatriptan, zolmitriptan, and zomitriptan, and equivalents and pharmaceutically active isomer(s) and/or metabolite(s) thereof;

(ix) stroke therapies including, for example, abciximab, activase, NXY-059, citicoline, crobenetine, desmoteplase, repinotan, traxoprodil, and equivalents and pharmaceutically active isomer(s) and/or metabolite(s) thereof;

(x) urinary incontinence therapies including, for example, darafenacin, falvoxate, oxybutynin, propiverine, robalzotan, solifenacin, and tolterodine, and equivalents and pharmaceutically active isomer(s) and/or metabolite(s) thereof;

(xi) neuropathic pain therapies including, for example, gabapentin, lidoderm, and pregablin, and equivalents and pharmaceutically active isomer(s) and/or metabolite(s) thereof;

(xii) nociceptive pain therapies such as, for example, celecoxib, etoricoxib, lumiracoxib, rofecoxib, valdecoxib, diclofenac, loxoprofen, naproxen, and paracetamol, and equivalents and pharmaceutically active isomer(s) and/or metabolite(s) thereof;

(xiii) insomnia therapies including, for example, allobarbital, alonimid, amobarbital, benzoctamine, butabarbital, capuride, chloral, cloperidone, clorethate, dexclamol, ethchlorvynol, etomidate, glutethimide, halazepam, hydroxyzine, mecloqualone, melatonin, mephobarbital, methaqualone, midaflur, nisobamate, pentobarbital, phenobarbital, propofol, roletamide, triclofos, secobarbital, zaleplon, and Zolpidem, and equivalents and pharmaceutically active isomer(s) and/or metabolite(s) thereof;

(xiv) mood stabilizers including, for example, carbamazepine, divalproex, gabapentin, lamotrigine, lithium, olanzapine, quetiapine, valproate, valproic acid, and verapamil, and equivalents and pharmaceutically active isomer(s) and/or metabolite(s) thereof; (xv) 5HT1B ligands such as, for example, compounds disclosed in WO 99/05134 and WO 02/08212;

(xvi) mGluR2 agonists;

(xvii) alpha 7 nicotinic agonists such as, for example, compounds disclosed in WO 96/006098, WO 97/030998, WO 99/003859, WO 00/042044, WO 01/029034, WO 01/60821, WO 01/36417, WO 02/096912, WO 03/087102, WO 03/087103, WO 03/087104, WO 2004/016617, WO 2004/016616, and WO 2004/019947;

(xviii) chemokine receptor CCR1 inhibitors; and (xix) delta opioid agonists such as, for example, compounds disclosed in WO 97/23466 and WO 02/094794.

Such combination products employ the compound of formula (I) or (Ia) or a pharmaceutically acceptable salt thereof as previously defined within the dosage range described herein and the other pharmaceutically active agent within approved dosage ranges and/or the dosage such as described in the publication reference.

In a further aspect the present invention provides a combination (for example for the treatment of schizophrenia, cognitive disorders or pain) of a compound of formula (I) or (Ia) or a pharmaceutically acceptable salt thereof as hereinbefore defined and one or more agents independently selected from carbamazepine, olanzapine, quetiapine, verapamil, lamotrigine, oxcarbazepine, risperidone, aripiprazol, ziprasidone and lithium.

The invention also provides a pharmaceutical product comprising, in combination, a preparation of a first active ingredient which is a compound of formula (I) or (Ia) or a pharmaceutically acceptable salt thereof as hereinbefore defined, and a preparation of a second active ingredient which is carbamazepine, olanzapine, quetiapine, verapamil, lamotrigine, oxcarbazepine, risperidone, aripiprazol, ziprasidone or lithium, for simultaneous, sequential or separate use in therapy.

In another aspect, the invention provides a kit comprising a preparation of a first active ingredient which is a compound of formula (I) or (Ia) or a pharmaceutically acceptable salt thereof as hereinbefore defined, and a preparation of a second active ingredient which is carbamazepine, olanzapine, quetiapine, verapamil, lamotrigine, oxcarbazepine, risperidone, aripiprazol, ziprasidone or lithium, and instructions for the simultaneous, sequential or separate administration of the preparations to a patient in need thereof.

The present invention will now be further explained by reference to the following illustrative examples.

The methods used for synthesis of the compounds of the invention are illustrated by the general schemes below and the preparative examples that follow. The starting materials and reagents used in preparing these compounds are available from commercial suppliers. These general schemes are merely illustrative of methods by which the compounds of this invention can be synthesised, and various modifications to these schemes can be made and will be suggested to one skilled in the art having referred to this disclosure.

Nuclear magnetic resonance (NMR) spectra were recorded at 400 MHz; the chemical shifts (δ) are reported in parts per million. Spectra were recorded using a Bruker 400 Avance instrument fitted with a 5 mm BBFO probe or DUL probe. Instrument control was by Bruker TopSpin 2.1 software, unless stated otherwise.

Purity was assessed using UPLC with UV (photodiode array) detection over a wide range of wavelengths, normally 220-450 nm, using a Waters Acquity UPLC system equipped with Acquity UPLC BEH or HSS C18 columns (2.1 mm id×50 mm long) operated at 50 or 60° C.

Mobile phases typically consisted of acetonitrile or methanol mixed with water containing either 0.05% formic acid or 0.025% ammonia. Mass spectra were recorded with a Waters SQD single quadrupole mass spectrometer using atmospheric pressure ionisation, unless stated otherwise.

Compounds were purified using normal phase chromatography on silica or alumina, or by reverse phase chromatographic methods, using Biotage or Isolute KPNH Cartridge, SCX cartridge and SCX-2 solid phase extraction cartridges.

Preparative HPLC was performed using an Agilent Technologies 1100 Series system or a Waters autopurification LC/MS system typically using Waters 19 mm id×100 mm long C18 columns such as XBridge or SunFire 5 μm materials at room temperature. Mobile phases typically consisted of acetonitrile or methanol mixed with water containing either 0.1% formic acid or 0.1% ammonia, unless stated otherwise.

Room temperature in the following schemes means the temperature ranging from 20° C. to 25° C.

The following abbreviations are used in the Examples:
AcOH Acetic acid
$BF_3OEt$ Boron trifluoride diethyl etherate
Boc tert-Butoxycarbonyl
nBuLi n-Butyllithium
$CDCl_3$ Deuterated chloroform
DCM Dichloromethane
DIPEA Diisopropylethylamine
DMF N,N-Dimethyl formamide
DMSO Dimethyl sulfoxide
d6-DMSO Deuterated dimethyl sulfoxide
e.e. Percentage enantiomeric excess
Et Ethyl
EtOAc Ethyl acetate
EtOH Ethanol
$Et_3N$ Triethylamine
IPE Diisopropyl ether
LCMS Liquid chromatography mass spectrum
MS Mass spectrum
MeOAc Methyl acetate
Me Methyl
MeCN Acetonitrile
MeOD Deuterated methanol
MeOH Methanol
MW Microwave
NaOH Sodium hydroxide
$NaBH(OAc)_3$ Sodium triacetoxyborohydride
NBS N-bromosuccinimide
NMR Nuclear magnetic resonance
Ph Phenyl
$PhNO_2$ Nitrobenzene
r.t. Room temperature, typically 20 to 25° C.
TFA Trifluoroacetic acid
THF Tetrahydrofuran
TLC Thin layer chromatography
HMBC-HMQC Heteronuclear multiple bond correlation spectroscopy—Heteronuclear multiple quantum correlation spectroscopy

1. INTERMEDIATES

Intermediate 1: 3,5-Diethyl-1-methyl-1H-pyrazole

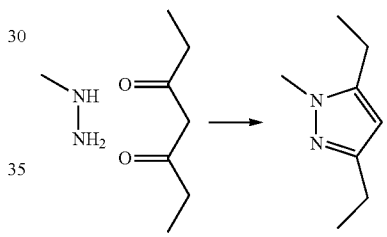

Methylhydrazine (5.0 mL, 95.3 mmol) in ethanol (10 mL) was added drop-wise to a stirred solution of 3,5-heptanedione (11 g, 85.2 mmol) at 5° C. then allowed to stir at room temperature for 2 hours. Acetic acid (2 mL) was added and the mixture refluxed for 1 hour then allowed to cool to room temperature. The solution was concentrated in vacuo to give the title compound (12 g, 94%).

MS ES$^+$: 139

Intermediate 2:
1,5-Dimethyl-3-(trifluoromethyl)-1H-pyrazole

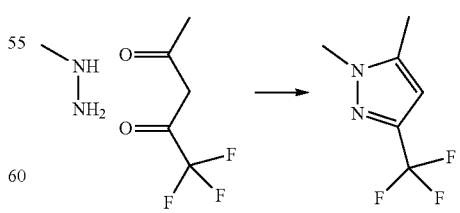

Prepared as described for 3,5-diethyl-1-methyl-1H-pyrazole (Intermediate 1) from methylhydrazine and 1,1,1-trifluoropentane-2,4-dione.

MS ES$^+$: 165

Intermediate 3:
3,5-Dimethyl-1H-pyrazole-4-sulfonyl chloride

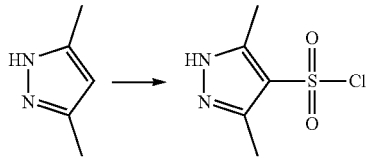

3,5-Dimethyl-1H-pyrazole (3.0 g, 1.0 eq) dissolved in chloroform (5 mL) was added drop-wise to a solution of chlorosulfonic acid (19.95 g, 5.5 eq.) in chloroform (20 mL) under a nitrogen atmosphere at 0° C. with continuous stirring. The reaction was heated at 60° C. for 15 hours under continuous stirring. The reaction was cooled to room temperature and thionyl chloride (4.0 g, 1.1 eq) was gradually added. The reaction was heated at 60° C. for a further 2 hours. The reaction was cooled to room temperature and added to a stirred mixture of dichloromethane (50 mL) and ice cold water (70 mL). The organic layer was separated and the aqueous layer was extracted with dichloromethane (2×70 mL). The combined organic layer was dried over sodium sulfate and evaporated under vacuum to obtain the title compound, 3,5-dimethyl-1H-pyrazole-4-sulfonyl chloride (2.0 g, 42%), as a white solid.

$^1$H NMR (400 MHz, DMSO-$d_6$) δ ppm 2.40 (s, 6H)

MS ES$^+$: 195

Intermediate 4:
3,5-Diethyl-1-methyl-1H-pyrazole-4-sulfonyl chloride

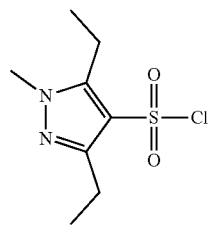

Prepared as described for 3,5-dimethyl-1H-pyrazole-4-sulfonyl chloride (Intermediate 3) from 3,5-diethyl-1-methyl-1H-pyrazole (Intermediate 1).

$^1$H NMR (400 MHz, CDCl$_3$) δ ppm 1.21-1.40 (m, 6H), 2.85 (m, 2H), 2.95 (m, 2H), 3.80 (s, 3H).

Intermediate 5:
1,3-Dimethyl-1H-pyrazole-4-sulfonyl chloride

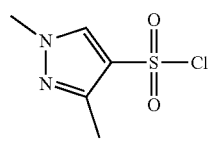

Prepared as described for 3,5-dimethyl-1H-pyrazole-4-sulfonyl chloride (Intermediate 3) from 1,3-dimethylpyrazole.

$^1$H NMR (400 MHz, DMSO-$d_6$) δ ppm 2.48 (s, 3H), 3.91 (s, 3H), 7.92 (s, 1H).

MS ES$^+$: 195

Intermediate 6:
3-(Trifluoromethyl)-1,5-dimethyl-1H-pyrazole

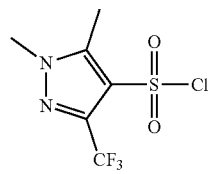

Prepared as described for 3,5-dimethyl-1H-pyrazole-4-sulfonyl chloride (Intermediate 3) from 1,5-dimethyl-3-(trifluoromethyl)-1H-pyrazole (Intermediate 2).

$^1$H NMR (400 MHz, CDCl$_3$) δ ppm 2.63 (s, 3H), 3.91 (s, 3H)

Intermediate 7:
1,4-Dimethyl-1H-pyrazole-5-sulfonyl chloride

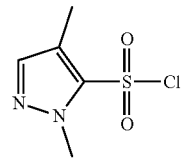

Step (i):

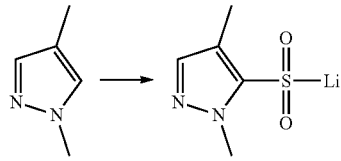

A solution of 23% n-butyl lithium in hexane (17.3 mL, 1.2 eq) was added drop-wise to a solution of 1,4-dimethyl-1H-pyrazole (5 g, 1 eq.) in dry ether (50 mL) at −65° C. under a nitrogen atmosphere. The temperature of the resulting suspension was raised to 0° C. temperature over 1 hour and then cooled to −70° C. Excess sulfur dioxide was bubbled to the mixture for 30 minutes, while maintaining the temperature below −65° C. The solution was stirred at −65° C. for 1 hour and was then allowed to warm to room temperature. The resulting precipitate was filtered, washed with ether and dried to yield the lithium sulfinate salt of 1,4-dimethyl-1H-pyrazole.

$^1$H NMR (400 MHz, DMSO-$d_6$) δ ppm 2.03 (s, 3H) 3.87 (s, 3H) 6.94 (s, 1H)

Step (ii):

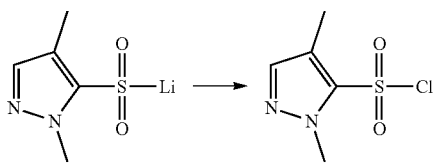

The lithium sulfinate salt of 1,4-dimethyl-1H-pyrazole from step (i) was added to a biphasic mixture of dichloromethane (50 mL) and ice cold water (70 mL). N-chlorosuccinimide (6.23 g, 0.9 eq.) was added portion-wise with vigorous stirring. The reaction mixture was stirred further for 30 minutes at 5° C. The organic layer was separated and the aqueous layer was extracted with dichloromethane (2×30 mL). The combined organic layer was dried over sodium sulfate and evaporated under vacuum to obtain the title compound, 1,4-dimethyl-1H-pyrazole-5-sulfonyl chloride (5.5 g, 55%). The regio-selectivity was confirmed by HMBC-HMQC analysis.

Intermediate 8: 1-(1,3,5-Trimethyl-1H-pyrazole-4-sulfonyl)piperidin-4-one

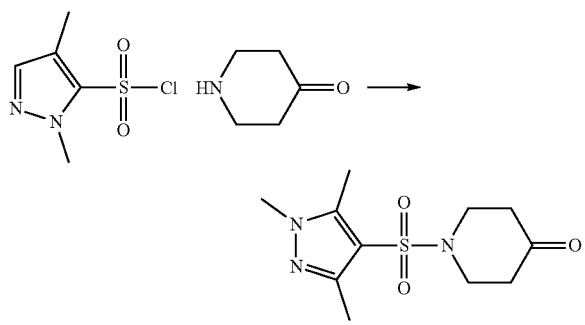

To a solution of 4-piperidine hydrochloride (3.67 g, 23.9 mmol) in dichloromethane (250 mL) was added magnesium sulfate (5 g) and the reaction was stirred at room temperature. After 15 minutes, 1,3,5-trimethyl-1H-pyrazole-4-sulfonyl chloride ((1.0 g, 4.79 mmol) and triethylamine (2.42 g, 23.9 mmol) were added successively and stirred overnight at room temperature. The reaction was filtered, treated with water (25 mL) and extracted into dichloromethane (3×20 mL). The combined organic layers were dried over sodium sulfate, filtered and concentrated under reduced pressure to afford the desired product, 1-(1,3,5-trimethyl-1H-pyrazole-4-sulfonyl)piperidin-4-one (1.24 g, 95%).

MS ES+: 272

Intermediate 9: 1-((3,5-Dimethyl-1H-pyrazol-4-yl)sulfonyl)piperidine-4-carbonitrile

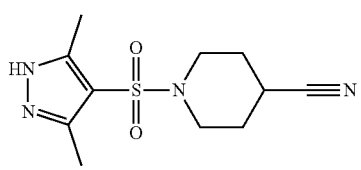 [SMILES: Cc1n[nH]c(C)c1S(=O)(=O)N1CCC(C#N)CC1]

Prepared as described for 1-(1,3,5-trimethyl-1H-pyrazole-4-sulfonyl)piperidin-4-one (Intermediate 8) from 3,5-dimethyl-1H-pyrazole-4-sulfonyl chloride (Intermediate 3) and piperidine-4-carbonitrile.

$^1$H NMR (400 MHz, DMSO-d$_6$) δ ppm 1.65-1.88 (m, 2H) 1.89-2.05 (m, 2H) 2.20-2.37 (m, 6H) 2.65-2.86 (m, 2H) 2.94 (tt, J=8.56, 4.07 Hz, 1H) 3.06-3.23 (m, 2H) 13.10 (br. s., 1H)

MS ES+: 269

Intermediate 10: 4-(4-Chloro-3-fluorophenoxy)piperidine hydrochloride

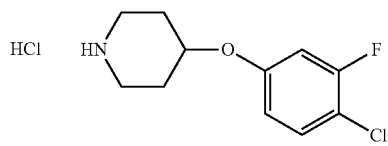 [SMILES: Cl ; Fc1cc(OC2CCNCC2)ccc1Cl]

Step (i):

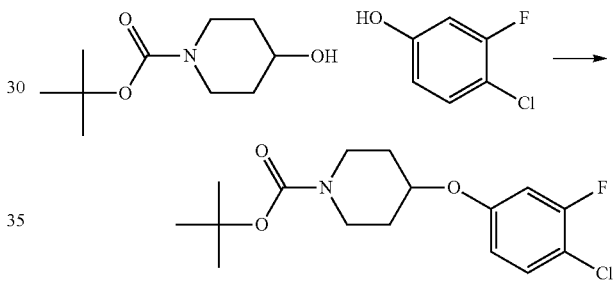

A solution of tert-butyl 4-hydroxypiperidine-1-carboxylate (500 mg, 2.484 mmol) and 4-chloro-3-fluorophenol in THF at 0° C. was treated with diisopropyl azodicarboxylate (483 μl, 2.484 mmol). The reaction mixture was stirred at room temperature for 40 hours. The reaction mixture was treated with ethyl acetate and saturated aqueous sodium hydrogen carbonate. The layers were separated. The aqueous phase was extracted with ethyl acetate and the organic layers were combined, dried over magnesium sulfate, filtered and concentrated in vacuo to yield an oil. The crude product was purified by silica chromatography (solvent system: 20-100% ethyl acetate/petrol). The relevant fractions were combined and concentrated and the resulting product carried through to the next step.

$^1$H NMR (400 MHz, DMSO-d$_6$) δ ppm 1.41 (s, 9H) 1.44-1.57 (m, 2H) 1.85-1.96 (m, 2H) 3.10-3.22 (m, 2H) 3.60-3.70 (m, 2H) 4.55-4.64 (m, 1H) 6.83-6.90 (m, 1H) 7.10-7.17 (m, 1H) 7.42-7.49 (m, 1H)

Step (ii):

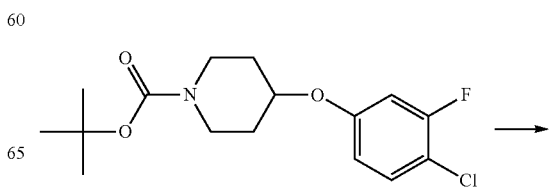

-continued

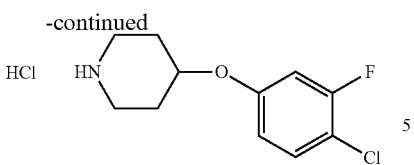

A solution of the tert-butyl 4-(4-chloro-3-fluorophenoxy)piperidine-1-carboxylate from step (i) in 1,4-dioxane (10 mL) was treated with 4M hydrogen chloride in dioxane (2 equivalents). The reaction mixture was stirred at room temperature for 16 hours. The product was filtered and dried under vacuum to give the title compound which was used without further purification.

$^1$H NMR (400 MHz, DMSO-d$_6$) δ ppm 1.76-1.91 (m, 2H) 2.05-2.15 (m, 2H) 2.98-3.11 (m, 2H) 3.15-3.27 (m, 2H) 4.63-4.72 (m, 1H) 6.86-6.94 (m, 1H) 7.13-7.24 (m, 1H) 7.44-7.53 (m, 1H) 8.93 (br. s., 2H)

MS ES$^+$: 230

Intermediate 11:
4-(4-Chloro-2-fluorophenoxy)piperidine hydrochloride

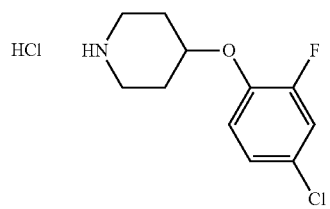

Prepared as described for 4-(4-chloro-3-fluorophenoxy)piperidine hydrochloride (Intermediate 10) from 4-chloro-2-fluorophenol.

Intermediate 12:
5-Chloro-2-(piperidin-4-yloxy)benzonitrile hydrochloride

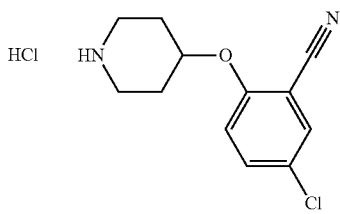 [SMILES: Cl ; N#Cc1cc(Cl)ccc1OC1CCNCC1]

Prepared as described for 4-(4-chloro-3-fluorophenoxy)piperidine hydrochloride (Intermediate 10) from 5-chloro-2-hydroxybenzonitrile.

Intermediate 13:
4-(3-Fluoro-4-methoxyphenoxy)piperidine hydrochloride

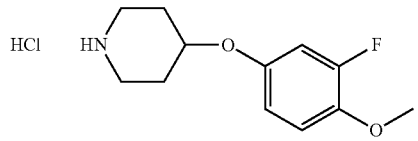 [SMILES: Cl ; COc1ccc(OC2CCNCC2)cc1F]

Prepared as described for 4-(4-chloro-3-fluorophenoxy)piperidine hydrochloride (Intermediate 10) from 3-fluoro-4-methoxyphenol.

Intermediate 14:
4-(4-Chloro-2-(trifluoromethyl)phenoxy)piperidine hydrochloride

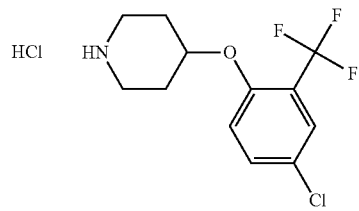 [SMILES: Cl ; FC(F)(F)c1cc(Cl)ccc1OC1CCNCC1]

Prepared as described for 4-(4-chloro-3-fluorophenoxy)piperidine hydrochloride (Intermediate 10) from 4-chloro-2-(trifluoromethyl)phenol.

Intermediate 15:
4-(3,5-Difluoro-4-methoxyphenoxy)piperidine hydrochloride

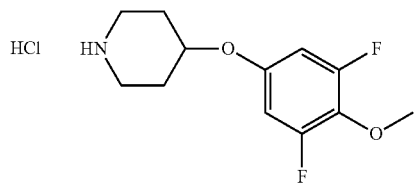 [SMILES: Cl ; COc1c(F)cc(OC2CCNCC2)cc1F]

Prepared as described for 4-(4-chloro-3-fluorophenoxy)piperidine hydrochloride (Intermediate 10) from 3,5-difluoro-4-methoxyphenol.

Intermediate 16:
4-(4-Chloro-2,6-difluorophenoxy)piperidine hydrochloride

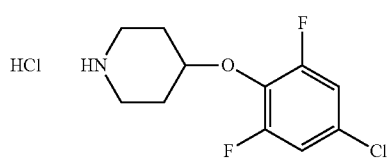 [SMILES: Cl ; Fc1cc(Cl)cc(F)c1OC1CCNCC1]

Prepared as described for 4-(4-chloro-3-fluorophenoxy) piperidine hydrochloride (Intermediate 10) from 4-chloro-2,6-difluorophenol.

Intermediate 17:
4-(4-(Trifluoromethyl)phenoxy)piperidine hydrochloride

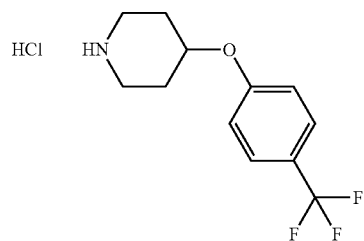 [SMILES: Cl ; FC(F)(F)c1ccc(OC2CCNCC2)cc1]

Prepared as described for 4-(4-chloro-3-fluorophenoxy) piperidine hydrochloride (Intermediate 10) from 4-(trifluoromethyl)phenol.

Intermediate 18:
5-Chloro-2-(piperidin-4-yloxy)pyridine hydrochloride

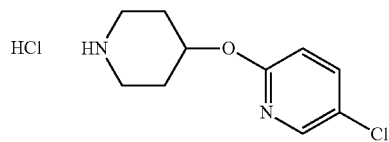 [SMILES: Cl ; Clc1ccc(OC2CCNCC2)nc1]

Step (i):

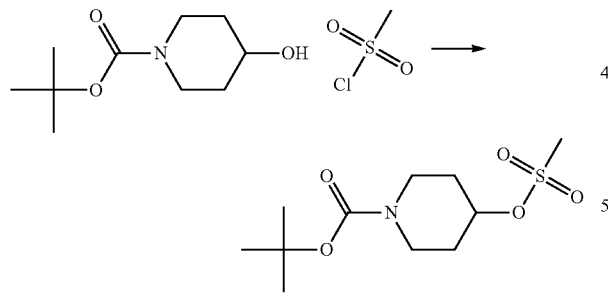

Mesyl chloride (0.542 ml, 6.96 mmol) was added dropwise to a solution of tert-butyl 4-hydroxypiperidine-1-carboxylate (1 g, 4.97 mmol) and triethylamine (0.970 ml, 6.96 mmol) in dichloromethane (25 ml) under nitrogen in an ice bath. The resulting solution was stirred at room temperature for 1 hour. The solution was washed with water, dried (phase separator) and concentrated to give tert-butyl 4-(methylsulfonyloxy)piperidine-1-carboxylate (1.80 g, 6.44 mmol, 130% yield), as a white solid.

$^1$H NMR (400 MHz, DMSO-$d_6$) δ ppm 1.40 (s, 9H) 1.52-1.72 (m, 2H) 1.80-2.04 (m, 2H) 3.11-3.20 (m, 2H) 3.20 (s, 3H) 3.51-3.67 (m, 2H) 4.76-4.89 (m, 1H)

Step (ii):

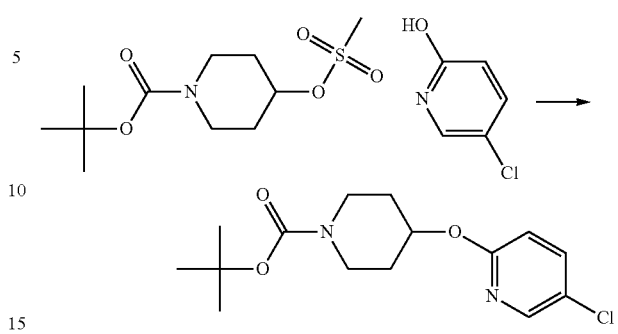

Potassium carbonate (0.352 g, 2.55 mmol) was added to a solution of tert-butyl 4-(methylsulfonyloxy)piperidine-1-carboxylate from step (i) (0.453 g, 1.621 mmol) and 5-chloropyridin-2-ol (0.15 g, 1.158 mmol) in N,N-dimethylformamide (10 ml) in a sealed tube. The reaction was stirred at 75° C. overnight. The reaction was quenched with water and extracted with DCM three times. The combined organics were washed with water, dried (phase separator) and concentrated. The crude product was freeze-dried to remove the remaining DMF. The crude product was purified by 10 g KP-silica Biotage SNAP cartridge eluted with 0-50% ethyl acetate/petrol to give tert-butyl 4-(5-chloropyridin-2-yloxy) piperidine-1-carboxylate (0.116 g, 0.371 mmol, 32.0% yield).

$^1$H NMR (400 MHz, Dichloromethane-$d_2$) δ ppm 1.48 (s, 9H) 1.64-1.81 (m, 2H) 1.90-2.03 (m, 2H) 3.19-3.35 (m, 2H) 3.70-3.85 (m, 2H) 5.13-5.25 (m, 1H) 6.73 (s, 1H) 7.52-7.62 (m, 1H) 8.05-8.14 (m, 1H)

MS ES$^+$: 257

Step (iii):

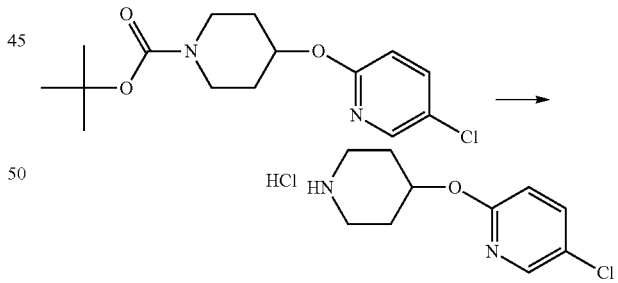

A solution of the tert-butyl 4-(5-chloropyridin-2-yloxy) piperidine-1-carboxylate from step (ii) in 1,4-dioxane (10 mL) was treated with 4M HCl in dioxane (2 equivalents). The reaction mixture was stirred at room temperature for 16 hours. The product was filtered and dried under vacuum to give the title compound which was used without further purification.

$^1$H NMR (400 MHz, DMSO-$d_6$) δ ppm 1.80-1.95 (m, 2H) 2.07-2.23 (m, 2H) 3.00-3.15 (m, 2H) 3.17-3.27 (m, 2H) 5.10-5.26 (m, 1H) 6.85-6.96 (m, 1H) 7.78-7.90 (m, 1H) 8.15-8.27 (m, 1H) 8.77 (br. s., 2H)

Intermediate 19: 4-(4-Chlorophenoxy)-2-methylpiperidine hydrochloride

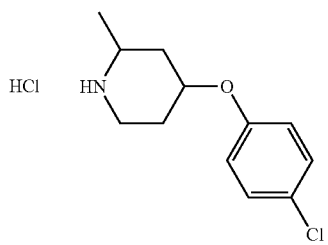

(i) tert-Butyl 4-hydroxy-2-methylpiperidine-1-carboxylate

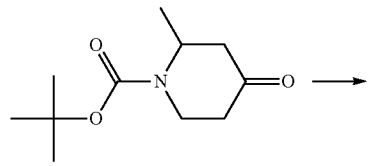

To a solution of 1-Boc-2-methyl-4-piperidinone (1.0 g, 4.68 mmol) in methanol (10 mL) at 0° C. was added sodium borohydride (265 mg, 7.03 mmol) portionwise. The reaction was stirred under an atmosphere of nitrogen at 0° C. for 1 hour. It was then allowed to reach room temperature and stirred for a further 2.5 hours. The reaction was deemed complete by its LC-MS analysis and quenched using saturated ammonium chloride aqueous solution and the methanol removed under reduced pressure. The remaining aqueous layer was extracted using dichloromethane (25 ml×3), the combined organic layers were dried over sodium sulphate, filtered and concentrated under reduced pressure to afford the desired product, tert-butyl 4-hydroxy-2-methylpiperidine-1-carboxylate (1.0 g, 100%).

MS ES+: 216.4

(ii) tert-Butyl 4-(4-chlorophenoxy)-2-methylpiperidine-1-carboxylate

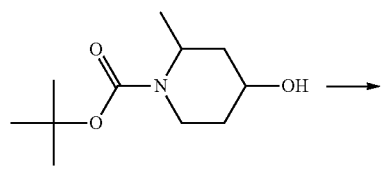

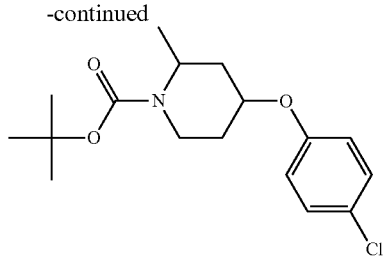

Prepared as described for tert-Butyl 4-(4-chlorophenoxy)-3-methylpiperidine-1-carboxylate (Intermediate 20 step (ii)) from tert-Butyl 4-hydroxy-2-methylpiperidine-1-carboxylate (Intermediate 19 step (i)).

$^1$H NMR (400 MHz, CDCl$_3$) δ ppm 1.15 (d, 3H), 1.40 (s, 9H), 1.41-1.49 (m, 1H), 1.59-1.68 (m, 1H), 1.88-1.94 (m, 1H), 1.98-2.08 (m, 1H), 2.82-2.94 (m, 1H), 3.98-4.08 (m, 1H), 4.34-4.48 (m, 1H), 4.46-4.54 (m, 1H), 6.73-6.78 (m, 2H), 7.13-7.18 (m, 2H).

MS: ES+ 326

(iii) 4-(4-Chlorophenoxy)-2-methylpiperidine hydrochloride

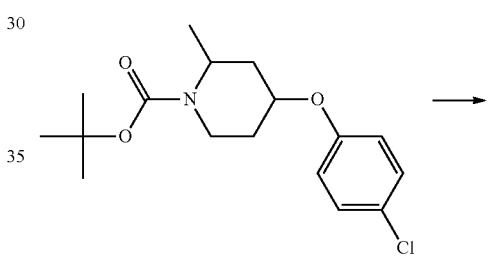

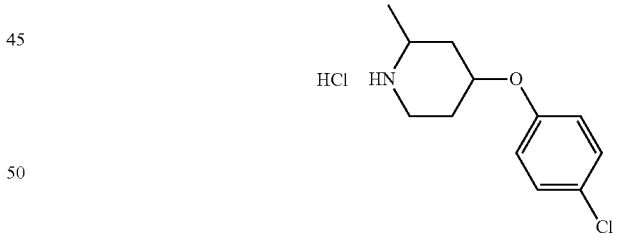

A solution of the tert-butyl 4-(4-chlorophenoxy)-2-methylpiperidine-1-carboxylate from step (ii) in 1,4-dioxane (10 mL) was treated with 4M hydrogen chloride in dioxane. The reaction mixture was stirred at room temperature for 16 hours. The product was filtered and dried under vacuum to give the title compound which was used without further purification.

$^1$H NMR (400 MHz, CDCl$_3$) δ ppm 1.48 (d, 3H), 1.80-2.28 (m, 4H), 3.12-3.78 (m, 3H), 4.59-4.62 (m, 1H), 6.73-6.78 (m, 2H), 7.18-7.22 (m, 2H), 9.42 (br.s, 1H), 9.71 (br.s, 1H).

MS: ES+ 226

Intermediate 20: 4-(4-Chlorophenoxy)-3-methylpiperidine hydrochloride

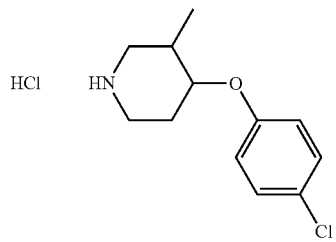

(i) tert-Butyl 4-hydroxy-3-methylpiperidine-1-carboxylate

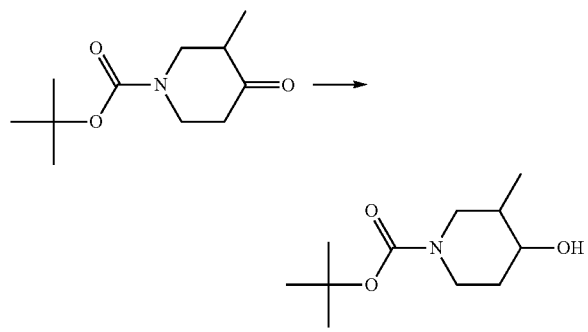

Sodium borohydride (0.265 g, 7.03 mmol) was added in several portions to a solution of (R,S)-tert-butyl-3-methyl-4-oxopiperidine-1-carboxylate (1.0 g, 4.68 mmol) in methanol (10 mL) at 0° C. The reaction mixture was stirred at 0° C. for one hour, then warmed to room temperature and stirred for 2.5 hours. The reaction mixture was quenched with saturated ammonium chloride aqueous solution and concentrated under reduced pressure in order to remove the methanol. This was extracted with dichloromethane. The combined organic layers were dried over sodium sulfate, filtered and concentrated to afford the desired product as a colourless oil (quantitative yield).

$^1$H NMR (400 MHz, CDCl$_3$) δ ppm 0.87-0.94 (m, 3H), 1.33-1.88 (m, 3H), 1.38 (s, 9H), 2.23-4.08 (m, 5H).

MS: ES+ 216

(ii) tert-Butyl 4-(4-chlorophenoxy)-3-methylpiperidine-1-carboxylate

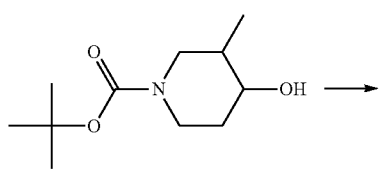

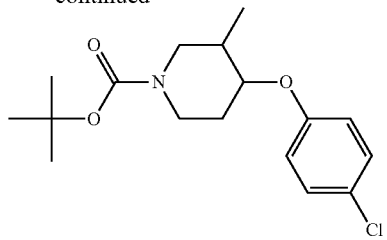

Diethyl azodicarboxylate (0.46 mL, 2.90 mmol) was added to a solution of tert-butyl-4-hydroxy-3-methylpiperidine-1-carboxylate from step (i) (0.50 g, 2.32 mmol), 4-chlorophenol (0.25 g, 2.32 mmol) and triphenylphosphine (0.76 g, 2.90 mmol) in tetrahydrofuran (10 mL). The reaction mixture was stirred at room temperature overnight. LCMS analysis showed no reaction, so heated to 50° C. overnight then cooled to room temperature. Diethyl ether was added and washed with water, 0.4 M sodium hydroxide solution, water and brine. The organic phase was dried over sodium sulfate, filtered and concentrated. The residue was purified via silica gel flash column chromatography using petroleum ether:ethyl acetate (97:3) as solvent system in order to afford the desired product as a colourless oil (138 mg, 18% yield).

$^1$H NMR (400 MHz, CDCl$_3$) δ ppm 0.95 (d, 3H), 1.40 (s, 9H), 1.36-1.50 (m, 1H), 1.76-1.86 (m, 1H), 1.90-2.0 (m, 1H), 2.59-2.81 (m, 1H), 2.89-3.06 (m, 1H), 3.70-3.99 (m, 3H), 6.74-6.79 (m, 2H), 7.13-7.18 (m, 2H).

MS: ES+ 326

(iii) 4-(4-Chlorophenoxy)-3-methylpiperidine hydrochloride

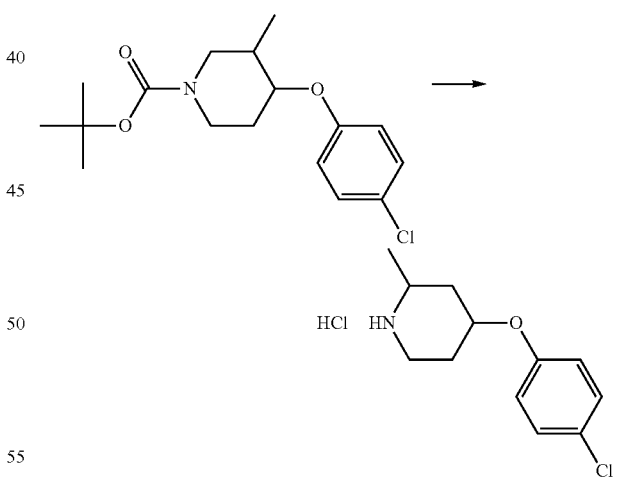

A solution of hydrochloric acid (4M in 1,4-dioxane) (0.53 mL, 2.11 mmol) was added to a solution of tert-butyl-4-(4-chlorophenoxy)-3-methylpiperidine-1-carboxylate from step (ii) (138 mg, 0.42 mmol) in 1,4-dioxane (10 mL) and the mixture was stirred at room temperature overnight. A further portion of hydrochloric acid (4M in 1,4-dioxane) (5 mL, 20.02 mmol) was added to the mixture and stirred for three hours. The reaction mixture was concentrated and was azeotroped with dichloromethane twice in order to give the desired product as a cream solid (quantitative yield).

$^1$H NMR (400 MHz, CDCl$_3$) δ ppm 1.19 (d, 3H), 1.90-2.37 (m, 3H), 2.71-2.71 (m, 1H), 2.98-3.10 (m, 1H), 3.35-3.50 (m, 2H), 3.93-4.02 (m, 1H), 6.73-6.77 (m, 2H), 7.10-7.22 (m, 2H), 9.50 (br.s, 1H), 9.69 (br.s, 1H).

MS: ES$^+$: 226

Intermediate 21: Ethyl 4-(4-chlorobenzyl)piperidine-4-carboxylate hydrochloride

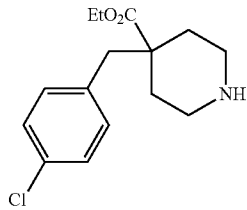 [SMILES: CCOC(=O)C1(Cc2ccc(Cl)cc2)CCNCC1]

1-tert-Butyl 4-ethyl 4-(4-chlorobenzyl)piperidine-1,4-dicarboxylate (1 g, 2.62 mmol) was treated with 4 M HCl in dioxane (4 ml, 16.00 mmol) and stirred at room temperature for 18 hours. The reaction was evaporated to dryness to leave a white solid (0.708 g) that was used without purification.

MS ES+: 282

Intermediate 22: tert-Butyl 4-(3,4-dichlorobenzyl)-4-hydroxypiperidine-1-carboxylate

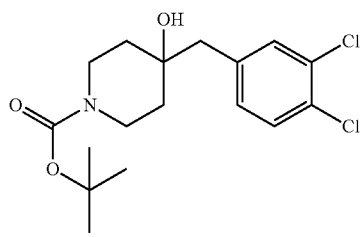 [SMILES: CC(C)(C)OC(=O)N1CCC(O)(Cc2ccc(Cl)c(Cl)c2)CC1]

Magnesium turnings (0.98 g, 0.04 mol) was added to anhydrous diethyl ether (25 mL) followed by addition of catalytic amount of iodine (0.05 g). The reaction was stirred at reflux under nitrogen atmosphere. A solution of 3,4-dichlorobenzyl chloride (4.0 g, 0.02 mol) in diethyl ether (10 mL) was added drop wise to the reaction mass at refluxed temperature and the resulting mixture was refluxed for 1.5 hrs. In a separate flask, N-Boc-4-piperidone (2.46 g, 0.012 mol) was dissolved in anhydrous diethyl ether (50 mL) and cooled to 0° C. under nitrogen. The prepared Grignard reagent was added to the solution at 0° C. and the resulting mixture was stirred at room temperature for 2 hours. The reaction was diluted with saturated aqueous ammonium chloride and extracted with ethyl acetate. The organic layers were washed with brine, dried over sodium sulfate and concentrated. The crude compound was purified by silica column chromatography eluted with 0-15% ethyl acetate/n-hexane to afford tert-Butyl 4-(3,4-dichlorobenzyl)-4-hydroxypiperidine-1-carboxylate (3.0 g, 41% yield).

Intermediate 23: 4-(3,4-Dichlorobenzyl)piperidin-4-ol 2,2,2-trifluoroacetate

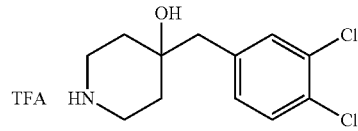 [SMILES: OC1(Cc2ccc(Cl)c(Cl)c2)CCNCC1]

Trifluoroacetic acid (15 mL) was added to a solution of tert-butyl 4-(3,4-dichlorobenzyl)-4-hydroxypiperidine-1-carboxylate (Intermediate 22, 3.0 g, 8.3 mmol) in DCM (30 mL) at 0° C. The reaction was stirred at room temperature for 45 minutes then concentrated and azeotroped with DCM to afford 4-(3,4-Dichlorobenzyl)piperidin-4-ol 2,2,2-trifluoroacetate (2.0 g, 65% yield).

Intermediate 24: tert-Butyl 4-(4-chloro-3-fluorobenzylidene)piperidine-1-carboxylate

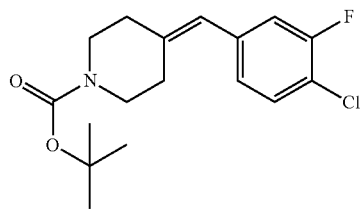 [SMILES: CC(C)(C)OC(=O)N1CCC(=Cc2ccc(Cl)c(F)c2)CC1]

A suspension of triphenylphosphine (2.347 g, 8.95 mmol) and 4-(bromomethyl)-1-chloro-2-fluorobenzene (2 g, 8.95 mmol) in ether (25 mL) was stirred at room temperature overnight. The suspension was concentrated to give (4-chloro-3-fluorobenzyl)triphenylphosphonium bromide (quantitative) as a white solid that was used crude. Butyl lithium (1.6 M in hexanes) (6.03 mL, 9.65 mmol) was added slowly to a suspension of (4-chloro-3-fluorobenzyl)triphenylphosphonium bromide (4.26 g, 8.77 mmol) in THF (40 mL) under inert atmosphere at 0° C. The resulting suspension was stirred at 0° C. for 15 minutes, then warmed to room temperature for 2 hours. tert-Butyl 4-oxopiperidine-1-carboxylate (1.922 g, 9.65 mmol) as a solution in THF (5 mL) was added and the suspension was stirred at room temperature overnight. Petroleum ether was added, the precipitate (O=PPh3) was filtered and the filtrate concentrated. The crude product was purified by silica chromatography eluted with 0-100% DCM/petroleum ether to give tert-butyl 4-(4-chloro-3-fluorobenzylidene)piperidine-1-carboxylate (2.03 g, 6.23 mmol, 71% yield) as a colourless oil that solidified on standing.

$^1$H NMR (400 MHz, DMSO-d$_6$) δ ppm 1.42 (s, 9H) 2.28-2.30 (m, 2H) 2.39-2.40 (m, 2H) 3.27-3.34 (m, 2H) 3.36-3.47 (m, 2H) 6.35 (s, 1H) 7.06-7.13 (m, 1H) 7.25-7.28 (m, 1H) 7.51-7.55 (m, 1H)

Intermediate 25: 4-(4-Chloro-3-fluorobenzyl)piperidine hydrochloride

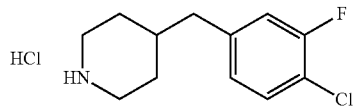 [SMILES: Cl ; Fc1cc(CC2CCNCC2)ccc1Cl]

A flask charged with tert-butyl 4-(4-chloro-3-fluorobenzylidene)piperidine-1-carboxylate (2.03 g, 6.23 mmol, Intermediate 24) and platinum(IV)oxide (0.141 g, 0.623 mmol) was evacuated and flushed with argon three times. The flask was evacuated again and ethanol (20 mL) and ethyl acetate (20 mL) were added then the suspension stirred under an atmosphere of hydrogen for 2 hours. The suspension was filtered through diatomaceous earth and the filtrate concentrated to give tert-butyl 4-(4-chloro-3-fluorobenzyl)piperidine-1-carboxylate (2.01 g, 6.13 mmol, 98% yield) as a yellow oil that was used without further purification. Hydrogen chloride (4M in dioxane) (3.05 mL, 12.20 mmol) was added to a solution of tert-butyl 4-(4-chloro-3-fluorobenzyl)piperidine-1-carboxylate (2 g, 6.10 mmol) in Methanol (20 mL) and stirred overnight. The solution was concentrated and azeotroped with toluene to give 4-(4-chloro-3-fluorobenzyl)piperidine hydrochloride (1.56 g, 5.91 mmol, 97% yield) as a white solid.

$^1$H NMR (400 MHz, DMSO-d$_6$) δ ppm 1.28-1.44 (m, 2H) 1.60-1.73 (m, 2H) 1.74-1.88 (m, 1H) 2.54-2.60 (m, 2H) 2.69-2.86 (m, 2H) 3.15-3.25 (m, 2H) 7.05-7.12 (m, 1H) 7.24-7.32 (m, 1H) 7.46-7.54 (m, 1H) 8.80 (br. s., 1H) 9.06 (br. s., 1H)

Intermediate 26: 4-(4-Chloro-2-methoxyphenoxy)piperidine hydrochloride

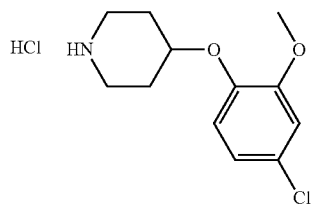 [SMILES: Cl ; COc1cc(Cl)ccc1OC1CCNCC1]

Prepared as described for 4-(4-chloro-3-fluorophenoxy)piperidine hydrochloride (Intermediate 10) from 4-chloro-2-methoxyphenol.
MS: ES+ 242

Intermediate 27: tert-Butyl 4-(4-chloro-2-fluorobenzyl)-4-hydroxypiperidine-1-carboxylate

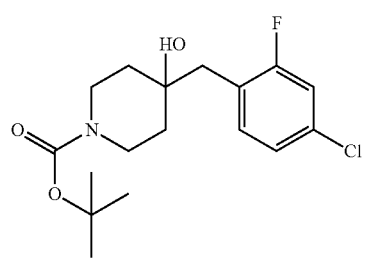 [SMILES: CC(C)(C)OC(=O)N1CCC(O)(Cc2ccc(Cl)cc2F)CC1]

Prepared as described for tert-Butyl 4-(3,4-dichlorobenzyl)-4-hydroxypiperidine-1-carboxylate (Intermediate 22) from 4-chloro-2-fluoro benzyl bromide.

$^1$H NMR (400 MHz, DMSO-d$_6$) δ ppm 1.30-1.42 (m, 13H) 2.69 (s, 2H) 2.99 (br, s., 2H) 3.59-3.67 (m, 2H) 4.52 (s, 1H) 7.20-7.23 (m, 1H) 7.31-7.36 (m, 2H)

Intermediate 28: 4-(4-Chloro-2-fluorobenzyl)piperidin-4-ol 2,2,2-trifluoroacetate

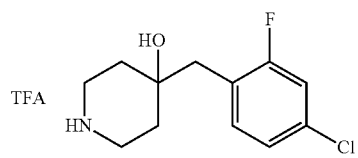 [SMILES: OC1(Cc2ccc(Cl)cc2F)CCNCC1]

Prepared as described for 4-(3,4-Dichlorobenzyl)piperidin-4-ol 2,2,2-trifluoroacetate (Intermediate 23) using tert-Butyl 4-(4-chloro-2-fluorobenzyl)-4-hydroxypiperidine-1-carboxylate (Intermediate 27).
MS: ES+ 244

Intermediate 29: 5-Chloro-3-fluoro-2-(piperidin-4-yloxy)pyridine hydrochloride

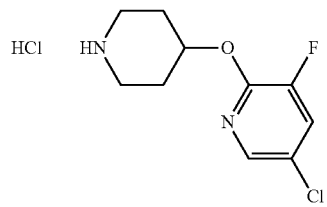 [SMILES: Cl ; Fc1cc(Cl)cnc1OC1CCNCC1]

A solution of tert-butyl 4-hydroxypiperidine-1-carboxylate (0.5 g, 2.4 mmol) in DMF (5 mL) was added to a suspension of sodium hydride (0.065 g, 2.7 mmol) in DMF (3 mL) at room temperature and stirred for 30 minutes. 5-Chloro-2,3-difluoropyridine (0.4 g, 2.7 mmol) was added at 0° C. and then heated at 60° C. for 4 hours. The reaction was poured into cold water and extracted with ethyl acetate. The combined organic layer was washed with brine and then dried over sodium sulfate and concentrated. The crude compound was purified by silica column chromatography eluted with 0-20% ethyl acetate in hexane to yield tert-butyl 4-(5-chloro-3-fluoropyridin-2-yloxy) piperidine-1-carboxylate (0.5 g, 60% yield). 12% HCl in dioxane (5 mL) was added to tert-butyl 4-(5-chloro-3-fluoropyridin-2-yloxy)piperidine-1-carboxylate (0.5 g, 1.5 mmol) in dioxane (2 mL) and stirred at room temperature for 2 hours. The reaction was concentrated. The crude compound was purified by trituration with diethyl ether (10×2 mL) to afford 5-chloro-3-fluoro-2-(piperidin-4-yloxy)pyridine hydrochloride (0.3 g, 34% yield).

$^1$H NMR (400 MHz, DMSO-d$_6$) δ ppm 1.88-1.97 (m, 2H) 2.13-2.19 (m, 2H) 3.09-3.14 (m, 2H) 3.21-3.24 (m, 2H) 5.27-5.31 (m, 1H) 8.06-8.09 (m, 2H) 8.91-8.92 (m, 2H)

Intermediate 30: 4-(4-Chloro-2-methoxybenzyl)piperidine hydrochloride

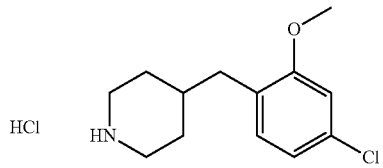 [SMILES: Cl ; COc1cc(Cl)ccc1CC1CCNCC1]

Prepared as described for 4-(4-chloro-3-fluorobenzyl)piperidine hydrochloride (Intermediate 25) using 4-chloro-1-(chloromethyl)-2-methoxybenzene.

$^1$H NMR (400 MHz, DMSO-$d_6$) δ ppm 1.27-1.41 (m, 2H) 1.60-1.70 (m, 2H) 1.70-1.84 (m, 1H) 2.48 (br. s., 1H) 2.72-2.83 (m, 2H) 3.16-3.24 (m, 2H) 3.80 (s, 3H) 6.92-6.97 (m, 1H) 7.03-7.06 (m, 1H) 7.11-7.16 (m, 1H) 8.51 (br. s, 1H) 8.79 (br. s, 1H)

Intermediate 31: 4-(4-Chloro-2-fluorobenzyl)-4-fluoropiperidine hydrochloride

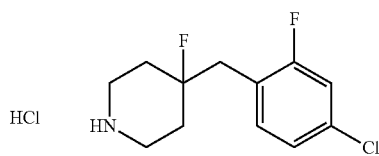 [SMILES: Cl ; Fc1cc(Cl)ccc1CC1(F)CCNCC1]

A solution of tert-butyl 4-(4-chloro-2-fluorobenzyl)-4-hydroxypiperidine-1-carboxylate (Intermediate 27, 5 g, 0.014 mol) in dry DCM (50 mL) was added dropwise at −70° C. to a stirred solution of diethylaminosulfurtrifluoride (2.81 g, 0.017 mol) in dry dichloromethane (50 mL) under nitrogen. After stirring at −50° C. for 45 min the reaction was warmed to room temperature. The reaction was poured into a saturated aqueous solution of sodium bicarbonate and extracted with dichloromethane. The organic layer was dried over sodium sulfate and concentrated. The crude compound was purified by silica column chromatography eluted with 0-5% ethyl acetate/n-hexane to yield tert-butyl 4-(4-chloro-2-fluorobenzyl)-4-fluoropiperidine-1-carboxylate (1.7 g, 34% yield). HCl-dioxane (30 mL) was added dropwise tert-butyl 4-(4-chloro-2-fluorobenzyl)-4-fluoropiperidine-1-carboxylate (1.7 g, 0.005 mol) in dioxane (10 mL) at 0° C. The resulting solution was stirred at room temperature for 1 hour. The reaction was concentrated. The crude compound was purified by triturating in diethyl ether (20 mL×3) to yield 4-(4-chloro-2-fluorobenzyl)-4-fluoropiperidine hydrochloride (1.2 g, 87% yield).

MS: ES+ 246

Intermediate 32: tert-Butyl 4-(4-chloro-2-methoxybenzyl)-4-hydroxypiperidine-1-carboxylate

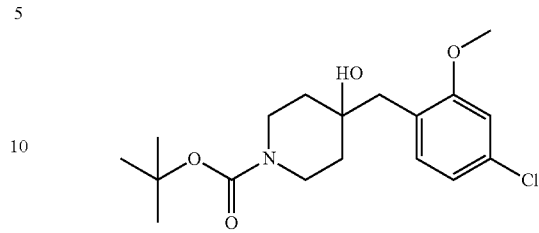

(4-chloro-2-methoxyphenyl) methanol (10 g, 0.058 mol) was dissolved in DCM (100 mL) and thionyl chloride (20.75 g, 0.174 mol) was added dropwise under nitrogen at room temperature. The reaction was refluxed for 30 minutes. The reaction was poured into ice water (100 mL) and extracted with dichloromethane. The organic layer was dried over sodium sulfate and concentrated. The crude compound was purified by silica column chromatography eluted with 0-10% ethyl acetate/n-hexane to yield 4-chloro-2-methoxy benzyl chloride (9.1 g, 82.42% yield). Magnesium turnings (1.26 g, 0.052 mol) were added to anhydrous diethyl ether (20 mL) followed by addition of catalytic iodine (0.005 g). The reaction was stirred at reflux under nitrogen. A solution of 4-chloro-2-methoxy benzyl chloride (5.0 g, 0.026 mol) in diethyl ether (15 mL) was added drop wise to the reaction at refluxed temperature and resulting mixture was refluxed for 1.5 hours. In another flask, tert-butyl 4-oxopiperidine-1-carboxylate (3.14 g, 0.015 mol) was dissolved in anhydrous diethyl ether (50 mL) and cooled to 0° C. under nitrogen. The prepared Grignard reagent was added to the solution at 0° C. and the resulting mixture was stirred at room temperature for 2 hours. The reaction was diluted with saturated aqueous ammonium chloride and extracted with ethyl acetate. The organic layer was washed with brine, dried over sodium sulfate and concentrated. The crude compound was purified by silica column chromatography eluted with 0-15% ethyl acetate/n-hexane to yield tert-butyl 4-(4-chloro-2-methoxybenzyl)-4-hydroxypiperidine-1-carboxylate (3.4 g, 37% yield).

MS: ES+ 256 (M-100 (boc group))

Intermediate 33: 4-(4-Chloro-2-methoxybenzyl)-4-methoxypiperidine hydrochloride

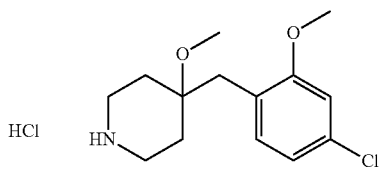 [SMILES: Cl ; COc1cc(Cl)ccc1CC1(OC)CCNCC1]

Sodium hydride (60% in paraffin; 0.56 g, 0.014 mol) was suspended in THF (50 mL) and tert-butyl 4-(4-chloro-2-methoxybenzyl)-4-hydroxypiperidine-1-carboxylate (Intermediate 32, 2.5 g, 0.007 mol) was added in THF (20 mL) slowly at room temperature. The reaction mixture was heated to 50° C. for 2 hours and then cooled to room temperature.

Hexamethylphosphoramide (6.3 g, 0.035 mol) and methyl iodide (10 g, 0.07 mol) were added and the reaction was stirred at 50° C. overnight. The reaction was poured into saturated aqueous sodium bisulfate solution and extracted with ethyl acetate. The organic layer was washed with brine, dried over sodium sulfate and concentrated. The crude compound was purified by silica column chromatography eluted with 0-15% ethyl acetate/n-hexane to yield tert-butyl 4-(4-chloro-2-methoxybenzyl)-4-methoxypiperidine-1-carboxylate (1.7 g, 66% yield). HCl-dioxane (30 mL) was added dropwise to tert-butyl 4-(4-chloro-2-methoxybenzyl)-4-methoxypiperidine-1-carboxylate (1.7 g, 0.0046 mol) in dioxane (10 mL) at 0° C. and the resulting solution was stirred at room temperature for 1 hour. The reaction was concentrated under vacuum. The crude compound was purified by triturating in diethyl ether (20 mL×3) to yield 4-(4-chloro-2-methoxybenzyl)-4-methoxypiperidine hydrochloride (1.3 g, 93% yield).

MS: ES+ 270

Intermediate 34:
4-(4-Chloro-2-methoxybenzyl)piperidin-4-ol hydrochloride

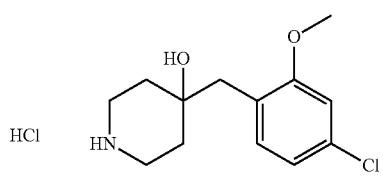 [SMILES: Cl ; COc1cc(Cl)ccc1CC1(O)CCNCC1]

HCl-dioxane (30 mL) was added dropwise to tert-butyl 4-(4-chloro-2-methoxybenzyl)-4-hydroxypiperidine-1-carboxylate (Intermediate 32, 3.0 g, 0.008 mol) in dioxane (10 mL) at 0° C. and the resulting solution was stirred at room temperature for 1 hour. The reaction was concentrated. The crude compound was purified by triturating in diethyl ether (20 mL×3) to yield 4-(4-chloro-2-methoxybenzyl)piperidin-4-ol hydrochloride (2.1 g, 86% yield).

MS: ES+ 256

Intermediate 35:
4-(4-Chloro-2-methoxybenzyl)-4-fluoropiperidine hydrochloride

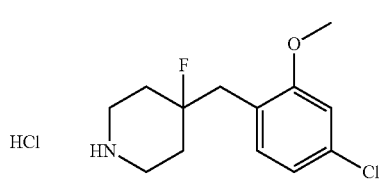 [SMILES: Cl ; COc1cc(Cl)ccc1CC1(F)CCNCC1]

Prepared as described for 4-(4-Chloro-2-fluorobenzyl)-4-fluoropiperidine hydrochloride (Intermediate 31) using tert-butyl 4-(4-chloro-2-methoxybenzyl)-4-hydroxypiperidine-1-carboxylate (Intermediate 32).

MS: ES+ 258

Intermediate 36: tert-Butyl 4-((4-chloro-2-fluorophenyl)(cyano)methyl)piperidine-1-carboxylate

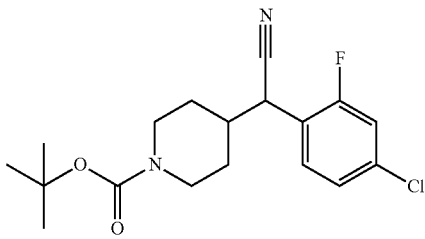 [SMILES: CC(C)(C)OC(=O)N1CCC(C(C#N)c2ccc(Cl)cc2F)CC1]

A solution of 2-(4-chloro-2-fluorophenyl)acetonitrile (0.353 g, 2.082 mmol) in DMF (5 mL) was cooled to 0-5° C., to this was added sodium hydride (0.050 g, 2.082 mmol) and tert-butyl 4-bromopiperidine-1-carboxylate (0.5 g, 1.893 mmol). The reaction was stirred at room temperature for 3 hours. The mixture was quenched with ice/water and partitioned between ethyl acetate and water. The phases were separated and the aqueous extracted with ethyl acetate. The combined organics were washed with water, dried ($Na_2SO_4$) and concentrated in vacuo. The crude product was purified by column chromatography on silica, eluted with 0-50% ethyl acetate/petroleum ether to afford tert-butyl 4-((4-chloro-2-fluorophenyl)(cyano)methyl)piperidine-1-carboxylate (0.5 g, 75%).

Intermediate 37: 2-(4-Chloro-2-fluorophenyl)-2-(piperidin-4-yl)acetonitrile hydrochloride

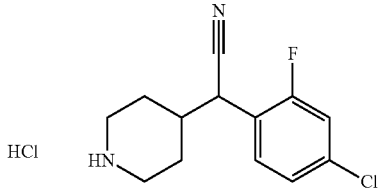 [SMILES: Cl ; N#CC(c1ccc(Cl)cc1F)C1CCNCC1]

tert-Butyl 4-((4-chloro-2-fluorophenyl)(cyano)methyl)piperidine-1-carboxylate (Intermediate 36, 0.5 g, 1.417 mmol) was dissolved in Dioxane (1 mL) and HCl 12% in dioxane (5.02 mL, 19.84 mmol) added. The reaction was stirred at room temperature for 4 hours then concentrated under reduced pressure and triturated with diethyl ether to give 2-(4-chloro-2-fluorophenyl)-2-(piperidin-4-yl)acetonitrile hydrochloride (0.3 g, 85%).

Intermediate 38: tert-Butyl 4-((4-chlorophenyl)(cyano)methyl)piperidine-1-carboxylate

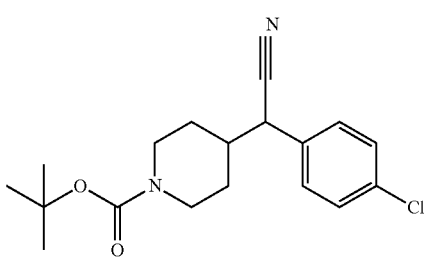

Prepared as described for tert-butyl 4-((4-chloro-2-fluorophenyl)(cyano)methyl)piperidine-1-carboxylate (Intermediate 36) from 2-(4-chlorophenyl)acetonitrile.
MS: ES− 333

Intermediate 39:
2-(4-Chlorophenyl)-2-(piperidin-4-yl)acetonitrile hydrochloride

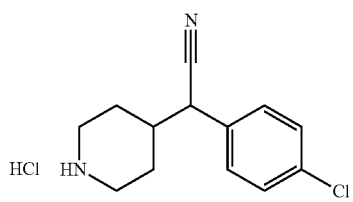 [SMILES: Cl ; N#CC(c1ccc(Cl)cc1)C1CCNCC1]

Prepared as described for 2-(4-Chloro-2-fluorophenyl)-2-(piperidin-4-yl)acetonitrile hydrochloride (Intermediate 37) using tert-butyl 4-((4-chlorophenyl) (cyano)methyl)piperidine-1-carboxylate (Intermediate 38).

Intermediate 40: tert-Butyl 4-(4-chlorobenzoyl)piperidine-1-carboxylate

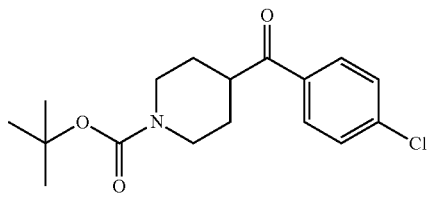 [SMILES: CC(C)(C)OC(=O)N1CCC(C(=O)c2ccc(Cl)cc2)CC1]

Di-tert-butyl dicarbonate (0.923 g, 4.23 mmol) was added to a solution of (4-chlorophenyl)(piperidin-4-yl)methanone hydrochloride (1 g, 3.84 mmol) and triethylamine (1.179 mL, 8.46 mmol) in Methanol (20 mL) under nitrogen. The reaction was stirred at room temperature overnight. The suspension was concentrated in vacuo. The residue was taken up in ethyl acetate and water and the phases separated. The organic was washed with brine, dried (phase separator) and concentrated to give tert-butyl 4-(4-chlorobenzoyl)piperidine-1-carboxylate (1.22 g, 3.77 mmol, 98% yield) as a white solid.
$^1$H NMR (400 MHz, DMSO-$d_6$) δ ppm 1.33-1.46 (m, 11H) 1.72-1.81 (m, 2H) 2.83-3.00 (m, 2H) 3.62 (s, 1H) 3.92-4.02 (m, 2H) 7.58-7.65 (m, 2H) 7.98-8.04 (m, 2H)

Intermediate 41: tert-Butyl 4-((4-chlorophenyl)(hydroxy)methyl)piperidine-1-carboxylate

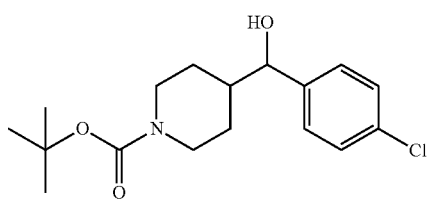 [SMILES: CC(C)(C)OC(=O)N1CCC(C(O)c2ccc(Cl)cc2)CC1]

Sodium borohydride (0.140 g, 3.71 mmol) was added to a suspension of tert-butyl 4-(4-chlorobenzoyl)piperidine-1-carboxylate (Intermediate 40, 1 g, 3.09 mmol) in Methanol (15 mL) under nitrogen at 0° C. The reaction was stirred at room temperature for 1.5 hours. The reaction was quenched with water and the methanol evaporated. The aqueous was extracted with ethyl acetate and the combined organics washed with brine, dried (phase separator) and concentrated to give tert-butyl 4-((4-chlorophenyl)(hydroxy)methyl)piperidine-1-carboxylate (1.01 g, 3.10 mmol, 100% yield) as a colourless oil.
$^1$H NMR (400 MHz, DMSO-$d_6$) δ ppm 1.00-1.12 (m, 2H) 1.20 (s, 1H) 1.37 (s, 9H) 1.51-1.64 (m, 1H) 1.66-1.74 (m, 1H) 2.53-2.69 (m, 2H) 3.83-4.00 (m, 2H) 4.27-4.33 (m, 1H) 5.29-5.33 (m, 1H) 7.28-7.33 (m, 2H) 7.34-7.39 (m, 2H)

Intermediate 42:
(4-Chlorophenyl)(piperidin-4-yl)methanol hydrochloride

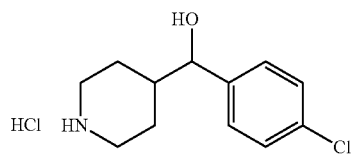 [SMILES: Cl ; OC(c1ccc(Cl)cc1)C1CCNCC1]

Hydrogen chloride (4M in dioxane, 0.614 mL, 2.455 mmol) was added to a solution of tert-butyl 4-((4-chlorophenyl)(hydroxy)methyl)piperidine-1-carboxylate (Intermediate 41, 0.4 g, 1.228 mmol) in Methanol (10 mL). The reaction was stirred at room temperature overnight. The solution was concentrated and azeotroped with toluene to give (4-chlorophenyl)(piperidin-4-yl)methanol hydrochloride (0.305 g, 1.163 mmol, 95% yield) as a cream solid.
$^1$H NMR (400 MHz, DMSO-$d_6$) δ ppm 1.33-1.47 (m, 3H) 1.67-1.84 (m, 2H) 2.74 (br. s., 2H) 3.15-3.27 (m, 2H) 4.33-4.38 (m, 1H) 5.49-5.53 (m, 1H) 7.30-7.35 (m, 2H) 7.37-7.43 (m, 2H) 8.48 (br. s., 1H) 8.93 (br. s., 1H)

Intermediate 43:
4-((4-Chlorophenyl)(methoxy)methyl)piperidine hydrochloride

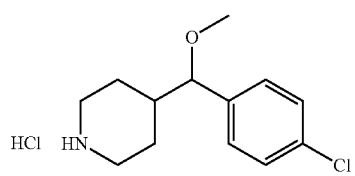 [SMILES: Cl ; COC(c1ccc(Cl)cc1)C1CCNCC1]

Sodium hydride (60% in mineral oil, 0.221 g, 5.52 mmol) was added to a solution of tert-butyl 4-((4-chlorophenyl)(hydroxy)methyl)piperidine-1-carboxylate (Intermediate 41, 0.6 g, 1.841 mmol) in THF (15 mL) under nitrogen at 0° C. The reaction was stirred at room temperature for 45 minutes. The suspension was cooled and methyl iodide (0.345 mL, 5.52 mmol) was added and then stirred at room temperature overnight. The reaction was quenched with methanol and concentrated in vacuo. The crude product was purified by column chromatography on silica, eluted with 0-20% ethyl acetate/petroleum ether to afford tert-butyl 4-((4-chlorophenyl)(methoxy)methyl)piperidine-1-carboxylate (0.545 g, 1.604 mmol, 87% yield) as a colourless oil. Hydrogen chloride (4M in dioxane) (0.802 mL, 3.21 mmol) was added to a solution of tert-butyl 4-((4-chlorophenyl)(methoxy)methyl)piperidine-1-carboxylate (0.545 g, 1.604 mmol) in methanol (10 mL). The reaction was stirred at room temperature overnight. The solution was concentrated in vacuo and azeotroped with toluene to give 4-((4-chlorophenyl)(methoxy)methyl)piperidine hydrochloride (0.480 g, 1.738 mmol, 108% yield) as a white solid.

¹H NMR (400 MHz, DMSO-d₆) δ ppm 1.25-1.49 (m, 3H) 1.77-1.96 (m, 2H) 2.66-2.83 (m, 2H) 3.12 (s, 3H) 3.14-3.29 (m, 2H) 3.98-4.03 (m, 1H) 7.27-7.32 (m, 2H) 7.43-7.49 (m, 2H) 8.33-8.60 (m, 2H)

Intermediate 44: tert-Butyl 4-(1-(4-chlorophenyl)-2-oxoethyl)piperidine-1-carboxylate

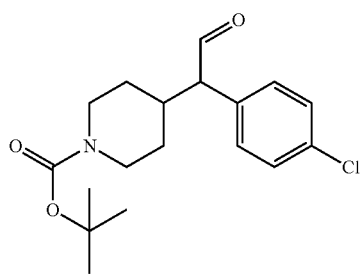 [SMILES: CC(C)(C)OC(=O)N1CCC(C(C=O)c2ccc(Cl)cc2)CC1]

tert-Butyl 4-((4-chlorophenyl)(cyano)methyl)piperidine-1-carboxylate (Intermediate 38, 4 g, 11.95 mmol) was dissolved in toluene (15 mL) and cooled to −28° C., to this was added Diisobutylaluminium hydride (3.40 g, 23.89 mmol). The reaction was stirred at room temperature for 2 hours. The reaction mixture was quenched with ammonium chloride solution then acidified with 6N HCl to pH 2. Organic layer extracted and dried (Na₂SO₄) and concentrated under reduced pressure. The crude product was purified by column chromatography on silica, eluted with 0-50% ethyl acetate/petroleum ether to afford tert-butyl 4-(1-(4-chlorophenyl)-2-oxoethyl)piperidine-1-carboxylate (2 g, 50% yield).

Intermediate 45: tert-Butyl 4-(1-(4-chlorophenyl)-2-hydroxyethyl)piperidine-1-carboxylate

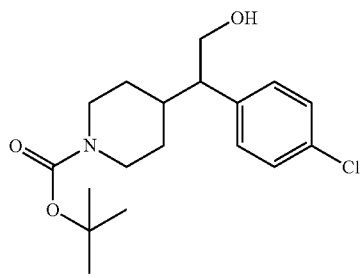 [SMILES: CC(C)(C)OC(=O)N1CCC(C(CO)c2ccc(Cl)cc2)CC1]

tert-Butyl 4-(1-(4-chlorophenyl)-2-oxoethyl)piperidine-1-carboxylate (Intermediate 44, 0.7 g, 2.072 mmol) was dissolved in MeOH (20 mL) and cooled to 0-5° C., to this was added sodium borohydride (0.157 g, 4.14 mmol). The reaction was stirred at room temperature for 2 hours. The reaction mixture was concentrated under reduced pressure and DCM added, followed by water. The aqueous layer was extracted with DCM. Organic layer dried (Na₂SO₄), filtered and concentrated under reduced pressure. The crude product was purified by column chromatography on silica, eluted with 0-50% ethyl acetate/petroleum ether to afford tert-butyl 4-(1-(4-chlorophenyl)-2-hydroxyethyl)piperidine-1-carboxylate (0.7 g, 35%).

Intermediate 46: 4-((4-Chlorophenyl)(ethoxy)methyl)piperidine hydrochloride

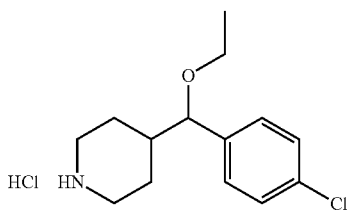 [SMILES: Cl ; CCOC(c1ccc(Cl)cc1)C1CCNCC1]

Sodium hydride (60% in mineral oil, 0.074 g, 1.841 mmol) was added to a solution of tert-butyl 4-((4-chlorophenyl)(hydroxy)methyl)piperidine-1-carboxylate (Intermediate 41, 0.5 g, 1.535 mmol) in THF (15 mL) under nitrogen at 0° C. The reaction was stirred at room temperature for 1.5 hours. Iodoethane (0.370 mL, 4.60 mmol) was added and the suspension stirred at room temperature overnight. An additional portion of iodoethane (0.370 mL, 4.60 mmol) was added and stirred over the weekend. The reaction was quenched with methanol and concentrated in vacuo. The crude product was purified by column chromatography on silica, eluted with 0-20% ethyl acetate/petroleum ether to afford tert-butyl 4-((4-chlorophenyl)(ethoxy)methyl)piperidine-1-carboxylate (0.445 g, 1.257 mmol, 82% yield) as a colourless oil. Hydrogen chloride (4M in dioxane) (0.629 ml, 2.51 mmol) was added to a solution of tert-butyl 4-((4-chlorophenyl)(ethoxy)methyl)piperidine-1-carboxylate (0.445 g, 1.257 mmol) in Methanol (5 mL). The reaction was stirred at room temperature overnight. The solution was concentrated and azeotroped with toluene to give 4-((4-chlorophenyl)(ethoxy)methyl)piperidine hydrochloride (0.394 g, 1.358 mmol, 108% yield) as a colourless gum.

¹H NMR (400 MHz, DMSO-d₆) δ ppm 1.04-1.13 (m, 3H) 1.30-1.47 (m, 3H) 1.73-1.97 (m, 2H) 2.30 (s, 1H) 2.65-2.83 (m, 2H) 3.12-3.28 (m, 3H) 4.04-4.14 (m, 1H) 7.26-7.35 (m, 2H) 7.40-7.49 (m, 2H) 8.74 (br. s., 2H)

Intermediate 47: 4-((4-Chlorophenyl)fluoromethyl)piperidine hydrochloride

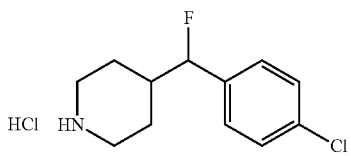 [SMILES: Cl ; FC(c1ccc(Cl)cc1)C1CCNCC1]

Diethylaminosulfurtrifluoride (0.405 mL, 3.07 mmol) was added to a solution of tert-butyl 4-((4-chlorophenyl)(hydroxy)methyl)piperidine-1-carboxylate (Intermediate 41, 0.5 g, 1.535 mmol) in DCM (15 mL) under nitrogen at −78° C. The reaction was stirred at −78° C. for 10 minutes, then at room temperature for 1 hour. The reaction was quenched with saturated aqueous sodium hydrogen carbonate. The aqueous was extracted with DCM. The combined organics were dried (phase separator) and concentrated in vacuo. The crude product was purified by column chromatography on silica, eluted with 0-20% ethyl acetate/petroleum ether to afford tert-butyl 4-((4-chlorophenyl)fluoromethyl)piperidine-1-carboxylate (0.425 g, 1.296 mmol, 84% yield) as a white solid.

$^1$H NMR (400 MHz, DMSO-$d_6$) δ ppm 1.41-1.59 (m, 3H) 1.77-1.90 (m, 1H) 2.04-2.20 (m, 1H) 2.71-2.89 (m, 2H) 3.18-3.30 (m, 2H) 5.33-5.52 (m, 1H) 7.34-7.43 (m, 2H) 7.45-7.56 (m, 2H) 8.68 (br. s., 1H) 9.03 (br. s., 1H)

2. EXAMPLES

Example 1 4-(3,4-Dichlorophenoxy)-1-((1,3,5-trimethyl-1H-pyrazol-4-yl)sulfonyl)piperidine

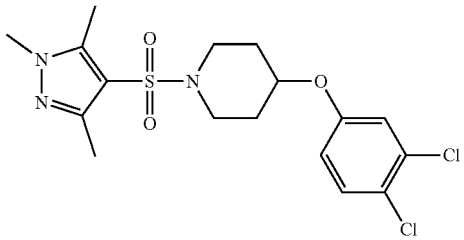

4-(3,4-Dichlorophenoxy)piperidine hydrochloride (143 mg, 0.508 mmol) (prepared as described for 4-(4-chloro-3-fluorophenoxy)piperidine hydrochloride (Intermediate 10) using 3,4-dichlorophenol) and triethylamine (142 μL, 1.16 mmol) in dichloromethane (10 mL) was treated with 1,3,5-trimethyl-1H-pyrazole-4-sulfonyl chloride (106 mg, 0.508 mmol). The reaction was stirred for 2 hours at room temperature. The crude reaction was washed with 1N hydrochloric acid, filtered through a phase separation cartridge and concentrated in vacuo. The crude product was purified by silica column chromatography eluting with petrol/ethyl acetate to give the title compound. (160 mg, 76%)

$^1$H NMR (400 MHz, DMSO-$d_6$) δ ppm 1.62-1.75 (m, 2H) 2.00-2.15 (m, 2H) 2.30 (s, 3H) 2.45 (s, 3H) 2.78-2.86 (m, 2H) 3.34-3.42 (m, 2H) 3.75 (s, 3H) 4.45-4.54 (m, 1H) 6.95-6.98 (m, 1H) 7.28 (s, 1H) 7.24 (m, 1H)

MS ES$^+$: 419.

Example 2 4-(3,4-Dichlorophenoxy)-1-[(3,5-dimethyl-1H-pyrazol-4-yl)sulfonyl]piperidine

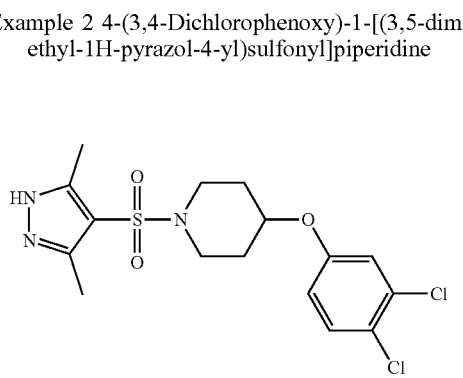

Prepared as described for 4-(3,4-dichlorophenoxy)-1-((1,3,5-trimethyl-1H-pyrazol-4-yl)sulfonyl)piperidine (Example 1) from 3,5-dimethyl-1H-pyrazole-4-sulfonyl chloride (Intermediate 3) and 4-(3,4-dichlorophenoxy)piperidine hydrochloride.

$^1$H NMR (400 MHz, DMSO-$d_6$) δ ppm 1.60-1.75 (m, 2H) 1.98-2.05 (m, 2H) 2.30 (s, 3H) 2.40 (s, 3H) 2.75-2.89 (m, 2H) 3.30-3.40 (m, 2H) 4.48-4.54 (m, 1H) 6.98 (m, 1H) 7.28 (m 1H) 7.48 (m, 1H) 13.0 (s, 1H)

MS ES$^+$: 404.

Example 3 4-[4-(Trifluoromethoxy)phenoxy]-1-[(1,3,5-trimethyl-1H-pyrazol-4-yl)sulfonyl]piperidine

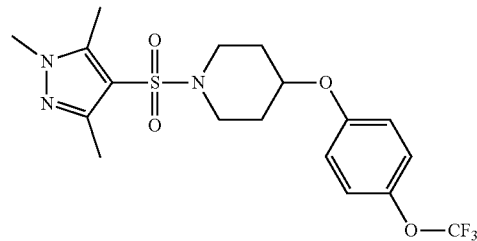 [SMILES: Cc1nn(C)c(C)c1S(=O)(=O)N1CCC(Oc2ccc(OC(F)(F)F)cc2)CC1]

Prepared as described for 4-(3,4-dichlorophenoxy)-1-((1,3,5-trimethyl-1H-pyrazol-4-yl)sulfonyl)piperidine (Example 1) from 1,3,5-trimethyl-1H-pyrazole-4-sulfonyl chloride and 4-(4-(trifluoromethoxy)phenoxy)piperidine hydrochloride (prepared as described for 4-(4-chloro-3-fluorophenoxy)piperidine hydrochloride (Intermediate 10) using 4-(trifluoromethoxy)phenol).

$^1$H NMR (400 MHz, DMSO-$d_6$) δ ppm 1.65-1.75 (m, 2H) 2.00-2.12 (m, 2H) 2.30 (s, 3H) 2.44 (s, 3H) 2.80-2.92 (m, 2H) 3.24-3.33 (m, 2H) 3.76 (s, 3H) 4.45-4.52 (m, 1H) 6.98 (m, 1H) 7.05 (d, J=7.7 Hz 2H) 7.28 (d, J=7.7 Hz 1H)

MS ES$^+$: 434.

Example 4 4-(4-Methylphenoxy)-1-[(1,3,5-trimethyl-1H-pyrazol-4-yl)sulfonyl]piperidine

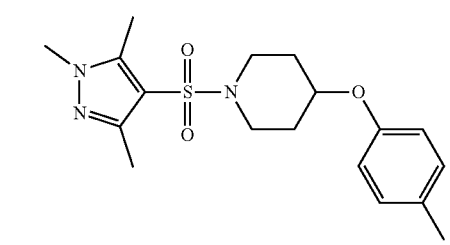

Prepared as described for 4-(3,4-dichlorophenoxy)-1-((1,3,5-trimethyl-1H-pyrazol-4-yl)sulfonyl)piperidine (Example 1) from 1,3,5-trimethyl-1H-pyrazole-4-sulfonyl chloride and 4-(p-tolyloxy)piperidine hydrochloride.

$^1$H NMR (400 MHz, DMSO-$d_6$) δ ppm 1.57-1.72 (m, 2H) 1.91-2.04 (m, 2H) 2.21 (s, 3H) 2.26 (s, 3H) 2.41 (s, 3H) 2.77-2.88 (m, 2H) 3.18-3.30 (m, 2H) 3.73 (s, 3H) 4.31-4.42 (m, 1H) 6.77-6.86 (m, 2H) 6.99-7.11 (m, 2H)

MS ES$^+$: 364.

Example 5 4-(4-Chlorophenoxy)-1-[(1,3,5-trimethyl-1H-pyrazol-4-yl)sulfonyl]piperidine

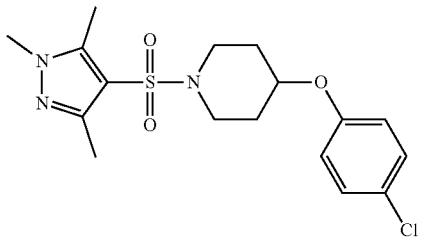 [SMILES: Cc1nn(C)c(C)c1S(=O)(=O)N1CCC(Oc2ccc(Cl)cc2)CC1]

Prepared as described for 4-(3,4-dichlorophenoxy)-1-((1,3,5-trimethyl-1H-pyrazol-4-yl)sulfonyl)piperidine (Example 1) from 1,3,5-trimethyl-1H-pyrazole-4-sulfonyl chloride and 4-(4-chlorophenoxy)piperidine hydrochloride.

$^1$H NMR (400 MHz, DMSO-$d_6$) δ ppm 1.60-1.73 (m, 2H) 1.94-2.05 (m, 2H) 2.26 (s, 3H) 2.41 (s, 3H) 2.77-2.86 (m, 2H) 3.23-3.31 (m, 2H) 3.73 (s, 3H) 4.39-4.47 (m, 1H) 6.92-6.99 (m, 2H) 7.26-7.32 (m, 2H)

MS ES$^+$: 384.

Example 6 4-(3-Chlorophenoxy)-1-[(1,3,5-trimethyl-1H-pyrazol-4-yl)sulfonyl]piperidine

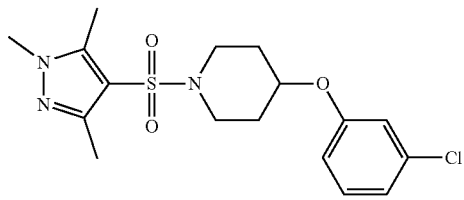 [SMILES: Cc1nn(C)c(C)c1S(=O)(=O)N1CCC(Oc2cccc(Cl)c2)CC1]

Prepared as described for 4-(3,4-dichlorophenoxy)-1-((1,3,5-trimethyl-1H-pyrazol-4-yl)sulfonyl)piperidine (Example 1) from 1,3,5-trimethyl-1H-pyrazole-4-sulfonyl chloride and 4-(3-chlorophenoxy)piperidine hydrochloride.

$^1$H NMR (400 MHz, DMSO-$d_6$) δ ppm 1.60-1.72 (m, 2H) 2.02-2.18 (m, 2H) 2.28 (s, 3H) 2.42 (s, 3H) 2.80-2.92 (m, 2H) 3.06-3.15 (m, 2H) 3.72 (s, 3H) 4.40-4.54 (m, 1H) 6.92 (d, 1H) 7.02 (d, 1H) 7.10 (s, 1H) 7.28 (m, 1H)

MS ES$^+$: 384.

Example 7 4-({1-[(1,3,5-Trimethyl-1H-pyrazol-4-yl)sulfonyl]piperidin-4-yl}oxy)benzonitrile

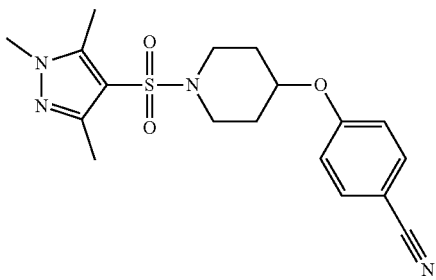 [SMILES: Cc1nn(C)c(C)c1S(=O)(=O)N1CCC(Oc2ccc(C#N)cc2)CC1]

Prepared as described for 4-(3,4-dichlorophenoxy)-1-((1,3,5-trimethyl-1H-pyrazol-4-yl)sulfonyl)piperidine (Example 1) from 1,3,5-trimethyl-1H-pyrazole-4-sulfonyl chloride and 4-(piperidin-4-yloxy)benzonitrile hydrochloride.

$^1$H NMR (400 MHz, DMSO-$d_6$) δ ppm 1.68-1.78 (m, 2H) 2.04-2.12 (m, 2H) 2.30 (s, 3H) 2.45 (s, 3H) 2.80-2.89 (m, 2H) 3.30-3.42 (m, 2H) 3.75 (s 3H) 4.58-4.60 (m, 1H) 7.12 (d, J=7.8 Hz 2H) 7.75 (d, J=7.8 Hz 2H)

MS ES$^+$: 375.

Example 8 4-(4-Chlorophenoxy)-1-[(3,5-dimethyl-1H-pyrazol-4-yl)sulfonyl]piperidine

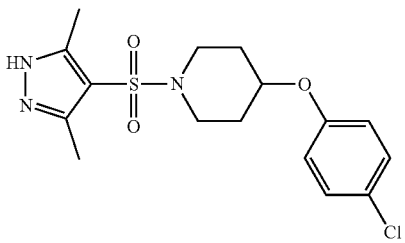

Prepared as described for 4-(3,4-dichlorophenoxy)-1-[(1,3,5-trimethyl-1H-pyrazol-4-yl)sulfonyl]piperidine (Example 1) from 3,5-dimethyl-1H-pyrazole-4-sulfonyl chloride (Intermediate 3) and 4-(4-chlorophenoxy)piperidine hydrochloride (prepared as described for 4-(4-chloro-3-fluorophenoxy)piperidine hydrochloride (Intermediate 10) using 4-chlorophenol).

$^1$H NMR (400 MHz, DMSO-$d_6$) δ ppm 1.60-1.73 (m, 2H) 1.98-2.06 (m, 2H) 2.35 (s, 3H) 2.54 (s, 3H) 2.80-2.88 (m, 2H) 3.28-3.35 (m, 2H) 4.42-4.50 (m, 1H) 6.98 (d, J=7.8 Hz 2H) 7.30 (d, J=7.8 Hz 2H)

MS ES$^+$: 370.

Example 9 1-[(1-Ethyl-3,5-dimethyl-1H-pyrazol-4-yl)sulfonyl]-4-(4-methylphenoxy)piperidine

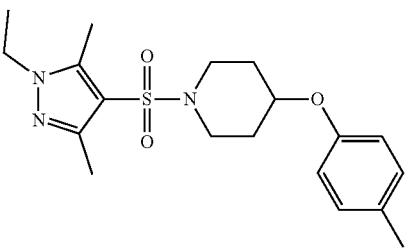 [SMILES: CCn1nc(C)c(S(=O)(=O)N2CCC(Oc3ccc(C)cc3)CC2)c1C]

Prepared as described for 4-(3,4-dichlorophenoxy)-1-[(1,3,5-trimethyl-1H-pyrazol-4-yl)sulfonyl]piperidine (Example 1) from 1-ethyl-3,5-dimethyl-1H-pyrazole-4-sulfonyl chloride and 4-(p-tolyloxy)piperidine hydrochloride.

$^1$H NMR (400 MHz, DMSO-$d_6$) δ ppm 1.30 (t 3H) 1.60-1.71 (m, 2H) 1.95-2.05 (m, 2H) 2.21 (s, 3H) 2.30 (s, 3H) 2.45 (s, 3H) 2.80-2.88 (m, 2H) 3.25-3.30 (m, 2H) 4.05-4.10 (q, 1H) 4.36-4.40 (m, 2H) 6.80 (d, J=7.8 Hz 2H) 7.07 (d, J=7.8 Hz 2H)

MS ES$^+$: 378.

Example 10 1-{[1,5-Dimethyl-3-(trifluoromethyl)-1H-pyrazol-4-yl]sulfonyl}-4-(4-methylphenoxy)piperidine

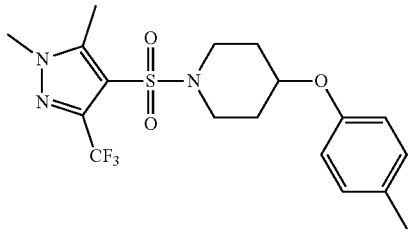

Prepared as described for 4-(3,4-dichlorophenoxy)-1-[(1,3,5-trimethyl-1H-pyrazol-4-yl)sulfonyl]piperidine (Example 1) from 3-(trifluoromethyl)-1,5-dimethyl-1H-pyrazole (Intermediate 6) and 4-(p-tolyloxy)piperidine hydrochloride.

$^1$H NMR (400 MHz, DMSO-$d_6$) δ ppm 1.60-1.71 (m, 2H) 1.95-2.05 (m, 2H) 2.25 (s, 3H) 2.52 (s, 3H) 2.95-3.04 (m, 2H) 3.33-3.40 (m, 2H) 3.90 (s, 3H) 4.38-4.45 (m, 1H) 6.83 (d, J=7.8 Hz 2H) 7.07 (d, J=7.8 Hz 2H)

MS ES$^+$: 418.

Example 11 1-[(5-Chloro-1,3-dimethyl-1H-pyrazol-4-yl)sulfonyl]-4-(4-methylphenoxy)piperidine

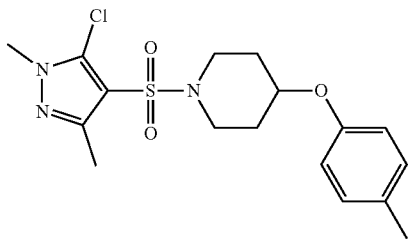

Prepared as described for 4-(3,4-dichlorophenoxy)-1-[(1,3,5-trimethyl-1H-pyrazol-4-yl)sulfonyl]piperidine (Example 1) from 5-chloro-1,3-dimethyl-1H-pyrazole-4-sulfonyl chloride and 4-(p-tolyloxy)piperidine hydrochloride.

$^1$H NMR (400 MHz, DMSO-$d_6$) δ ppm 1.62-1.74 (m, 2H) 2.00-2.08 (m, 2H) 2.28 (s, 3H) 2.42 (s, 3H) 2.80-2.88 (m, 2H) 3.28-3.35 (m, 2H) 3.74 (s, 3H) 4.40-4.48 (m, 1H) 6.95 (d, J=7.8 Hz 2H) 7.30 (d, J=7.8 Hz 2H)

MS ES$^+$: 384.

Example 12 4-[4-(Trifluoromethyl)phenoxy]-1-[(1,3,5-trimethyl-1H-pyrazol-4-yl)sulfonyl]piperidine

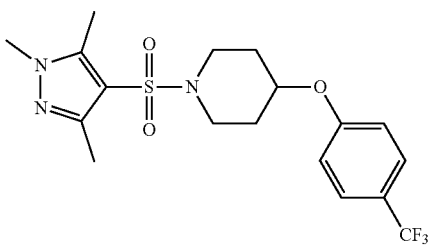 [SMILES: Cc1nn(C)c(C)c1S(=O)(=O)N1CCC(Oc2ccc(C(F)(F)F)cc2)CC1]

Prepared as described for 4-(3,4-dichlorophenoxy)-1-[(1,3,5-trimethyl-1H-pyrazol-4-yl)sulfonyl]piperidine (Example 1) from 1,3,5-trimethyl-1H-pyrazole-4-sulfonyl chloride and 4-(4-trifluoromethyl)phenoxypiperidine hydrochloride (Intermediate 17).

$^1$H NMR (400 MHz, DMSO-$d_6$) δ ppm 1.66-1.76 (m, 2H) 2.05-2.12 (m, 2H) 2.30 (s, 3H) 2.45 (s, 3H) 2.81-2.90 (m, 2H) 3.25-3.35 (m, 2H) 3.72 (s, 3H) 4.58-4.62 (m, 1H) 7.15 (d, J=7.8 Hz 2H) 7.64 (d, J=7.8 Hz 2H)

MS ES$^+$: 418.

Example 13 4-(2,4-Dichlorophenoxy)-1-[(1,3,5-trimethyl-1H-pyrazol-4-yl)sulfonyl]piperidine

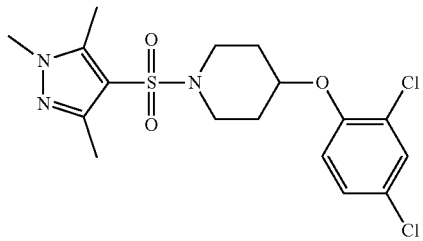

Prepared as described for 4-(3,4-dichlorophenoxy)-1-[(1,3,5-trimethyl-1H-pyrazol-4-yl)sulfonyl]piperidine (Example 1) from 1,3,5-trimethyl-1H-pyrazole-4-sulfonyl chloride and 4-(2,4-dichlorophenoxy)piperidine hydrochloride.

$^1$H NMR (400 MHz, DMSO-$d_6$) δ ppm 1.72-1.81 (m, 2H) 1.96-2.01 (m, 2H) 2.28 (s, 3H) 2.42 (s, 3H) 2.95-3.01 (m, 2H) 3.09-3.18 (m, 2H) 3.72 (s, 3H) 4.60-4.68 (m, 1H) 7.26 (d, 1H) 7.34 (m, 1H) 7.55 (s, 1H)

MS ES$^+$: 418.

Example 14 4-(4-Bromo-2-fluorophenoxy)-1-[(1,3,5-trimethyl-1H-pyrazol-4-yl)sulfonyl]piperidine

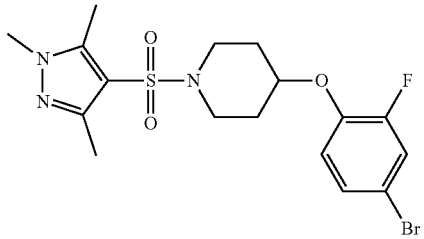 [SMILES: Cc1nn(C)c(C)c1S(=O)(=O)N1CCC(Oc2ccc(Br)cc2F)CC1]

Prepared as described for 4-(3,4-dichlorophenoxy)-1-[(1,3,5-trimethyl-1H-pyrazol-4-yl)sulfonyl]piperidine (Example 1) from 1,3,5-trimethyl-1H-pyrazole-4-sulfonyl chloride and 4-(4-bromo-2-fluorophenoxy)piperidine hydrochloride.

$^1$H NMR (400 MHz, DMSO-$d_6$) δ ppm 1.68-1.78 (m, 2H) 1.95-2.08 (m, 2H) 2.28 (s, 3H) 2.43 (s, 3H) 2.80-2.90 (m, 2H) 3.24-3.30 (m, 2H) 3.75 (s, 3H) 4.45-4.50 (m, 1H) 7.20 (m, 1H) 7.30 (m, 1H) 7.85 (m, 1H)

MS ES$^+$: 448.

Example 15 1-[(5-Chloro-1,3-dimethyl-1H-pyrazol-4-yl)sulfonyl]-4-(4-chlorophenoxy)piperidine

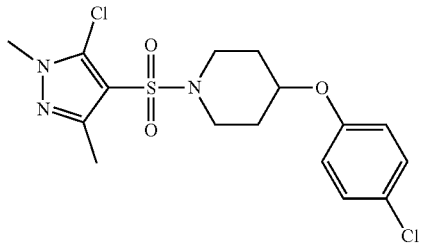 [SMILES: Cc1nn(C)c(Cl)c1S(=O)(=O)N1CCC(Oc2ccc(Cl)cc2)CC1]

Prepared as described for 4-(3,4-dichlorophenoxy)-1-[(1,3,5-trimethyl-1H-pyrazol-4-yl)sulfonyl]piperidine (Example 1) from 5-chloro-1,3-dimethyl-1H-pyrazole-4-sulfonyl chloride and 4-(4-chlorophenoxy)piperidine hydrochloride.

$^1$H NMR (400 MHz, DMSO-$d_6$) δ ppm 1.62-1.70 (m, 2H) 1.95-2.06 (m, 2H) 2.35 (s, 3H) 2.90-3.00 (m, 2H) 3.30-3.40 (m, 2H) 3.84 (s, 3H) 4.45-4.50 (m, 1H) 6.95 (d, J=7.8 Hz 2H) 7.30 (d, J=7.8 Hz 2H)

MS ES$^+$: 404.

Example 16 4-(4-Chlorophenoxy)-1-{[1,5-dimethyl-3-(trifluoromethyl)-1H-pyrazol-4-yl]sulfonyl}piperidine

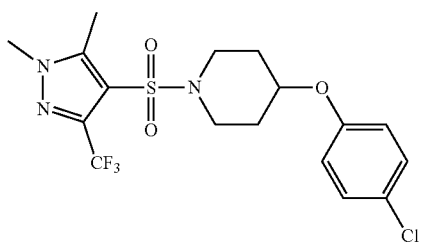

Prepared as described for 4-(3,4-dichlorophenoxy)-1-[(1,3,5-trimethyl-1H-pyrazol-4-yl)sulfonyl]piperidine (Example 1) from 3-(trifluoromethyl)-1,5-dimethyl-1H-pyrazole (Intermediate 6) and 4-(4-chlorophenoxy)piperidine hydrochloride.

$^1$H NMR (400 MHz, DMSO-$d_6$) δ ppm 1.64-1.75 (m, 2H) 1.97-2.06 (m, 2H) 2.50 (s, 3H) 2.95-3.04 (m, 2H) 3.30-3.40 (m, 2H) 3.90 (s, 3H) 4.45-4.50 (m, 1H) 6.95 (d, J=7.8 Hz 2H) 7.32 (d, J=7.8 Hz 2H)

MS ES$^+$: 438.

Example 17 4-(3-Methoxyphenoxy)-1-[(1,3,5-trimethyl-1H-pyrazol-4-yl)sulfonyl]piperidine

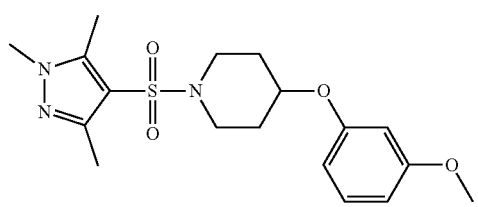

Prepared as described for 4-(3,4-dichlorophenoxy)-1-[(1,3,5-trimethyl-1H-pyrazol-4-yl)sulfonyl]piperidine (Example 1) from 1,3,5-trimethyl-1H-pyrazole-4-sulfonyl chloride and 4-(3-methoxyphenoxy)piperidine hydrochloride $^1$H NMR (400 MHz, DMSO-$d_6$) δ ppm 1.60-1.72 (m, 2H) 1.95-2.05 (m, 2H) 2.28 (s, 3H) 2.42 (s, 3H) 2.78-2.86 (m, 2H) 3.28-3.35 (m, 5H) 3.78 (s, 3H) 4.40-4.50 (m, 1H) 6.46-6.53 (m, 3H) 7.15 (t, 1H)

MS ES$^+$: 380.

Example 18 4-(4-Methoxyphenoxy)-1-[(1,3,5-trimethyl-1H-pyrazol-4-yl)sulfonyl]piperidine

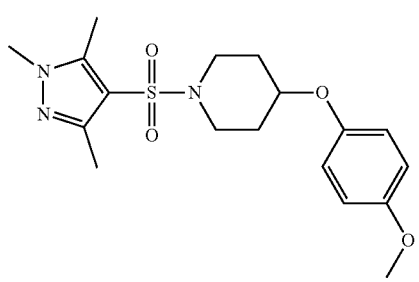 [SMILES: COc1ccc(OC2CCN(S(=O)(=O)c3c(C)nn(C)c3C)CC2)cc1]

Prepared as described for 4-(3,4-dichlorophenoxy)-1-[(1,3,5-trimethyl-1H-pyrazol-4-yl)sulfonyl]piperidine (Example 1) from 1,3,5-trimethyl-1H-pyrazole-4-sulfonyl chloride and 4-(4-methoxyphenoxy)piperidine hydrochloride.

$^1$H NMR (400 MHz, DMSO-$d_6$) δ ppm 1.60-1.70 (m, 2H) 1.95-2.00 (m, 2H) 2.28 (s, 3H) 2.43 (s, 3H) 2.80-2.90 (m, 2H) 3.22-3.28 (m, 2H) 3.70-3.80 (m, 6H) 4.28-4.32 (m, 1H) 6.85 (m, 4H)

MS ES$^+$: 380.

Example 19 4-Phenoxy-1-[(1,3,5-trimethyl-1H-pyrazol-4-yl)sulfonyl]piperidine

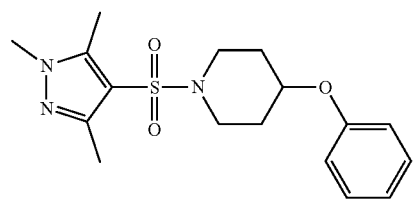 [SMILES: Cc1nn(C)c(C)c1S(=O)(=O)N1CCC(Oc2ccccc2)CC1]

Prepared as described for 4-(3,4-dichlorophenoxy)-1-[(1,3,5-trimethyl-1H-pyrazol-4-yl)sulfonyl]piperidine (Example 1) from 1,3,5-trimethyl-1H-pyrazole-4-sulfonyl chloride and 4-phenoxypiperidine hydrochloride.

$^1$H NMR (400 MHz, DMSO-$d_6$) δ ppm 1.59-1.74 (m, 2H) 1.96-2.07 (m, 2H) 2.27 (s, 3H) 2.42 (s, 3H) 2.76-2.89 (m, 2H) 3.22-3.30 (m, 2H) 3.73 (s, 3H) 4.39-4.50 (m, 1H) 6.85-6.97 (m, 3H) 7.21-7.31 (m, 2H)

MS ES$^+$: 350.

Example 20 4-(4-Fluorophenoxy)-1-[(1,3,5-trimethyl-1H-pyrazol-4-yl)sulfonyl]piperidine

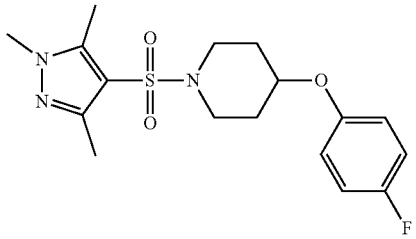 [SMILES: Cc1nn(C)c(C)c1S(=O)(=O)N1CCC(Oc2ccc(F)cc2)CC1]

Prepared as described for 4-(3,4-dichlorophenoxy)-1-[(1,3,5-trimethyl-1H-pyrazol-4-yl)sulfonyl]piperidine (Example 1) from 1,3,5-trimethyl-1H-pyrazole-4-sulfonyl chloride and 4-(4-fluorophenoxy)piperidine hydrochloride.

$^1$H NMR (400 MHz, DMSO-d$_6$) δ ppm 1.59-1.72 (m, 2H) 1.94-2.04 (m, 2H) 2.26 (s, 3H) 2.41 (s, 3H) 2.76-2.88 (m, 2H) 3.22-3.29 (m, 2H) 3.73 (s, 3H) 4.32-4.43 (m, 1H) 6.90-6.98 (m, 2H) 7.03-7.14 (m, 2H)

MS ES$^+$: 368.

Example 21 4-(4-Chlorophenoxy)-3-methyl-1-[(1,3,5-trimethyl-1H-pyrazol-4-yl)sulfonyl]piperidine

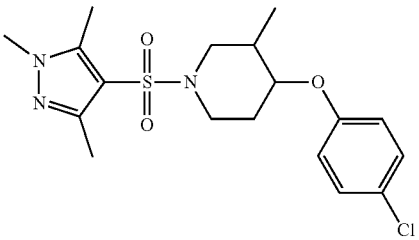 [SMILES: Cc1nn(C)c(C)c1S(=O)(=O)N1CCC(Oc2ccc(Cl)cc2)C(C)C1]

Prepared as described for 4-(3,4-dichlorophenoxy)-1-[(1,3,5-trimethyl-1H-pyrazol-4-yl)sulfonyl]piperidine (Example 1) from 1,3,5-trimethyl-1H-pyrazole-4-sulfonyl chloride and 4-(4-chlorophenoxy)-3-methylpiperidine hydrochloride (Intermediate 20).

$^1$H NMR (400 MHz, CDCl$_3$) δ ppm 1.07 (d, J=6.78, 3H) 1.68-1.77 (m, 1H) 2.03-2.15 (m, 2H) 2.39 (s, 3H) 2.47 (s, 3H) 2.55-2.59 (m, 1H) 2.80-2.86 (m, 1H) 3.42-3.49 (m, 2H), 3.77 (s, 3H) 3.81-3.86 (m, 1H) 6.78 (d, J=9.03, 2H) 7.21 (d, J=9.03, 2H)

MS ES$^+$: 398.

Example 22 4-(2,4-Dichlorophenoxy)-1-[(3,5-dimethyl-1H-pyrazol-4-yl)sulfonyl]piperidine

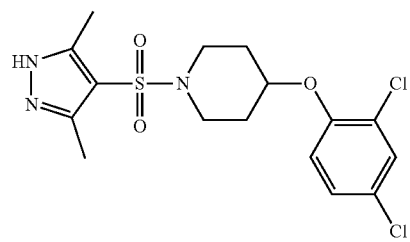 [SMILES: Cc1n[nH]c(C)c1S(=O)(=O)N1CCC(Oc2ccc(Cl)cc2Cl)CC1]

Prepared as described for 4-(3,4-dichlorophenoxy)-1-[(1,3,5-trimethyl-1H-pyrazol-4-yl)sulfonyl]piperidine (Example 1) from 3,5-dimethyl-1H-pyrazole-4-sulfonyl chloride (Intermediate 3) and 4-(2,4-dichlorophenoxy)piperidine hydrochloride.

$^1$H NMR (400 MHz, DMSO-d$_6$) δ ppm 1.72-1.84 (m, 2H) 1.90-2.02 (m, 2H) 2.32 (s, 6H) 2.96-3.04 (m, 2H) 3.08-3.18 (m, 2H) 4.59-4.66 (m, 1H) 7.25 (m, 1H) 7.33 (m, 1H) 7.55 (s, 1H) 9.45 (br.s, 1H)

MS ES$^+$: 404.

Example 23 4-(Naphthalen-2-yloxy)-1-[(1,3,5-trimethyl-1H-pyrazol-4-yl)sulfonyl]piperidine

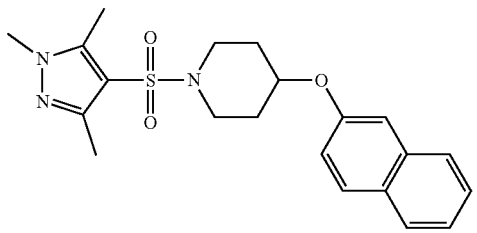 [SMILES: Cc1nn(C)c(C)c1S(=O)(=O)N1CCC(Oc2ccc3ccccc3c2)CC1]

Prepared as described for 4-(3,4-dichlorophenoxy)-1-[(1,3,5-trimethyl-1H-pyrazol-4-yl)sulfonyl]piperidine (Example 1) from 1,3,5-trimethyl-1H-pyrazole-4-sulfonyl chloride and 4-(naphthalen-2-yloxy)piperidine hydrochloride.

$^1$H NMR (400 MHz, Dichloromethane-d$_2$) δ ppm 1.94-2.19 (m, 4H) 2.34-2.41 (s, 3H) 2.46-2.52 (s, 3H) 3.12-3.35 (m, 4H) 3.71-3.81 (s, 3H) 4.60 (m, 1H) 7.09-7.21 (m, 2H) 7.32-7.43 (m, 1H) 7.47 (t, J=7.07 Hz, 1H) 7.68-7.85 (m, 3H)

MS ES$^+$: 400.

Example 24 4-(4-Chlorophenoxy)-2-methyl-1-[(1,3,5-trimethyl-1H-pyrazol-4-yl)sulfonyl]piperidine

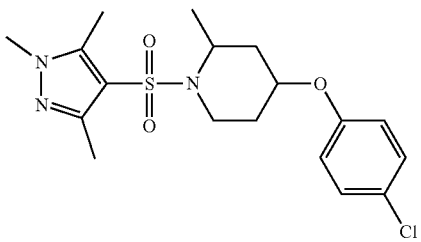 [SMILES: Cc1nn(C)c(C)c1S(=O)(=O)N1CCC(Oc2ccc(Cl)cc2)CC1C]

Prepared as described for 4-(3,4-dichlorophenoxy)-1-[(1,3,5-trimethyl-1H-pyrazol-4-yl)sulfonyl]piperidine (Example 1) from 1,3,5-trimethyl-1H-pyrazole-4-sulfonyl chloride and 4-(4-chlorophenoxy)-2-methylpiperidine hydrochloride (Intermediate 19).

$^1$H NMR (400 MHz, CDCl$_3$) δ ppm 1.31 (d, J=7.12 3 H) 1.76-1.85 (m, 1H) 1.91-2.02 (m, 3H) 2.45 (s, 3H) 2.36 (m, 3H) 3.39-3.56 (m, 2H) 3.74 (s, 3H) 4.10-4.17 (m, 1H) 4.61-4.64 (m, 1H) 6.78 (d, J=9.00 2 H) 7.23 (d, J=9.00 2 H)

MS ES$^+$: 398.

Example 25 1-[(5-Chloro-1,3-dimethyl-1H-pyrazol-4-yl)sulfonyl]-4-(2,4-dichlorophenoxy)piperidine

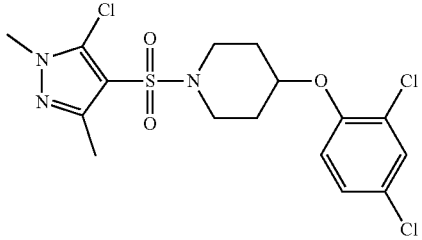 [SMILES: Cc1nn(C)c(Cl)c1S(=O)(=O)N1CCC(Oc2ccc(Cl)cc2Cl)CC1]

Prepared as described for 4-(3,4-dichlorophenoxy)-1-[(1,3,5-trimethyl-1H-pyrazol-4-yl)sulfonyl]piperidine (Example 1) from 5-chloro-1,3-dimethyl-1H-pyrazole-4-sulfonyl chloride and 4-(2,4-dichlorophenoxy)piperidine hydrochloride.

$^1$H NMR (400 MHz, DMSO-d$_6$) δ ppm 1.72-1.84 (m, 2H) 1.95-2.05 (m, 2H) 2.38 (s, 3H) 3.06-3.15 (m, 2H) 3.18-3.24 (m, 2H) 3.84 (s, 3H) 4.64-4.70 (m, 1H) 7.26 (d, 1H) 7.36 (m, 1H) 7.58 (s, 1H)

MS ES$^+$: 440.

Example 26 4-(2,4-Dichlorophenoxy)-1-{[1,3-dimethyl-5-(trifluoromethyl)-1H-pyrazol-4-yl]sulfonyl}piperidine

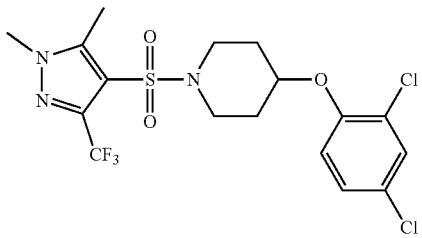 [SMILES: Cc1c(S(=O)(=O)N2CCC(Oc3ccc(Cl)cc3Cl)CC2)c(C(F)(F)F)nn1C]

Prepared as described for 4-(3,4-dichlorophenoxy)-1-[(1,3,5-trimethyl-1H-pyrazol-4-yl)sulfonyl]piperidine (Example 1) from 3-(trifluoromethyl)-1,5-dimethyl-1H-pyrazole (Intermediate 6) and 4-(2,4-dichlorophenoxy)piperidine hydrochloride.

$^1$H NMR (400 MHz, DMSO-d$_6$) δ ppm 1.72-1.80 (m, 2H) 1.96-2.04 (m, 2H) 2.50 (s, 3H) 3.07-3.13 (m, 2H) 3.20-3.28 (m, 2H) 3.90 (s, 3H) 4.60-4.68 (m, 1H) 7.25 (d, J=7.8 Hz 1H) 7.46 (m, 1H) 7.58 (s, 1H)

MS ES$^+$: 472.

Example 27 4-(2,4-Dichlorophenoxy)-1-[(1,3-dimethyl-1H-pyrazol-4-yl)sulfonyl]piperidine

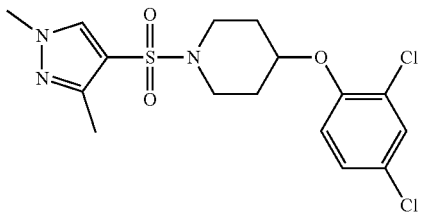 [SMILES: Cc1nn(C)cc1S(=O)(=O)N1CCC(Oc2ccc(Cl)cc2Cl)CC1]

Prepared as described for 4-(3,4-dichlorophenoxy)-1-[(1,3,5-trimethyl-1H-pyrazol-4-yl)sulfonyl]piperidine (Example 1) from 1,3-dimethyl-1H-pyrazole-4-sulfonyl chloride (Intermediate 5) and 4-(2,4-dichlorophenoxy)piperidine hydrochloride.

$^1$H NMR (400 MHz, DMSO-d$_6$) δ ppm 1.72-1.84 (m, 2H) 1.94-2.02 (m, 2H) 2.30 (s, 3H) 2.95-3.12 (m, 4H) 3.80 (s, 3H) 4.64-4.70 (m, 1H) 7.26 (d, J=7.8 Hz 1H) 7.34 (m, 1H) 7.58 (s, 1H) 8.24 (s, 1H)

MS ES$^+$: 404.

Example 28 4-(2,4-Dichlorophenoxy)-1-[(3,5-diethyl-1-methyl-1H-pyrazol-4-yl)sulfonyl]piperidine

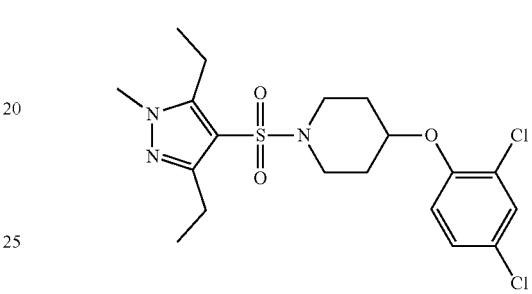

Prepared as described for 4-(3,4-dichlorophenoxy)-1-[(1,3,5-trimethyl-1H-pyrazol-4-yl)sulfonyl]piperidine (Example 1) from 3,5-diethyl-1-methyl-1H-pyrazole-4-sulfonyl chloride (Intermediate 4) and 4-(2,4-dichlorophenoxy)piperidine hydrochloride.

$^1$H NMR (400 MHz, DMSO-d$_6$) δ ppm 1.08-1.20 (m, 6H) 1.70-1.80 (m, 2H) 1.90-2.00 (m, 2H) 2.70 (q, 2H) 2.86 (q, 2H) 2.96-3.02 (m, 2H) 3.10-3.18 (m, 2H) 3.80 (s, 3H) 4.60-4.70 (m, 1H) 7.28 (d, J=7.8 Hz 1H) 7.34 (m, 1H) 7.57 (s, 1H)

MS ES$^+$: 446.

Example 29 4-(2,4-Dichlorophenoxy)-1-{[1-(difluoromethyl)-3,5-dimethyl-1H-pyrazol-4-yl]sulfonyl}piperidine

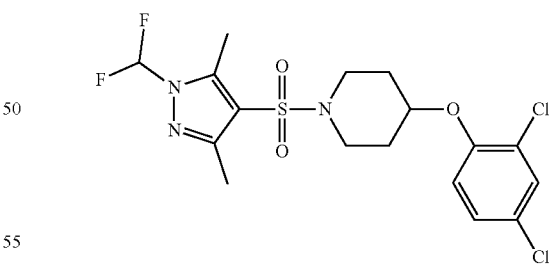

Prepared as described for 4-(3,4-dichlorophenoxy)-1-[(1,3,5-trimethyl-1H-pyrazol-4-yl)sulfonyl]piperidine (Example 1) from 1-(difluoromethyl)-3,5-dimethyl-1H-pyrazole-4-sulfonyl chloride and 4-(2,4-dichlorophenoxy)piperidine hydrochloride.

$^1$H NMR (400 MHz, DMSO-d$_6$) δ ppm 1.67-1.86 (m, 2H) 1.87-2.09 (m, 2H) 2.34 (s, 3H) 2.61 (s, 3H) 3.10 (m, 4H) 4.59-4.78 (m, 1H) 7.19-7.29 (m, 1H) 7.31-7.39 (m, 1H) 7.55 (m, 1H) 7.69-8.10 (m, 1H)

MS ES$^+$: 454.

Example 30 4-(4-Chloro-2-fluorophenoxy)-1-(trimethyl-1H-pyrazole-4-sulfonyl)piperidine

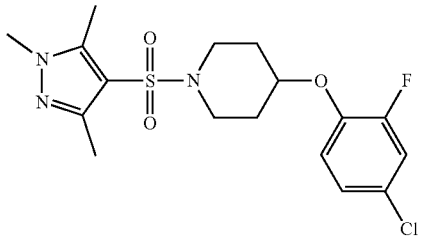 [SMILES: Cc1nn(C)c(C)c1S(=O)(=O)N1CCC(Oc2ccc(Cl)cc2F)CC1]

Prepared as described for 4-(3,4-dichlorophenoxy)-1-[(1,3,5-trimethyl-1H-pyrazol-4-yl)sulfonyl]piperidine (Example 1) from 1,3,5-trimethyl-1H-pyrazole-4-sulfonyl chloride and 4-(4-chloro-2-fluorophenoxy)piperidine hydrochloride (Intermediate 11).

$^1$H NMR (400 MHz, Chloroform-d) δ ppm 1.88-2.10 (m, 4H) 2.40 (s, 3H) 2.48 (s, 3H) 3.09-3.32 (m, 4H) 3.72-3.84 (m, 3H) 4.28-4.42 (m, 1H) 6.82-6.96 (m, 1H) 7.03 (dd, J=8.66, 1.63 Hz, 1H) 7.10 (dd, J=10.79, 2.51 Hz, 1H)

MS ES$^+$: 402.

Example 31 5-Chloro-2-{[1-(trimethyl-1H-pyrazole-4-sulfonyl)piperidin-4-yl]oxy}benzonitrile

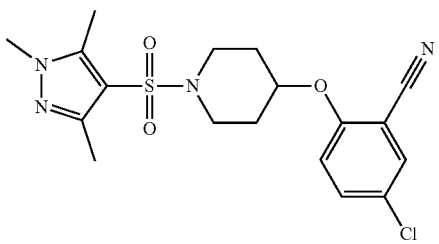 [SMILES: Cc1nn(C)c(C)c1S(=O)(=O)N1CCC(Oc2ccc(Cl)cc2C#N)CC1]

Prepared as described for 4-(3,4-dichlorophenoxy)-1-[(1,3,5-trimethyl-1H-pyrazol-4-yl)sulfonyl]piperidine (Example 1) from 1,3,5-trimethyl-1H-pyrazole-4-sulfonyl chloride and 5-chloro-2-(piperidin-4-yloxy)benzonitrile hydrochloride (Intermediate 12).

$^1$H NMR (400 MHz, Chloroform-d) δ ppm 2.02 (d, J=3.76 Hz, 4H) 2.38 (s, 3H) 2.48 (s, 3H) 2.95-3.18 (m, 2H) 3.30-3.49 (m, 2H) 3.76 (s, 3H) 4.62 (br. s., 1H) 6.90 (d, J=8.78 Hz, 1H) 7.36-7.61 (m, 2H)

MS ES$^+$: 409.

Example 32 1-[(3,5-Dimethyl-1H-pyrazol-4-yl)sulfonyl]-4-[4-(trifluoromethoxy)phenoxy]piperidine

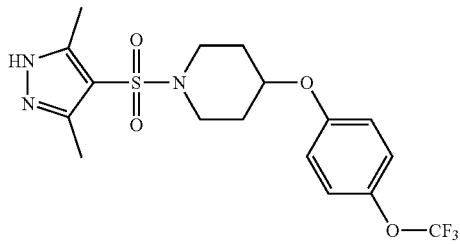 [SMILES: Cc1n[nH]c(C)c1S(=O)(=O)N1CCC(Oc2ccc(OC(F)(F)F)cc2)CC1]

Prepared as described for 4-(3,4-dichlorophenoxy)-1-[(1,3,5-trimethyl-1H-pyrazol-4-yl)sulfonyl]piperidine (Example 1) from 3,5-dimethyl-1H-pyrazole-4-sulfonyl chloride (Intermediate 3) and 4-(4-(trifluoromethoxy)phenoxy)piperidine hydrochloride.

$^1$H NMR (400 MHz, DMSO-d$_6$) δ ppm 1.64-1.72 (m, 2H) 1.98-2.08 (m, 2H) 2.28-2.40 (m, 6H) 2.80-2.88 (m, 2H) 3.24-3.33 (m, 2H) 4.44-4.52 (m, 1H) 7.05 (d, J=7.8 Hz 2H) 7.30 (d, J=7.8 Hz 2H) 13.01 (s, 1H)

MS ES$^+$: 420.

Example 33 1-[(3,5-Dimethyl-1H-pyrazol-4-yl)sulfonyl]-4-(naphthalen-2-yloxy)piperidine

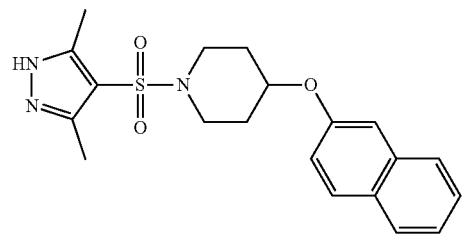 [SMILES: Cc1n[nH]c(C)c1S(=O)(=O)N1CCC(Oc2ccc3ccccc3c2)CC1]

Prepared as described for 4-(3,4-dichlorophenoxy)-1-[(1,3,5-trimethyl-1H-pyrazol-4-yl)sulfonyl]piperidine (Example 1) from 3,5-dimethyl-1H-pyrazole-4-sulfonyl chloride (Intermediate 3) and 4-(naphthalen-2-yloxy)piperidine hydrochloride.

$^1$H NMR (400 MHz, DMSO-d$_6$) δ ppm 1.70-1.80 (m, 2H) 2.10-2.18 (m, 2H) 2.30 (m, 3H) 2.40 (s, 3H) 2.85-2.92 (m, 4H) 4.58-4.68 (m, 1H) 7.12 (m, 1H) 7.30-7.58 (m, 3H) 7.74-7.82 (m, 3H) 13.01 (s, 1H)

MS ES$^+$: 386

Example 34 5-Chloro-2-{[1-(3,5-dimethyl-1H-pyrazole-4-sulfonyl)piperidin-4-yl]oxy}benzonitrile

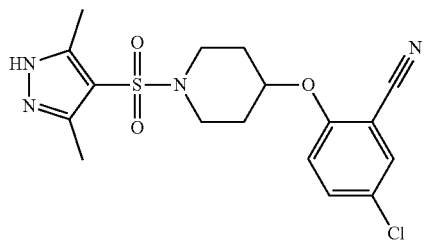 [SMILES: Cc1n[nH]c(C)c1S(=O)(=O)N1CCC(Oc2ccc(Cl)cc2C#N)CC1]

Prepared as described for 4-(3,4-dichlorophenoxy)-1-[(1,3,5-trimethyl-1H-pyrazol-4-yl)sulfonyl]piperidine (Example 1) from 3,5-dimethyl-1H-pyrazole-4-sulfonyl chloride (Intermediate 3) and 5-chloro-2-(piperidin-4-yloxy)benzonitrile hydrochloride (Intermediate 12).

$^1$H NMR (400 MHz, DMSO-d$_6$) δ ppm 1.64-1.86 (m, 2H) 1.91-2.10 (m, 2H) 2.27 (s, 3H) 2.37 (s, 3H) 2.84-3.03 (m, 2H) 3.12-3.27 (m, 2H) 4.61-4.81 (m, 1H) 7.29-7.43 (m, 1H) 7.64-7.76 (m, 1H) 7.90 (s, 1H) 13.09 (br.s, 1H)

MS ES$^+$: 395

Example 35 4-(4-Chloro-2-fluorophenoxy)-1-(3,5-dimethyl-1H-pyrazole-4-sulfonyl)piperidine

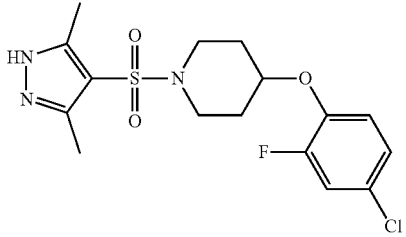 [SMILES: Cc1n[nH]c(C)c1S(=O)(=O)N1CCC(Oc2ccc(Cl)cc2F)CC1]

Prepared as described for 4-(3,4-dichlorophenoxy)-1-[(1,3,5-trimethyl-1H-pyrazol-4-yl)sulfonyl]piperidine (Example 1) from 3,5-dimethyl-1H-pyrazole-4-sulfonyl chloride (Intermediate 3) and 4-(4-chloro-2-fluorophenoxy)piperidine hydrochloride (Intermediate 11). $^1$H NMR (400 MHz, DMSO-$d_6$) δ ppm 1.64-1.80 (m, 2H) 1.93-2.10 (m, 2H) 2.28 (s, 3H) 2.37 (s, 3H) 2.77-2.92 (m, 2H) 3.16-3.27 (m, 2H) 4.40-4.56 (m, 1H) 7.15-7.32 (m, 2H) 7.43 (s, 1H) 13.11 (br. s., 1H)

MS ES$^+$: 388.

Example 36 4-(2,4-Dichlorophenoxy)-1-(1,4-dimethyl-1H-pyrazole-5-sulfonyl)piperidine

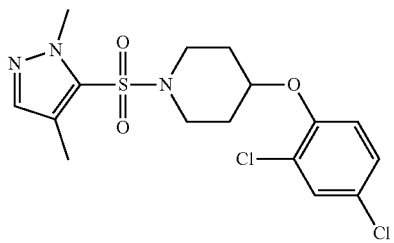 [SMILES: Cc1cnn(C)c1S(=O)(=O)N1CCC(Oc2ccc(Cl)cc2Cl)CC1]

Prepared as described for 4-(3,4-dichlorophenoxy)-1-[(1,3,5-trimethyl-1H-pyrazol-4-yl)sulfonyl]piperidine (Example 1) from 1,4-dimethyl-1H-pyrazole-5-sulfonyl chloride (Intermediate 7) and 4-(2,4-dichlorophenoxy)piperidine hydrochloride.

$^1$H NMR (400 MHz, chloroform-d) δ ppm 2.00 (s, 4H) 2.28 (s, 3H) 3.20-3.35 (m, 2H) 3.37-3.50 (m, 2H) 4.08 (s, 3H) 4.49-4.59 (m, 1H) 6.80-6.90 (m, 1H) 7.14-7.21 (m, 1H) 7.36 (s, 2H)

MS ES$^+$: 404

Example 37 4-(4-Chlorophenoxy)-1-(1,4-dimethyl-1H-pyrazole-5-sulfonyl)piperidine

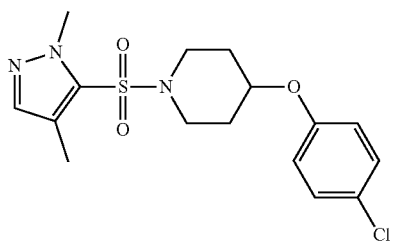 [SMILES: Cc1cnn(C)c1S(=O)(=O)N1CCC(Oc2ccc(Cl)cc2)CC1]

Prepared as described for 4-(3,4-dichlorophenoxy)-1-[(1,3,5-trimethyl-1H-pyrazol-4-yl)sulfonyl]piperidine (Example 1) from 1,4-dimethyl-1H-pyrazole-5-sulfonyl chloride (Intermediate 7) and 4-(4-chlorophenoxy)piperidine hydrochloride.

$^1$H NMR (400 MHz, chloroform-d) δ ppm 1.90-2.03 (m, 4H) 2.27 (s, 3H) 3.25-3.38 (m, 4H) 4.08 (s, 3H) 4.41-4.48 (m, 1H) 6.78-6.82 (m, 2H) 7.20-7.25 (m, 2H) 7.37 (s, 1H)

MS ES$^+$: 370.

Example 38 1-(3,5-Dimethyl-1H-pyrazole-4-sulfonyl)-4-(2,6-dimethylphenoxy)piperidine

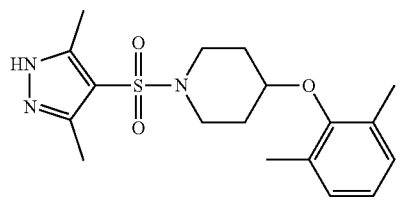 [SMILES: Cc1cccc(C)c1OC1CCN(S(=O)(=O)c2c(C)n[nH]c2C)CC1]

Prepared as described for 4-(3,4-dichlorophenoxy)-1-[(1,3,5-trimethyl-1H-pyrazol-4-yl)sulfonyl]piperidine (Example 1) from 3,5-dimethyl-1H-pyrazole-4-sulfonyl chloride (Intermediate 3) and 4-(2,6-dimethylphenoxy)piperidine hydrochloride.

$^1$H NMR (400 MHz, DMSO-$d_6$) δ ppm 1.61-1.77 (m, 2H) 1.88-2.02 (m, 2H) 2.17 (s, 6H) 2.23-2.39 (m, 6H) 2.54-2.66 (m, 2H) 3.41-3.53 (m, 2H) 3.81-3.93 (m, 1H) 6.83-6.94 (m, 1H) 6.96-7.04 (m, 2H)

MS ES$^+$: 364.

Example 39 4-[4-Chloro-2-(trifluoromethyl)phenoxy]-1-(trimethyl-1H-pyrazole-4-sulfonyl)piperidine

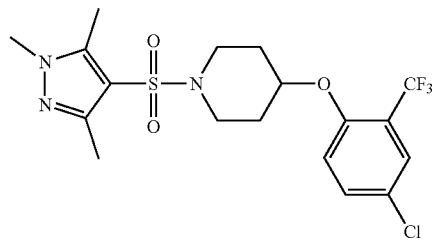 [SMILES: Cc1nn(C)c(C)c1S(=O)(=O)N1CCC(Oc2ccc(Cl)cc2C(F)(F)F)CC1]

Prepared as described for 4-(3,4-dichlorophenoxy)-1-[(1,3,5-trimethyl-1H-pyrazol-4-yl)sulfonyl]piperidine (Example 1) from 1,3,5-trimethyl-1H-pyrazole-4-sulfonyl chloride and 4-(4-chloro-2-(trifluoromethyl)phenoxy)piperidine hydrochloride (Intermediate 14).

$^1$H NMR (400 MHz, DMSO-$d_6$) δ ppm 1.72-1.83 (m, 2H) 1.90-2.03 (m, 2H) 2.25 (s, 3H) 2.40 (s, 3H) 2.91-3.09 (m, 4H) 3.72 (s, 3H) 4.71-4.81 (m, 1H) 7.31-7.40 (m, 1H) 7.60-7.71 (m, 2H)

MS ES$^+$: 452.

Example 40 4-[4-Chloro-2-(trifluoromethyl)phenoxy]-1-(3,5-dimethyl-1H-pyrazole-4-sulfonyl)piperidine

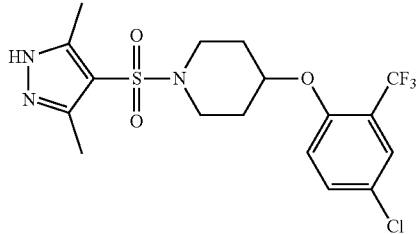 [SMILES: Cc1n[nH]c(C)c1S(=O)(=O)N1CCC(Oc2ccc(Cl)cc2C(F)(F)F)CC1]

Prepared as described for 4-(3,4-dichlorophenoxy)-1-[(1,3,5-trimethyl-1H-pyrazol-4-yl)sulfonyl]piperidine (Example 1) from 3,5-dimethyl-1H-pyrazole-4-sulfonyl chloride (Intermediate 3) and 4-(4-chloro-2-(trifluoromethyl)phenoxy)piperidine hydrochloride (Intermediate 14).

$^1$H NMR (400 MHz, DMSO-$d_6$) δ ppm 1.72-1.85 (m, 2H) 1.88-2.05 (m, 2H) 2.30 (s, 6H) 2.91-3.13 (m, 4H) 4.68-4.85 (m, 1H) 7.32-7.40 (m, 1H) 7.59-7.70 (m, 2H) 13.09 (br. s., 1H)

MS ES$^+$: 438.

Example 41 1-(3,5-Dimethyl-1H-pyrazole-4-sulfonyl)-4-(3-fluoro-4-methoxyphenoxy)piperidine

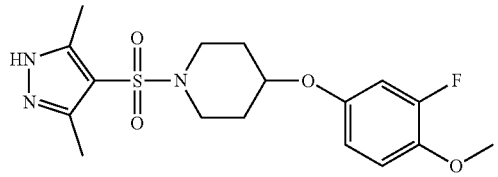 [SMILES: COc1ccc(OC2CCN(S(=O)(=O)c3c(C)n[nH]c3C)CC2)cc1F]

Prepared as described for 4-(3,4-dichlorophenoxy)-1-[(1,3,5-trimethyl-1H-pyrazol-4-yl)sulfonyl]piperidine (Example 1) from 3,5-dimethyl-1H-pyrazole-4-sulfonyl chloride (Intermediate 3) and 4-(3-fluoro-4-methoxyphenoxy)piperidine hydrochloride (Intermediate 13).

$^1$H NMR (400 MHz, DMSO-$d_6$) δ ppm 1.54-1.76 (m, 2H) 1.88-2.05 (m, 2H) 2.32 (s, 6H) 2.70-2.90 (m, 2H) 3.17-3.31 (m, 2H) 3.76 (s, 3H) 4.35 (tt, J=7.91, 3.71 Hz, 1H) 6.62-6.77 (m, 1H) 6.90 (dd, J=13.26, 2.91 Hz, 1H) 6.97-7.15 (m, 1H) 13.05 (br. s., 1H)

MS ES$^+$: 384.

Example 42 4-(3,5-Difluoro-4-methoxyphenoxy)-1-(3,5-dimethyl-1H-pyrazole-4-sulfonyl)piperidine

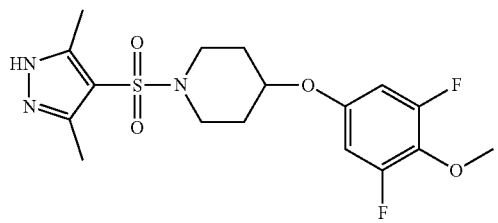 [SMILES: COc1c(F)cc(OC2CCN(S(=O)(=O)c3c(C)n[nH]c3C)CC2)cc1F]

Prepared as described for 4-(3,4-dichlorophenoxy)-1-[(1,3,5-trimethyl-1H-pyrazol-4-yl)sulfonyl]piperidine (Example 1) from 3,5-dimethyl-1H-pyrazole-4-sulfonyl chloride (Intermediate 3) and 4-(3,5-difluoro-4-methoxyphenoxy)piperidine hydrochloride (Intermediate 15).

$^1$H NMR (400 MHz, DMSO-$d_6$) δ ppm 1.54-1.72 (m, 2H) 1.91-2.08 (m, 2H) 2.32 (br. s., 6H) 2.71-2.86 (m, 2H) 3.24-3.31 (m, 2H) 3.80 (s, 3H) 4.28-4.53 (m, 1H) 6.81 (d, J=10.74 Hz, 2H) 13.08 (br. s., 1H)

MS ES$^+$: 402.

Example 43 4-(3-Fluoro-4-methoxyphenoxy)-1-(trimethyl-1H-pyrazole-4-sulfonyl)piperidine

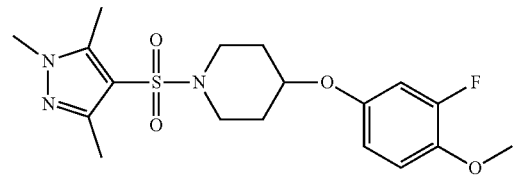

Prepared as described for 4-(3,4-dichlorophenoxy)-1-[(1,3,5-trimethyl-1H-pyrazol-4-yl) sulfonyl]piperidine (Example 1) from 1,3,5-trimethyl-1H-pyrazole-4-sulfonyl chloride and 4-(3-difluoro-4-methoxyphenoxy)piperidine hydrochloride (Intermediate 13). $^1$H NMR (400 MHz, DMSO-$d_6$) δ ppm 1.55-1.73 (m, 2H) 1.88-2.04 (m, 2H) 2.26 (s, 3H) 2.41 (s, 3H) 2.73-2.88 (m, 2H) 3.30 (m, 2H) 3.75 (d, J=12.51 Hz, 6H) 4.34 (tt, J=7.99, 3.76 Hz, 1H) 6.65-6.76 (m, 1H) 6.90 (dd, J=13.26, 2.91 Hz, 1H) 7.04 (t, J=9.47 Hz, 1H)

MS ES$^+$: 398.

Example 44 4-(3,5-Difuoro-4-methoxyphenoxy)-1-(trimethyl-1H-pyrazole-4-sulfonyl)piperidine

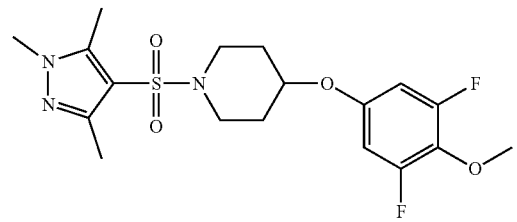

Prepared as described for 4-(3,4-dichlorophenoxy)-1-[(1,3,5-trimethyl-1H-pyrazol-4-yl)sulfonyl]piperidine (Example 1) from 1,3,5-trimethyl-1H-pyrazole-4-sulfonyl chloride and 4-(3,5-difluoro-4-methoxyphenoxy)piperidine hydrochloride (Intermediate 15). $^1$H NMR (400 MHz, DMSO-$d_6$) δ ppm 1.55-1.74 (m, 2H) 1.90-2.05 (m, 2H) 2.26 (s, 3H) 2.41 (s, 3H) 2.70-2.85 (m, 2H) 3.29 (d, J=6.06 Hz, 2H) 3.73 (s, 3H) 3.80 (s, 3H) 4.41 (tt, J=8.21, 3.85 Hz, 1H) 6.68-6.97 (m, 2H)

MS ES$^+$: 416.

Example 45 4-(4-Chloro-3-fluorophenoxy)-1-(trimethyl-1H-pyrazole-4-sulfonyl)piperidine

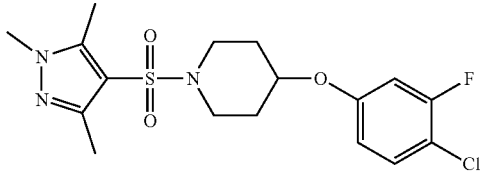 [SMILES: Cc1nn(C)c(C)c1S(=O)(=O)N1CCC(Oc2ccc(Cl)c(F)c2)CC1]

Prepared as described for 4-(3,4-dichlorophenoxy)-1-[(1,3,5-trimethyl-1H-pyrazol-4-yl)sulfonyl]piperidine (Example 1) from 1,3,5-trimethyl-1H-pyrazole-4-sulfonyl chloride and 4-(4-chloro-3-fluorophenoxy)piperidine hydrochloride (Intermediate 10).

$^1$H NMR (400 MHz, DMSO-$d_6$) δ ppm 1.59-1.73 (m, 2H) 1.95-2.07 (m, 2H) 2.26 (s, 3H) 2.41 (s, 3H) 2.71-2.90 (m, 2H) 3.29 (br. s., 2H) 3.63-3.81 (m, 3H) 4.36-4.56 (m, 1H) 6.82 (ddd, J=8.97, 2.84, 1.07 Hz, 1H) 7.10 (dd, J=11.62, 2.78 Hz, 1H) 7.43 (t, J=8.91 Hz, 1H)

MS ES$^+$: 402.

Example 46 4-(4-Chloro-2,6-difluorophenoxy)-1-(trimethyl-1H-pyrazole-4-sulfonyl)piperidine

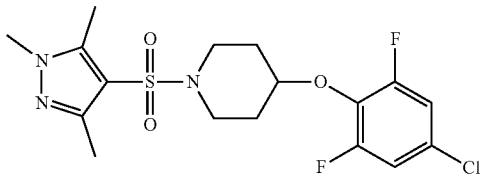 [SMILES: Cc1nn(C)c(C)c1S(=O)(=O)N1CCC(Oc2c(F)cc(Cl)cc2F)CC1]

Prepared as described for 4-(3,4-dichlorophenoxy)-1-[(1,3,5-trimethyl-1H-pyrazol-4-yl)sulfonyl]piperidine (Example 1) from 1,3,5-trimethyl-1H-pyrazole-4-sulfonyl chloride and 4-(4-chloro-2,6-difluorophenoxy)piperidine hydrochloride (Intermediate 16).

$^1$H NMR (400 MHz, DMSO-$d_6$) δ ppm 1.66-1.82 (m, 2H) 1.88-2.03 (m, 2H) 2.25 (s, 3H) 2.40 (s, 3H) 2.89 (ddd, J=11.53, 7.99, 3.47 Hz, 2H) 3.09-3.25 (m, 2H) 3.72 (s, 3H) 4.23 (dt, J=7.26, 3.69 Hz, 1H) 7.31-7.53 (m, 2H)

MS ES$^+$: 420.

Example 47 4-(4-Chloro-3-fluorophenoxy)-1-(3,5-dimethyl-1H-pyrazole-4-sulfonyl)piperidine

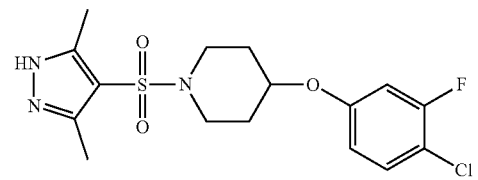 [SMILES: Cc1n[nH]c(C)c1S(=O)(=O)N1CCC(Oc2ccc(Cl)c(F)c2)CC1]

Prepared as described for 4-(3,4-dichlorophenoxy)-1-[(1,3,5-trimethyl-1H-pyrazol-4-yl)sulfonyl]piperidine (Example 1) from 3,5-dimethyl-1H-pyrazole-4-sulfonyl chloride (Intermediate 3) and 4-(4-chloro-3-fluorophenoxy)piperidine hydrochloride (Intermediate 10).

$^1$H NMR (400 MHz, DMSO-$d_6$) δ ppm 1.55-1.77 (m, 2H) 1.91-2.06 (m, 2H) 2.33 (br. s., 6H) 2.70-2.93 (m, 2H) 3.22-3.31 (m, 2H) 4.47 (tt, J=8.16, 3.84 Hz, 1H) 6.82 (ddd, J=8.97, 2.78, 1.01 Hz, 1H) 7.10 (dd, J=11.68, 2.84 Hz, 1H) 7.43 (t, J=8.91 Hz, 1H) 13.08 (br. s., 1H)

MS ES$^+$: 388

Example 48 5-Chloro-2-((1-((1,3,5-trimethyl-1H-pyrazol-4-yl)sulfonyl)piperidin-4-yl)oxy)pyridine

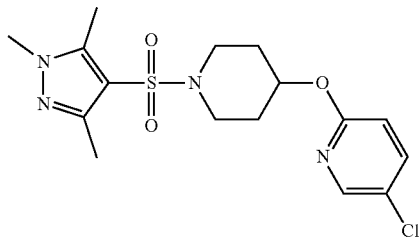 [SMILES: Cc1nn(C)c(C)c1S(=O)(=O)N1CCC(Oc2ccc(Cl)cn2)CC1]

Prepared as described for 4-(3,4-dichlorophenoxy)-1-[(1,3,5-trimethyl-1H-pyrazol-4-yl)sulfonyl]piperidine (Example 1) from 1,3,5-trimethyl-1H-pyrazole-4-sulfonyl chloride and 5-chloro-2-(piperidin-4-yloxy)pyridine hydrochloride (Intermediate 18).

$^1$H NMR (400 MHz, DMSO-$d_6$) δ ppm 1.64-1.80 (m, 2H) 1.99-2.12 (m, 2H) 2.26 (s, 3H) 2.41 (s, 3H) 2.75-2.92 (m, 2H) 3.19-3.29 (m, 2H) 3.72 (s, 3H) 4.92-5.05 (m, 1H) 6.80-6.87 (m, 1H) 7.73-7.86 (m, 1H) 8.14-8.20 (m, 1H)

MS ES$^+$: 385

Example 49 (4-Chlorophenyl)(1-((1,3,5-trimethyl-1H-pyrazol-4-yl)sulfonyl)piperidin-4-yl)methanone

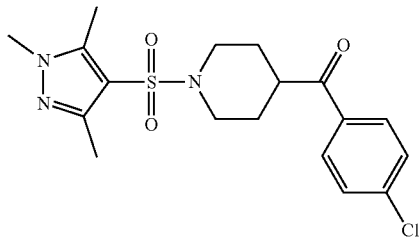 [SMILES: Cc1nn(C)c(C)c1S(=O)(=O)N1CCC(C(=O)c2ccc(Cl)cc2)CC1]

Prepared as described for 4-(3,4-dichlorophenoxy)-1-[(1,3,5-trimethyl-1H-pyrazol-4-yl)sulfonyl]piperidine (Example 1) from 1,3,5-trimethyl-1H-pyrazole-4-sulfonyl chloride and (4-chlorophenyl)(piperidin-4-yl)methanone.

$^1$H NMR (400 MHz, DMSO-$d_6$) δ ppm 1.50-1.65 (m, 2H) 1.76-1.80 (m, 2H) 2.28 (s, 3H) 2.43 (s, 3H) 2.48-2.54 (m, 2H) 3.45-3.52 (m, 1H) 3.58-3.62 (m, 2H) 3.78 (s, 3H) 7.60 (d, J=7.8 Hz 2H) 7.98 (d, J=7.8 Hz 2H)

MS ES$^+$: 396

Example 50 (3,4-Dichlorophenyl)(1-((1,3,5-trimethyl-1H-pyrazol-4-yl)sulfonyl)piperidin-4-yl)methanone

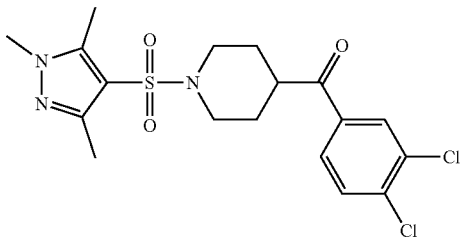 [SMILES: Cc1nn(C)c(C)c1S(=O)(=O)N1CCC(C(=O)c2ccc(Cl)c(Cl)c2)CC1]

Prepared as described for 4-(3,4-dichlorophenoxy)-1-[(1,3,5-trimethyl-1H-pyrazol-4-yl)sulfonyl]piperidine (Example 1) from 1,3,5-trimethyl-1H-pyrazole-4-sulfonyl chloride and (3,4-dichlorophenyl)(piperidin-4-yl)methanone.

$^1$H NMR (400 MHz, DMSO-d$_6$) δ ppm 1.5-1.62 (m, 2H) 1.85-1.92 (m, 2H) 2.28 (s, 3H) 2.45 (s, 3H) 2.45-2.58 (m, 2H) 3.48-3.55 (m, 1H) 3.60-3.65 (m, 2H) 3.74 (s, 3H) 7.8 (d, J=7.5 Hz 1H) 7.95 (d, J=7.5 Hz 1H) 8.20 (d, 1H)

MS ES$^+$: 430

Example 51 N-(4-Chlorophenyl)-1-((1,3,5-trimethyl-1H-pyrazol-4-yl)sulfonyl)piperidin-4-amine

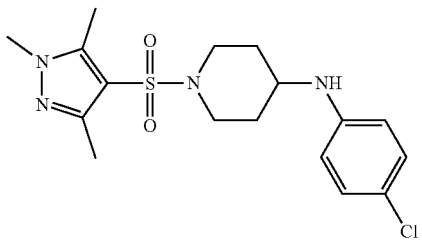 [SMILES: Cc1nn(C)c(C)c1S(=O)(=O)N1CCC(Nc2ccc(Cl)cc2)CC1]

Prepared as described for 4-(3,4-dichlorophenoxy)-1-[(1,3,5-trimethyl-1H-pyrazol-4-yl)sulfonyl]piperidine (Example 1) from 1,3,5-trimethyl-1H-pyrazole-4-sulfonyl chloride and N-(4-chlorophenyl)piperidin-4-amine.

$^1$H NMR (400 MHz, DMSO-d$_6$) δ ppm 1.46-1.58 (m, 2H) 1.92-2.00 (m, 2H) 2.30 (s, 3H) 2.40 (s, 3H) 2.45-2.55 (m, 2H) 3.28-3.35 (m, 1H) 3.52-3.60 (m, 2H) 3.72 (s, 3H) 6.30 (br, 1H) 7.90 (br, 2H) 7.25 (br, 2H)

MS ES$^+$: 383

Example 52 N-(3,4-Dichlorophenyl)-1-((1,3,5-trimethyl-1H-pyrazol-4-yl)sulfonyl)piperidin-4-amine

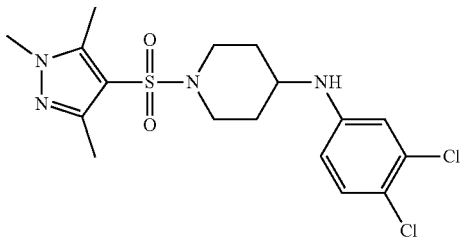 [SMILES: Cc1nn(C)c(C)c1S(=O)(=O)N1CCC(Nc2ccc(Cl)c(Cl)c2)CC1]

Prepared as described for 4-(3,4-dichlorophenoxy)-1-[(1,3,5-trimethyl-1H-pyrazol-4-yl)sulfonyl]piperidine (Example 1) from 1,3,5-trimethyl-1H-pyrazole-4-sulfonyl chloride and N-(3,4-dichlorophenyl)piperidin-4-amine.

$^1$H NMR (400 MHz, DMSO-d$_6$) δ ppm 1.46-1.58 (m, 2H) 1.92-2.00 (m, 2H) 2.30 (s, 3H) 2.40 (s, 3H) 2.45-2.55 (m, 2H) 3.28-3.35 (m, 1H) 3.52-3.60 (m, 2H) 3.72 (s, 3H) 6.30 (br, 1H) 7.90 (br, 1H) 7.25 (br, 1H)

MS ES$^+$: 417

Example 53 4-Chloro-N-{[1-(trimethyl-1H-pyrazole-4-sulfonyl)piperidin-4-yl]methyl}aniline

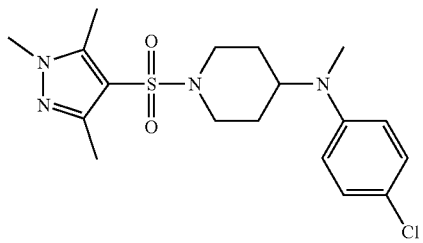 [SMILES: Cc1nn(C)c(C)c1S(=O)(=O)N1CCC(N(C)c2ccc(Cl)cc2)CC1]

A mixture of 4-chloroaniline (276 mg, 2.17 mmol), 1-(1,3,5-trimethyl-1H-pyrazole-4-sulfonyl)piperidin-4-one (Intermediate 8, 590 mg, 2.17 mmol), acetic acid (303 mg, 5.05 mmol) and sodium triacetoxyborohydride (670 mg, 3.16 mmol) in 1,2-dichloroethane (21 mL) was stirred at room temperature overnight. Formaldehyde (37% in water, 350 mg, 4.33 mmol) and sodium triacetoxyborohydride (918 mg, 4.33 mmol) were added to the reaction mixture and this was then stirred overnight at room temperature. Dichloromethane (50 mL) was added. The reaction mixture was washed with water (3×25 mL) and the organic layer separated, dried over sodium sulfate, filtered and concentrated under reduced pressure. The crude product was purified by silica chromatography to afford the desired product, 4-chloro-N-{[1-(trimethyl-1H-pyrazole-4-sulfonyl)piperidin-4-yl]methyl}aniline (132 mg, 15%).

$^1$H NMR (400 MHz, CDCl$_3$) δ ppm 1.76-1.94 (m, 4H) 2.39 (s, 3H) 2.42-2.49 (m, 2H) 2.47 (s, 3H) 2.74 (s, 3H) 3.45-3.53 (m, 2H) 3.77 (s, 3H) 3.86-3.89 (m, 1H) 6.66 (d, J=9.13 2 H) 7.15 (d, J=9.13 2 H)

MS ES$^+$: 397

Example 54 3,4-Dichloro-N-{[1-(trimethyl-1H-pyrazole-4-sulfonyl)piperidin-4-yl]methyl}aniline

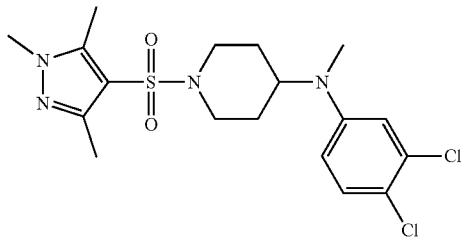 [SMILES: Cc1nn(C)c(C)c1S(=O)(=O)N1CCC(N(C)c2ccc(Cl)c(Cl)c2)CC1]

Prepared as described for 4-chloro-N-{[1-(trimethyl-1H-pyrazole-4-sulfonyl)piperidin-4-yl]methyl}aniline (Example 53) from 1-(1,3,5-trimethyl-1H-pyrazole-4-sulfonyl)piperidin-4-one (Intermediate 8) and 3,4-dichloroaniline.

¹H NMR (400 MHz, CDCl₃) δ ppm 1.76-1.93 (m, 4H) 2.39 (s, 3H) 2.44-2.50 (m, 2H) 2.48 (s, 3H) 2.74 (s, 3H) 3.45-3.51 (m, 2H) 3.77 (s, 3H) 3.86-3.91 (m, 1H) 6.56 (dd, J=3.00, 9.06 1 H) 6.77 (d, J=3.00, 1H) 7.21 (d, J=8.99, 1H)

MS ES⁺: 431

Example 55 4-(4-Chlorobenzyl)-1-((1,3,5-trimethyl-1H-pyrazol-4-yl)sulfonyl)piperidine

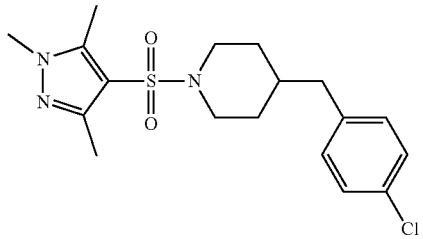 [SMILES: Cc1nn(C)c(C)c1S(=O)(=O)N1CCC(Cc2ccc(Cl)cc2)CC1]

Prepared as described for 4-(3,4-dichlorophenoxy)-1-[(1,3,5-trimethyl-1H-pyrazol-4-yl)sulfonyl]piperidine (Example 1) from 1,3,5-trimethyl-1H-pyrazole-4-sulfonyl chloride and 4-(4-chlorobenzyl)piperidine hydrochloride.

¹H NMR (400 MHz, DMSO-d₆) δ ppm 1.11-1.24 (m, 2H) 1.43-1.55 (m, 1H) 1.56-1.66 (m, 2H) 2.20-2.26 (m, 5H) 2.37 (s, 3H) 2.48 (m, 2H) 3.49-3.59 (m, 2H) 3.70 (s, 3H) 7.14-7.20 (m, 2H) 7.28-7.35 (m, 2H)

MS ES⁺: 382

Example 56 4-(3,4-Dichlorobenzyl)-1-((1,3,5-trimethyl-1H-pyrazol-4-yl)sulfonyl)piperidine

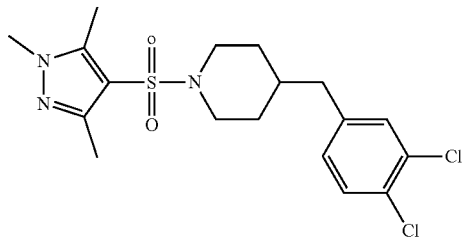

Prepared as described for 4-(3,4-dichlorophenoxy)-1-[(1,3,5-trimethyl-1H-pyrazol-4-yl)sulfonyl]piperidine (Example 1) from 1,3,5-trimethyl-1H-pyrazole-4-sulfonyl chloride and 4-(3,4-dichlorobenzyl)piperidine hydrochloride.

¹H NMR (400 MHz, DMSO-d₆) δ ppm 1.11-1.26 (m, 2H) 1.47-1.56 (m, 1H) 1.57-1.65 (m, 2H) 2.15-2.26 (m, 5H) 2.37 (s, 3H) 3.49-3.59 (m, 4H) 3.70 (s, 3H) 7.13-7.18 (m, 1H) 7.43-7.47 (m, 1H) 7.49-7.54 (m, 1H)

MS ES⁺: 416

Example 57 4-(4-Chlorobenzyl)-1-((1,3,5-trimethyl-1H-pyrazol-4-yl)sulfonyl)piperidin-4-ol

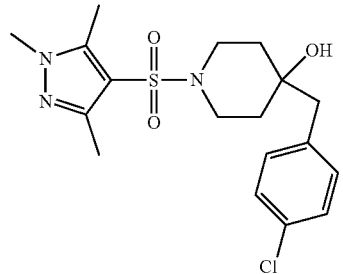 [SMILES: Cc1nn(C)c(C)c1S(=O)(=O)N1CCC(O)(Cc2ccc(Cl)cc2)CC1]

To a flask charged with magnesium turnings (0.087 g, 3.6 mmol, 3.0 eq) was added anhydrous diethyl ether (15 mL) followed by addition of catalytic amount of iodine (0.005 g). The reaction was heated at reflux and then 4-chloro benzyl chloride (0.588 g, 3.6 mmol, 3.0 eq) was added dropwise. The resulting mixture was refluxed for 1 hour to produce Grignard reagent.

1-(1,3,5-Trimethyl-1H-pyrazole-4-sulfonyl)piperidin-4-one (0.33 g, 1.2 mmol, 1.0 eq, Intermediate 8) was dissolved in THF (10 mL) and cooled to 0° C. The Grignard reagent was added to above solution at 0° C. and the resulting mixture was stirred at room temperature for 2 hours. The reaction was diluted with saturated aqueous solution of ammonium chloride and extracted with ethyl acetate. The organic layer was washed with brine, dried over sodium sulfate and concentrated. The crude product was purified by column chromatography using 60-120 mesh size neutral silica. The compound was eluted in 0-2% methanol in dichloromethane to yield 4-(4-chlorobenzyl)-1-(1,3,5-trimethyl-1H-pyrazol-4-ylsulfonyl)piperidin-4-ol. (0.18 g, 37.26% yield).

¹H NMR (400 MHz, Chloroform-d) δ ppm 1.51-1.69 (m, 2H) 1.80 (td, J=13.20, 4.43 Hz, 2H) 2.38 (s, 3H) 2.46 (s, 3H) 2.60-2.86 (m, 4H) 3.57 (d, J=11.60 Hz, 2H) 3.76 (s, 3H) 7.13 (d, J=7.32 Hz, 2H) 7.23-7.46 (m, 2H)

MS ES⁺: 398

Example 58 4-(4-Chlorobenzyl)-4-methoxy-1-((1,3,5-trimethyl-1H-pyrazol-4-yl)sulfonyl)piperidine

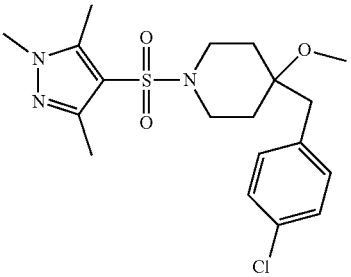

Sodium hydride (60% in paraffin; 0.033 g, 0.85 mmol, 2.0 eq) was suspended in THF (5 mL) and 4-(4-chlorobenzyl)-1-((1,3,5-trimethyl-1H-pyrazol-4-yl)sulfonyl)piperidin-4-ol (Example 57, 0.17 g, 0.42 mmol, 1.0 eq) was added in THF (10 mL) slowly at room temperature. The reaction mixture was heated to 50° C. for 2 hours and then cooled to room temperature. Hexamethylphosphoramide (0.383 g, 2.14 mmol, 5.0 eq) and methyl iodide (0.6 g, 4.28 mmol, 10.0 eq) were added and the reaction was stirred at 50° C. overnight. The reaction was poured into saturated aqueous sodium bisulfate solution and extracted with ethyl acetate. The organic layer was washed with brine, dried over sodium sulfate and concentrated. The crude product was purified by column chromatography using 60-120 mesh size neutral silica. The compound was eluted in 0-2% methanol in dichloromethane to yield 4-(4-chlorobenzyl)-4-methoxy-1-(1,3,5-trimethyl-1H-pyrazol-4-ylsulfonyl)piperidine (0.15 g, 85.71% yield).

$^1$H NMR (400 MHz, chloroform-d) δ ppm 1.62-1.69 (m, 2H) 1.70-1.85 (m, 2H) 2.39 (s, 3H) 2.44 (s, 3H) 2.55-2.69 (m, 2H) 2.74 (s, 2H) 3.27 (s, 3H) 3.43-3.60 (m, 2H) 3.77 (s, 3H) 7.02-7.14 (m, 2H) 7.23-7.28 (m, 2H)

MS ES$^+$: 412

Example 59 4-(2,4-Dichlorobenzyl)-1-((1,3,5-trimethyl-1H-pyrazol-4-yl)sulfonyl)piperidin-4-ol

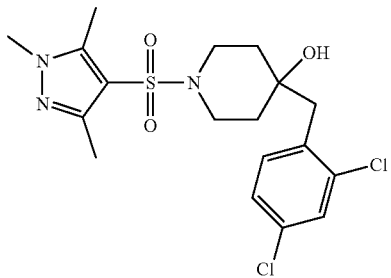 [SMILES: Cc1nn(C)c(C)c1S(=O)(=O)N1CCC(O)(Cc2ccc(Cl)cc2Cl)CC1]

Prepared as described for 4-(4-chlorobenzyl)-1-((1,3,5-trimethyl-1H-pyrazol-4-yl)sulfonyl)piperidin-4-ol (Example 57) from 1-(1,3,5-trimethyl-1H-pyrazole-4-sulfonyl)piperidin-4-one (Intermediate 8) and 2,4-dichloro-1-(chloromethyl)benzene.

$^1$H NMR (400 MHz, acetonitrile-d$_3$) S ppm 1.49-1.57 (m, 2H) 1.74 (s, 2H) 2.30 (s, 3H) 2.41 (s, 3H) 2.50-2.56 (m, 1H) 2.56-2.71 (m, 2H) 2.91 (s, 2H) 3.36-3.53 (m, 2H) 3.71 (s, 3H) 7.22-7.40 (m, 2H) 7.49 (s, 1H)

MS ES$^+$: 432

Example 60 4-(4-Chlorobenzyl)-4-(methoxymethyl)-1-((1,3,5-trimethyl-1H-pyrazol-4-yl)sulfonyl)piperidine

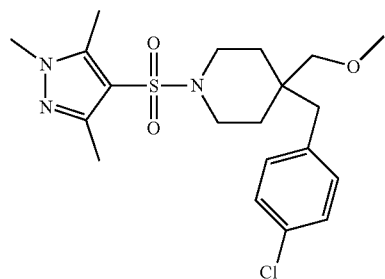

Prepared as described for 4-(4-chlorobenzyl)-4-methoxy-1-((1,3,5-trimethyl-1H-pyrazol-4-yl)sulfonyl)piperidine (Example 58) from (4-(4-chlorobenzyl)-1-(1,3,5-trimethyl-1H-pyrazol-4-yl)sulfonyl)piperidin-4-yl)methanol.

$^1$H NMR (400 MHz, acetonitrile-d$_3$) S ppm 1.44-1.62 (m, 4H) 2.31 (s, 3H) 2.42 (s, 3H) 2.55-2.71 (m, 2H) 2.84-3.02 (m, 4H) 3.07-3.20 (m, 2H) 3.27 (s, 3H) 3.72 (s, 3H) 7.12 (s, 2H) 7.23-7.36 (m, 2H)

MS ES$^+$: 426

Example 61 Ethyl 4-(4-chlorobenzyl)-1-((1,3,5-trimethyl-1H-pyrazol-4-yl)sulfonyl)piperidine-4-carboxylate

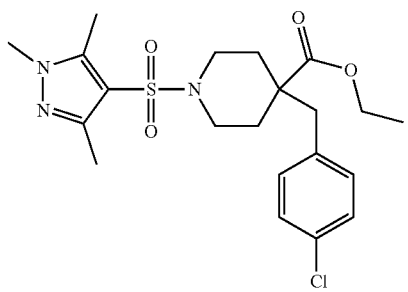 [SMILES: CCOC(=O)C1(Cc2ccc(Cl)cc2)CCN(S(=O)(=O)c2c(C)nn(C)c2C)CC1]

Prepared as described for 4-(3,4-dichlorophenoxy)-1-[(1,3,5-trimethyl-1H-pyrazol-4-yl)sulfonyl]piperidine (Example 1) from 1,3,5-trimethyl-1H-pyrazole-4-sulfonyl chloride and ethyl 4-(4-chlorobenzyl)piperidine-4-carboxylate hydrochloride (Intermediate 21).

$^1$H NMR (400 MHz, DMSO-d$_6$) δ ppm 1.00 (t J=7 Hz 3H) 1.53-1.62 (m, 2H) 1.97-2.06 (m, 2H) 2.21 (s, 3H) 2.25-2.35 (m 2H) 2.38 (s 3H) 2.78 (s 2H) 3.33 (s 3H) 3.45-3.50 (m, 2H) 3.95-4.0.6 (ABq, J=8 Hz 2H) 7.08 (d, J=7.8 Hz 2H) 7.34 (d, J=7.8 Hz 2H)

MS ES$^+$: 454

Example 62 Ethyl 4-(4-bromobenzyl)-1-((3,5-dimethyl-1H-pyrazol-4-yl)sulfonyl)piperidine-4-carboxylate

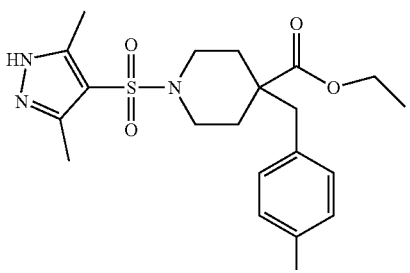

Prepared as described for 4-(3,4-dichlorophenoxy)-1-[(1,3,5-trimethyl-1H-pyrazol-4-yl)sulfonyl]piperidine (Example 1) from 3,5-dimethyl-1H-pyrazole-4-sulfonyl chloride (Intermediate 3) and ethyl 4-(4-bromobenzyl)piperidine-4-carboxylate hydrochloride (prepared as described for ethyl 4-(4-chlorobenzyl)piperidine-4-carboxylate hydrochloride (Intermediate 21) using 1-tert-butyl 4-ethyl 4-(4-bromobenzyl)piperidine-1,4-dicarboxylate).

$^1$H NMR (400 MHz, DMSO-d$_6$) δ ppm 0.91-1.09 (m, 3H) 1.46-1.68 (m, 2H) 1.96-2.04 (m, 2H) 2.12-2.42 (m, 8H) 2.77

(s, 2H) 3.38-3.57 (m, 2H) 3.86-4.14 (m, 2H) 6.83-7.16 (m, 2H) 7.34-7.59 (m, 2H) 13.02 (br. s., 1H)

MS ES⁺: 485

Example 63 Ethyl 4-(4-bromobenzyl)-1-((1,3,5-trimethyl-1H-pyrazol-4-yl)sulfonyl)piperidine-4-carboxylate

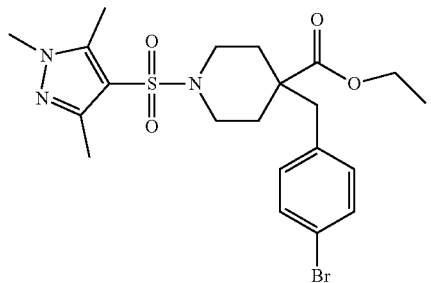 [SMILES: CCOC(=O)C1(Cc2ccc(Br)cc2)CCN(S(=O)(=O)c2c(C)nn(C)c2C)CC1]

Prepared as described for ethyl 4-(4-bromobenzyl)-1-((3,5-dimethyl-1H-pyrazol-4-yl)sulfonyl)piperidine-4-carboxylate (Example 62) from 1,3,5-trimethyl-1H-pyrazole-4-sulfonyl chloride.

¹H NMR (400 MHz, DMSO-$d_6$) δ ppm 1.05 (t, 3H) 1.55-1.63 (m, 2H) 1.99-2.05 (m, 2H) 2.22 (s, 3H) 2.28-2.34 (m, 2H) 2.38 (s, 3H) 2.76 (s, 2H) 3.46-3.52 (m, 2H) 3.72 (s, 3H) 4.00 (ABq, 2H) 6.95 (d, J=7.8 Hz 2H) 7.54 (d, J=7.8 Hz 2H)

MS ES⁺: 499

Example 64 4-(4-Chlorobenzyl)-1-((3,5-dimethyl-1H-pyrazol-4-yl)sulfonyl)piperidine-4-carbonitrile

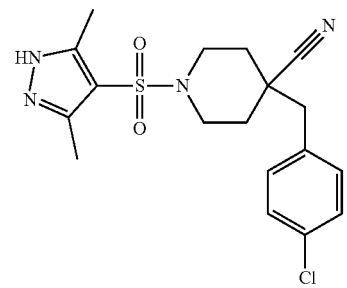 [SMILES: Cc1n[nH]c(C)c1S(=O)(=O)N1CCC(C#N)(Cc2ccc(Cl)cc2)CC1]

A solution of 1-((3,5-dimethyl-1H-pyrazol-4-yl)sulfonyl) piperidine-4-carbonitrile (Intermediate 9) (100 mg, 0.373 mmol) at 0° C. in THF (5 ml) was treated with lithium bis(trimethylsilyl)amide (1M in THF) (0.783 ml, 0.783 mmol). The reaction mixture was stirred at 0° C. for 1 hour. 1-chloro-4-(chloromethyl)benzene (60 mg, 0.373 mmol) was added. The reaction was stirred at room temperature for 16 hours. The reaction was treated with 10% aqueous citric acid and DCM. The layers were separated. The aqueous phase was extracted with dichloromethane and the organic layers combined, dried over magnesium sulphate, filtered and concentrated in vacuo. The crude product was purified by preparative LCMS (basic conditions) to give the title compound, 4-(4-chlorobenzyl)-1-((3,5-dimethyl-1H-pyrazol-4-yl)sulfonyl)piperidine-4-carbonitrile (56 mg, 34%).

¹H NMR (400 MHz, DMSO-$d_6$) δ ppm 1.73 (td, J=12.95, 3.79 Hz, 2H) 1.80-1.95 (m, 2H) 2.26 (s, 3H) 2.29-2.42 (m, 5H) 2.93 (s, 2H) 3.65 (d, J=12.13 Hz, 2H) 7.31 (d, J=8.34 Hz, 2H) 7.42 (d, J=8.46 Hz, 2H) 13.09 (s, 1H)

MS ES⁺: 393

Example 65 4-(2,4-Dichlorobenzyl)-1-((3,5-dimethyl-1H-pyrazol-4-yl)sulfonyl)piperidine-4-carbonitrile

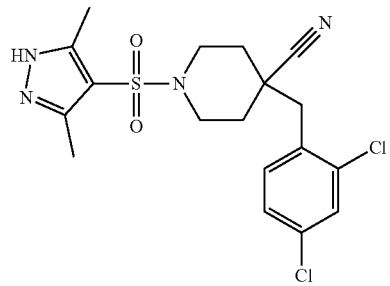 [SMILES: Cc1n[nH]c(C)c1S(=O)(=O)N1CCC(C#N)(Cc2ccc(Cl)cc2Cl)CC1]

Prepared as described for 4-(4-chlorobenzyl)-1-((3,5-dimethyl-1H-pyrazol-4-yl)sulfonyl)piperidine-4-carbonitrile (Example 64) from 1-((3,5-dimethyl-1H-pyrazol-4-yl)sulfonyl)piperidine-4-carbonitrile (Intermediate 9) and 2,4-dichloro-1-(chloromethyl)benzene.

¹H NMR (400 MHz, DMSO-$d_6$) δ ppm 1.72-1.87 (m, 2H) 1.89-2.04 (m, 2H) 2.26 (s, 3H) 2.30-2.46 (m, 5H) 3.11 (s, 2H) 3.67 (d, J=12.38 Hz, 2H) 7.41-7.54 (m, 2H) 7.66 (d, J=1.77 Hz, 1H) 13.10 (s, 1H)

MS ES⁺: 428

Example 66 4-(4-Chlorobenzyl)-1-((3,5-diethyl-1H-pyrazol-4-yl)sulfonyl)piperidine

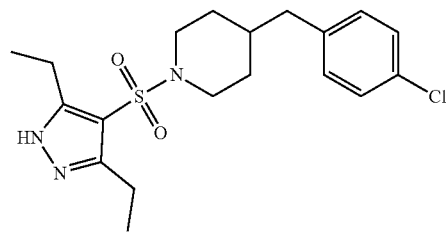 [SMILES: CCc1n[nH]c(CC)c1S(=O)(=O)N1CCC(Cc2ccc(Cl)cc2)CC1]

A solution of 3,5-heptanedione (12.5 g, 97.5 mmol) in ethanol (50 mL) was treated dropwise with hydrazine hydrate (60%, 5.72 g, 107 mmol) whilst cooling in an ice bath. The reaction was stirred for 1.5 hours at room temperature. The reaction was concentrated under reduced pressure. The reaction mixture was partitioned between DCM and brine, the aqueous layer was extracted with DCM. The combined organic layers were dried (Na₂SO₄), filtered and concentrated under reduced pressure to afford 3,5-diethyl-1H-pyrazole that was used crude. 3,5-diethyl-1H-pyrazole (6.0 g, 0.048 mol) was added dropwise to chlorosulfonic acid (30.9 g, 17.7 mL, 0.265 mol) at 0° C. with stirring. The reaction was heated to 80° C. for 30 minutes. The reaction was cooled and thionyl chloride (6.32 g, 3.8 mL, 53.1 mol) was added dropwise. The reaction was heated to 65° C. for 4 hours. The reaction mixture was cooled to room temperature and carefully poured onto ice (100 g) with stirring. The resultant solid was filtered and dried under vacuum to afford 3,5-diethyl-1H-pyrazole-4-sulfonyl chloride as a brown solid (9.15 g, 85% yield). The title compound was prepared as described for 4-(3,4-dichlorophenoxy)-1-[(1,3,5-trimethyl-1H-pyrazol-4-yl)sulfonyl]piperidine (Example 1) from 3,5-diethyl-1H-pyrazole-4-sulfonyl chloride and 4-(4-chlorobenzyl)piperidine hydrochloride.

$^1$H NMR (400 MHz, DMSO-d$_6$) δ ppm 1.07-1.25 (m, 8H) 1.45-1.75 (m, 3H) 2.20-2.28 (m, 2H) 2.45-2.55 (m, 2H) 2.68-2.80 (m, 4H) 3.52-3.61 (m, 2H) 4.10 (br s, 1H) 7.15-7.25 (m, 2H) 7.28-7.32 (m, 2H)

MS: ES+ 396

Example 67 4-(4-Chlorobenzyl)-1-((3,5-dimethyl-1H-pyrazol-4-yl)sulfonyl)piperidine

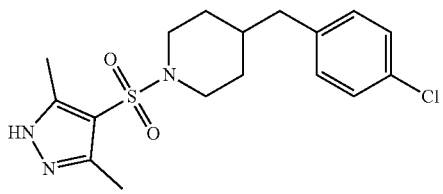 [SMILES: Cc1n[nH]c(C)c1S(=O)(=O)N1CCC(Cc2ccc(Cl)cc2)CC1]

Prepared as described for 4-(3,4-dichlorophenoxy)-1-[(1,3,5-trimethyl-1H-pyrazol-4-yl)sulfonyl]piperidine (Example 1) from 3,5-dimethyl-1H-pyrazole-4-sulfonyl chloride (Intermediate 3) and 4-(4-chlorobenzyl)piperidine hydrochloride.

$^1$H NMR (400 MHz, DMSO d$_6$) δ ppm 1.34-1.59 (m, 4H) 1.88 (m, 1H) 2.54-2.61 (m, 2H) 2.77 (s, 6H) 2.91-3.01 (4H, m) 720-7.25 (m, 2H) 7.44-7.48 (m, 2H) 11.28 (br s, 1H)

MS: ES+ 368

Example 68 1-((5-Chloro-1,3-dimethyl-1H-pyrazol-4-yl)sulfonyl)-4-(4 chlorobenzyl)piperidine

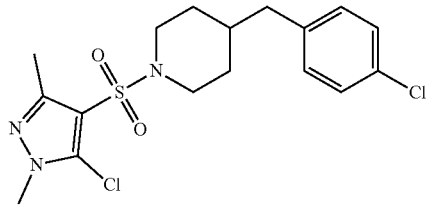 [SMILES: Cc1nn(C)c(Cl)c1S(=O)(=O)N1CCC(Cc2ccc(Cl)cc2)CC1]

Prepared as described for 4-(3,4-dichlorophenoxy)-1-[(1,3,5-trimethyl-1H-pyrazol-4-yl)sulfonyl]piperidine (Example 1) from 5-chloro-1,3-dimethyl-1H-pyrazole-4-sulfonyl chloride and 4-(4-chlorobenzyl)piperidine hydrochloride.

$^1$H NMR (400 MHz, DMSO-d$_6$) δ ppm 1.32-1.46 (m, 2H) 1.48-1.59 (m, 2H) 1.88 (m, 1H) 2.52-2.60 (m, 2H) 2.78 (s, 3H) 2.91-3.11 (4H, m) 3.95 (s, 3H) 7.21-7.27 (m, 2H) 7.42-7.46 (m, 2H)

MS: ES+ 402

Example 69 4-(3,4-Dichlorobenzyl)-1-((1,3,5-trimethyl-1H-pyrazol-4-yl)sulfonyl)piperidine-4-ol

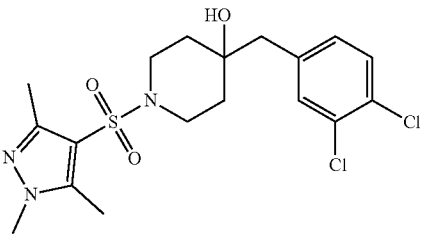 [SMILES: Cc1nn(C)c(C)c1S(=O)(=O)N1CCC(O)(Cc2ccc(Cl)c(Cl)c2)CC1]

Prepared as described for 4-(3,4-dichlorophenoxy)-1-[(1,3,5-trimethyl-1H-pyrazol-4-yl)sulfonyl]piperidine (Example 1) from 1,3,5-trimethyl-1H-pyrazole-4-sulfonyl chloride and 4-(3,4-dichlorobenzyl)piperidin-4-ol 2,2,2-trifluoroacetate (Intermediate 23).

$^1$H NMR (400 MHz, DMSO-d$_6$) δ ppm 1.35-1.45 (m, 2H) 1.55-1.53 (m, 2H) 2.20 (s, 3H) 2.45 (s, 3H) 3.30-3.40 (4H, m) 3.70 (s, 3H) 7.20-7.22 (m, 1H) 7.45 (1H, s) 7.55-7.60 (m, 2H)

MS: ES+ 432

Example 70 4-(3,4-Dichlorobenzyl)-1-((3,5-dimethyl-1H-pyrazol-4-yl)sulfonyl)piperidin-4-ol

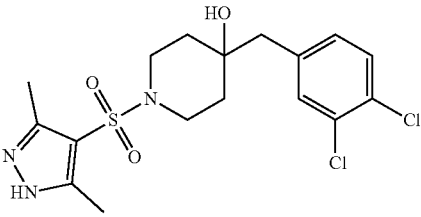 [SMILES: Cc1n[nH]c(C)c1S(=O)(=O)N1CCC(O)(Cc2ccc(Cl)c(Cl)c2)CC1]

Prepared as described for 4-(3,4-dichlorophenoxy)-1-[(1,3,5-trimethyl-1H-pyrazol-4-yl)sulfonyl]piperidine (Example 1) from 3,5-dimethyl-1H-pyrazole-4-sulfonyl chloride (Intermediate 3) and 4-(3,4-dichlorobenzyl)piperidin-4-ol 2,2,2-trifluoroacetate (Intermediate 23).

$^1$H NMR (400 MHz, DMSO-d$_6$) δ ppm 1.34-1.44 (m, 2H) 1.53-1.56 (m, 2H) 2.27 (s, 3H) 2.45 (s, 3H) 3.30-3.40 (4H, m) 7.20-7.22 (m, 1H) 7.45 (1H, s) 7.55-7.60 (m, 2H) 11.05 (br s, 1H)

MS: ES+ 418

Example 71 4-(4-Chloro-3-fluorobenzyl)-1-((3,5-dimethyl-1H-pyrazol-4-yl)sulfonyl)piperidine

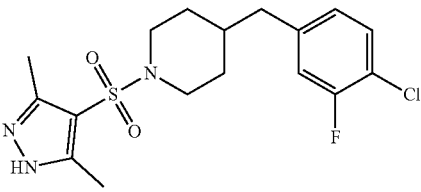 [SMILES: Cc1n[nH]c(C)c1S(=O)(=O)N1CCC(Cc2ccc(Cl)c(F)c2)CC1]

Prepared as described for 4-(3,4-dichlorophenoxy)-1-[(1,3,5-trimethyl-1H-pyrazol-4-yl)sulfonyl]piperidine (Example 1) from 3,5-dimethyl-1H-pyrazole-4-sulfonyl chloride (Intermediate 3) and 4-(4-Chloro-3-fluorobenzyl) piperidine hydrochloride (Intermediate 25).

$^1$H NMR (400 MHz, DMSO-d$_6$) δ ppm 1.07-1.28 (m, 2H) 1.44-1.71 (m, 3H) 2.10-2.41 (m, 7H) 3.27-3.37 (m, 3H) 3.45-3.60 (m, 2H) 6.98-7.08 (m, 1H) 7.17-7.25 (m, 1H) 7.40-7.53 (m, 1H) 13.00 (br. s., 1H)

MS: ES+ 386

Example 72 4-(4-Chloro-3-fluorobenzyl)-1-((1,3,5-trimethyl-1H-pyrazol-4-yl)sulfonyl)piperidine

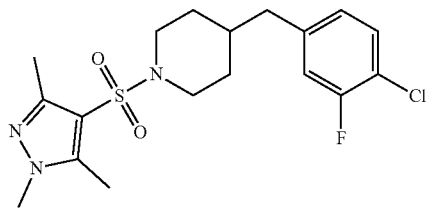 [SMILES: Cc1nn(C)c(C)c1S(=O)(=O)N1CCC(Cc2ccc(Cl)c(F)c2)CC1]

Prepared as described for 4-(3,4-dichlorophenoxy)-1-[(1,3,5-trimethyl-1H-pyrazol-4-yl)sulfonyl]piperidine (Example 1) from 1,3,5-trimethyl-1H-pyrazole-4-sulfonyl chloride and 4-(4-Chloro-3-fluorobenzyl)piperidine hydrochloride (Intermediate 25).

$^1$H NMR (400 MHz, DMSO-d$_6$) δ ppm 1.12-1.25 (m, 2H) 1.47-1.66 (m, 3H) 2.16-2.26 (m, 5H) 2.37 (s, 3H) 3.28-3.31 (m, 2H) 3.49-3.58 (m, 2H) 3.68-3.72 (m, 3H) 6.99-7.06 (m, 1H) 7.20-7.26 (m, 1H) 7.43-7.50 (m, 1H)

MS: ES+ 400

Example 73 4-(4-Chloro-2-methoxyphenoxy)-1-((3,5-dimethyl-1H-pyrazol-4-yl)sulfonyl)piperidine

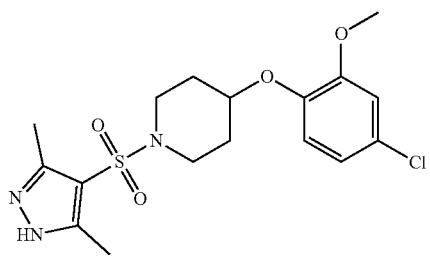 [SMILES: COc1cc(Cl)ccc1OC1CCN(S(=O)(=O)c2c(C)n[nH]c2C)CC1]

Prepared as described for 4-(3,4-dichlorophenoxy)-1-[(1,3,5-trimethyl-1H-pyrazol-4-yl)sulfonyl]piperidine (Example 1) from 3,5-dimethyl-1H-pyrazole-4-sulfonyl chloride (Intermediate 3) and 4-(4-chloro-2-methoxyphenoxy) piperidine hydrochloride (Intermediate 26).

$^1$H NMR (400 MHz, DMSO-d$_6$) δ ppm 1.62-1.74 (m, 2H) 1.87-1.99 (m, 2H) 2.22-2.41 (m, 6H) 2.83-2.94 (m, 2H) 3.15-3.25 (m, 2H) 3.71 (s, 3H) 4.30-4.39 (m, 1H) 6.85-6.90 (m, 1H) 6.98-7.04 (m, 2H) 13.08 (br. s., 1H)

MS: ES+ 400

Example 74 4-(4-Chloro-2-methoxyphenoxy)-1-((1,3,5-trimethyl-1H-pyrazol-4-yl)sulfonyl)piperidine

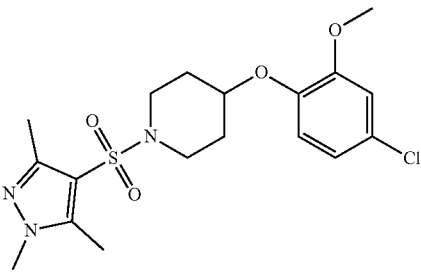 [SMILES: COc1cc(Cl)ccc1OC1CCN(S(=O)(=O)c2c(C)nn(C)c2C)CC1]

Prepared as described for 4-(3,4-dichlorophenoxy)-1-[(1,3,5-trimethyl-1H-pyrazol-4-yl)sulfonyl]piperidine (Example 1) from 1,3,5-trimethyl-1H-pyrazole-4-sulfonyl chloride and 4-(4-chloro-2-methoxyphenoxy)piperidine hydrochloride (Intermediate 26).

$^1$H NMR (400 MHz, DMSO-d$_6$) δ ppm 1.63-1.75 (m, 2H) 1.89-2.00 (m, 2H) 2.26 (s, 3H) 2.41 (s, 3H) 2.81-2.90 (m, 2H) 3.15-3.25 (m, 2H) 3.71 (s, 3H) 3.74 (s, 3H) 4.30-4.38 (m, 1H) 6.85-6.92 (m, 1H) 6.99-7.04 (m, 2H)

MS: ES+ 414

Example 75 4-(4-Chloro-2-fluorobenzyl)-1-((3,5-dimethyl-1H-pyrazol-4-yl)sulfonyl)piperidin-4-ol

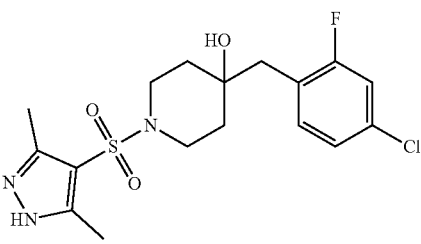 [SMILES: Cc1n[nH]c(C)c1S(=O)(=O)N1CCC(O)(Cc2ccc(Cl)cc2F)CC1]

Prepared as described for 4-(3,4-dichlorophenoxy)-1-[(1,3,5-trimethyl-1H-pyrazol-4-yl)sulfonyl]piperidine (Example 1) from 3,5-dimethyl-1H-pyrazole-4-sulfonyl chloride (Intermediate 3) and 4-(4-Chloro-2-fluorobenzyl) piperidin-4-ol 2,2,2-trifluoroacetate (Intermediate 28).

$^1$H NMR (400 MHz, DMSO-d$_6$) δ ppm 1.34-1.44 (m, 2H) 1.53-1.56 (m, 2H) 2.27 (s, 2H) 2.75 (s, 6H) 3.30-3.40 (4H, m) 7.20-7.22 (m, 1H) 7.45 (1H, s) 7.55-7.60 (m, 2H) 11.05 (br s, 1H)

MS: ES+ 402

Example 76 1-((3,5-Dimethyl-1H-pyrazol-4-yl) sulfonyl)-4-(2-fluorophenoxy)piperidine

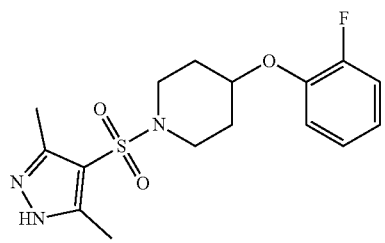 [SMILES: Cc1n[nH]c(C)c1S(=O)(=O)N1CCC(Oc2ccccc2F)CC1]

Prepared as described for 4-(3,4-dichlorophenoxy)-1-[(1,3,5-trimethyl-1H-pyrazol-4-yl)sulfonyl]piperidine (Example 1) from 3,5-dimethyl-1H-pyrazole-4-sulfonyl chloride (Intermediate 3) and 4-(2-fluorophenoxy)piperidine hydrochloride.

$^1$H NMR (400 MHz, DMSO-$d_6$) δ ppm 1.64-1.77 (m, 2H) 1.95-2.06 (m, 2H) 2.28 (br. s., 3H) 2.37 (br. s., 3H) 2.81-2.91 (m, 2H) 3.21-3.29 (m, 2H) 4.42-4.50 (m, 1H) 6.91-6.98 (m, 1H) 7.06-7.12 (m, 1H) 7.15-7.24 (m, 2H) 13.07 (br. s., 1H)

MS: ES+ 354

Example 77 5-Chloro-3-fluoro-2-((1-((1,3,5-trimethyl-1H-pyrazol-4-yl)sulfonyl)piperidin-4-yl)oxy)pyridine

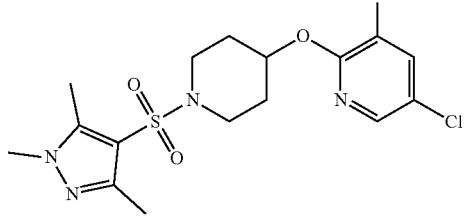

Prepared as described for 4-(3,4-dichlorophenoxy)-1-[(1,3,5-trimethyl-1H-pyrazol-4-yl)sulfonyl]piperidine (Example 1) from 1,3,5-trimethyl-1H-pyrazole-4-sulfonyl chloride and 5-chloro-3-fluoro-2-(piperidin-4-yloxy)pyridine hydrochloride (Intermediate 29).

$^1$H NMR (400 MHz, DMSO-$d_6$) δ ppm 1.73-1.84 (m, 2H) 2.02-2.12 (m, 2H) 2.26 (s, 3H) 2.41 (s, 3H) 2.82-2.91 (m, 2H) 3.21-3.29 (m, 2H) 3.73 (s, 3H) 5.04-5.12 (m, 1H) 8.00-8.06 (m, 2H)

MS: ES+ 403

Example 78 4-(4-Chloro-2-methoxybenzyl)-1-((3,5-dimethyl-1H-pyrazol-4-yl)sulfonyl)piperidine

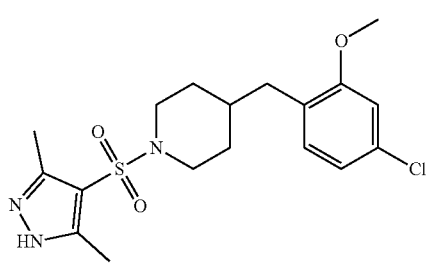 [SMILES: COc1cc(Cl)ccc1CC1CCN(S(=O)(=O)c2c(C)n[nH]c2C)CC1]

Prepared as described for 4-(3,4-dichlorophenoxy)-1-[(1,3,5-trimethyl-1H-pyrazol-4-yl)sulfonyl]piperidine (Example 1) from 3,5-dimethyl-1H-pyrazole-4-sulfonyl chloride (Intermediate 3) and 4-(4-chloro-2-methoxybenzyl)piperidine hydrochloride (Intermediate 30).

$^1$H NMR (400 MHz, DMSO-$d_6$) δ ppm 1.11-1.26 (m, 2H) 1.43-1.54 (m, 1H) 1.54-1.64 (m, 2H) 2.16-2.28 (m, 5H) 2.33 (br. s., 3H) 2.41-2.47 (m, 2H) 3.49-3.56 (m, 2H) 3.77 (s, 3H) 6.86-6.93 (m, 1H) 6.97-7.01 (m, 1H) 7.05-7.11 (m, 1H) 13.00 (s, 1H)

MS: ES+ 398

Example 79 4-(4-Chloro-2-methoxybenzyl)-1-((1,3,5-trimethyl-1H-pyrazol-4-yl)sulfonyl)piperidine

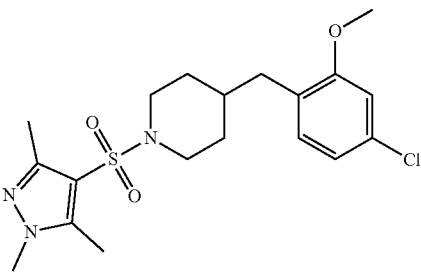 [SMILES: COc1cc(Cl)ccc1CC1CCN(S(=O)(=O)c2c(C)nn(C)c2C)CC1]

Prepared as described for 4-(3,4-dichlorophenoxy)-1-[(1,3,5-trimethyl-1H-pyrazol-4-yl)sulfonyl]piperidine (Example 1) from 1,3,5-trimethyl-1H-pyrazole-4-sulfonyl chloride and 4-(4-chloro-2-methoxybenzyl)piperidine hydrochloride (Intermediate 30).

$^1$H NMR (400 MHz, DMSO-$d_6$) δ ppm 1.11-1.25 (m, 2H) 1.42-1.53 (m, 1H) 1.54-1.63 (m, 2H) 2.14-2.25 (m, 5H) 2.37 (s, 3H) 2.42-2.47 (m, 2H) 3.47-3.56 (m, 2H) 3.69 (s, 3H) 3.77 (s, 3H) 6.86-6.94 (m, 1H) 6.98-7.02 (m, 1H) 7.06-7.11 (m, 1H)

MS: ES+ 412

Example 80 4-(4-Chloro-2-fluorobenzyl)-1-((3,5-dimethyl-1H-pyrazol-4-yl)sulfonyl)-4-fluoropiperidine

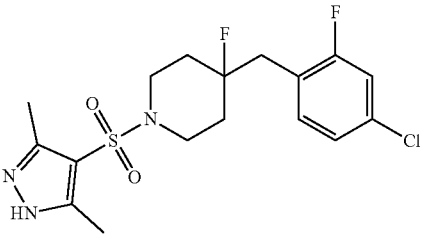 [SMILES: Cc1n[nH]c(C)c1S(=O)(=O)N1CCC(F)(Cc2ccc(Cl)cc2F)CC1]

Prepared as described for 4-(3,4-dichlorophenoxy)-1-[(1,3,5-trimethyl-1H-pyrazol-4-yl)sulfonyl]piperidine (Example 1) from 3,5-dimethyl-1H-pyrazole-4-sulfonyl chloride (Intermediate 3) and 4-(4-chloro-2-fluorobenzyl)-4-fluoropiperidine hydrochloride (Intermediate 31).

$^1$H NMR (400 MHz, DMSO-$d_6$) δ ppm 1.69-1.89 (m, 4H) 2.18-2.38 (m, 6H) 2.39-2.47 (m, 2H) 2.89-3.02 (m, 2H) 3.41-3.51 (m, 2H) 7.21-7.28 (m, 1H) 7.29-7.35 (m, 1H) 7.36-7.43 (m, 1H) 13.06 (br. s., 1H)

MS: ES+ 404

Example 81 4-(4-Chloro-2-fluorobenzyl)-4-fluoro-1-(((1,3,5-trimethyl-1H-pyrazol-4-yl)sulfonyl)piperidine

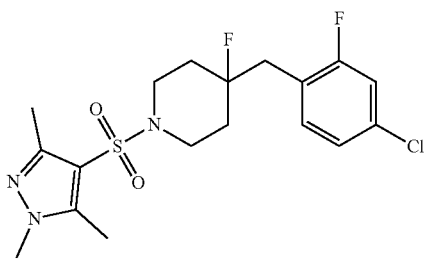 [SMILES: Cc1nn(C)c(C)c1S(=O)(=O)N1CCC(F)(Cc2ccc(Cl)cc2F)CC1]

Prepared as described for 4-(3,4-dichlorophenoxy)-1-[(1,3,5-trimethyl-1H-pyrazol-4-yl)sulfonyl]piperidine (Example 1) from 1,3,5-trimethyl-1H-pyrazole-4-sulfonyl chloride and 4-(4-chloro-2-fluorobenzyl)-4-fluoropiperidine hydrochloride (Intermediate 31).

$^1$H NMR (400 MHz, DMSO-d$_6$) δ ppm 1.70-1.88 (m, 4H) 2.23 (s, 3H) 2.38 (s, 3H) 2.39-2.47 (m, 2H) 2.91-3.01 (m, 2H) 3.41-3.50 (m, 2H) 3.70 (s, 3H) 7.22-7.28 (m, 1H) 7.28-7.35 (m, 1H) 7.37-7.43 (m, 1H)

MS: ES+ 418

Example 82 4-(4-Chloro-2-fluorobenzyl)-1-((3,5-dimethyl-1H-pyrazol-4-yl)sulfonyl)piperidine

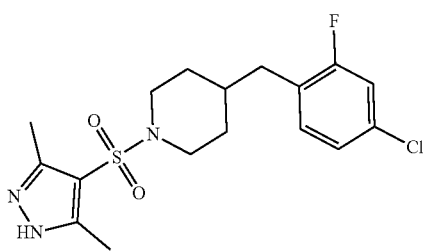 [SMILES: Cc1n[nH]c(C)c1S(=O)(=O)N1CCC(Cc2ccc(Cl)cc2F)CC1]

tert-Butyl 4-(4-chloro-2-fluorobenzylidene)piperidine-1-carboxylate was prepared as described for tert-butyl 4-(4-chloro-3-fluorobenzylidene)piperidine-1-carboxylate (Intermediate 24) using 4-(bromomethyl)-1-chloro-3-fluorobenzene. Triethylsilane (2.157 mL 13.50 mmol) was added dropwise to a suspension of palladium on carbon (10% wt, 287 mg, 0.270 mmol) and tert-butyl 4-(4-chloro-2-fluorobenzylidene)piperidine-1-carboxylate (880 mg, 2.70 mmol) in methanol (50 mL) under nitrogen at 0° C. The reaction was stirred at room temperature for 15 minutes. The suspension was filtered through diatomaceous earth and the filtrate concentrated in vacuo to afford tert-butyl 4-(4-chloro-2-fluorobenzyl)piperidine-1-carboxylate as a colourless oil (quantitative). This was then taken up in methanol (25 mL) and HCl (4 M solution in dioxane, 1.35 mL) was added and the reaction was stirred at room temperature overnight. The reaction was concentrated in vacuo and azeotroped with toluene to give 4-(4-chloro-2-fluorobenzyl)piperidine hydrochloride (0.715 g, 2.71 mmol, 100% yield) as a white solid.

The title compound was prepared as described for 4-(3,4-dichlorophenoxy)-1-[(1,3,5-trimethyl-1H-pyrazol-4-yl)sulfonyl]piperidine (Example 1) from 3,5-dimethyl-1H-pyrazole-4-sulfonyl chloride (Intermediate 3) and 4-(4-chloro-2-fluorobenzyl)piperidine hydrochloride (described above).

$^1$H NMR (400 MHz, DMSO-d$_6$) δ ppm 1.13-1.29 (m, 2H) 1.44-1.57 (m, 1H) 1.57-1.67 (m, 2H) 2.18-2.33 (m, 10H) 3.48-3.59 (m, 2H) 7.18-7.24 (m, 1H) 7.25-7.32 (m, 1H) 7.32-7.37 (m, 1H) 13.01 (br. s, 1H)

MS: ES+ 386

Example 83 4-(4-Chloro-2-fluorobenzyl)-1-((1,3,5-trimethyl-1H-pyrazol-4-yl)sulfonyl)piperidine

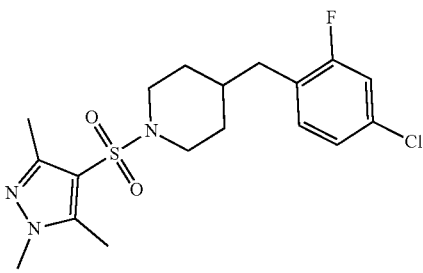 [SMILES: Cc1nn(C)c(C)c1S(=O)(=O)N1CCC(Cc2ccc(Cl)cc2F)CC1]

Prepared as described for 4-(4-Chloro-2-fluorobenzyl)-1-((3,5-dimethyl-1H-pyrazol-4-yl)sulfonyl)piperidine (Example 82) from 1,3,5-trimethyl-1H-pyrazole-4-sulfonyl chloride.

$^1$H NMR (400 MHz, DMSO-d$_6$) δ ppm 1.14-1.28 (m, 2H) 1.43-1.55 (m, 1H) 1.57-1.66 (m, 2H) 2.17-2.27 (m, 5H) 2.37 (s, 3H) 2.53-2.56 (m, 2H) 3.50-3.58 (m, 2H) 3.69 (s, 3H) 7.18-7.23 (m, 1H) 7.25-7.32 (m, 1H) 7.32-7.38 (m, 1H)

MS: ES+ 400

Example 84 5-Chloro-3-methoxy-2-((1-((1,3,5-trimethyl-1H-pyrazol-4-yl)sulfonyl)piperidin-4-yl)oxy)pyridine

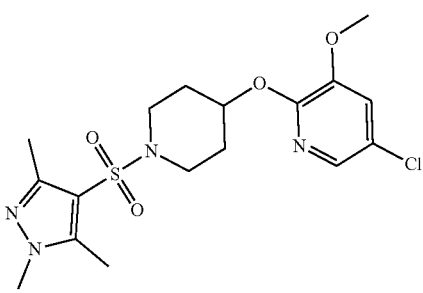 [SMILES: COc1cc(Cl)cnc1OC1CCN(S(=O)(=O)c2c(C)nn(C)c2C)CC1]

Sodium methoxide (0.053 g, 0.99 mmol) was added to a solution of 5-chloro-3-fluoro-2-((1-((1,3,5-trimethyl-1H-pyrazol-4-yl)sulfonyl)piperidin-4-yl)oxy)pyridine (Example 77, 0.2 g, 0.49 mmol) in methanol (1 mL) under nitrogen, then heated to reflux for 5 hours. The reaction was concentrated and diluted with DCM and water. The phases were separated and the organic was dried (Na$_2$SO$_4$) and concentrated in vacuo. The crude product was purified by column chromatography on silica, eluted with 0-70% ethyl acetate/hexane to afford 5-chloro-3-methoxy-2-((1-((1,3,5-trimethyl-1H-pyrazol-4-yl)sulfonyl)piperidin-4-yl)oxy)pyridine (0.11 g, 55% yield).

$^1$H NMR (400 MHz, DMSO-d$_6$) δ ppm 1.66-1.77 (m, 2H) 2.00-2.10 (m, 2H) 2.26 (s, 3H) 2.41 (s, 3H) 2.75-2.83 (m, 2H) 3.26-3.33 (m, 2H) 3.73 (s, 3H) 3.79 (s, 3H) 4.95-5.03 (m, 1H) 7.40-7.45 (m, 1H) 7.67-7.70 (m, 1H)

MS: ES+ 415

Example 85 5-Chloro-2-((1-((3,5-dimethyl-1H-pyrazol-4-yl)sulfonyl)piperidin-4-yl)oxy)-3-methoxypyridine

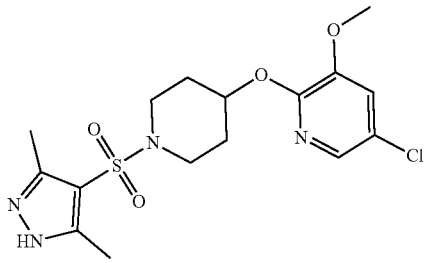 [SMILES: COc1cc(Cl)cnc1OC1CCN(S(=O)(=O)c2c(C)n[nH]c2C)CC1]

Prepared as described for 5-chloro-3-methoxy-2-((1-((1,3,5-trimethyl-1H-pyrazol-4-yl)sulfonyl)piperidin-4-yl)oxy)pyridine (Example 84) from 5-chloro-2-((1-((3,5-dimethyl-1H-pyrazol-4-yl)sulfonyl)piperidin-4-yl)oxy)-3-fluoropyridine (prepared as described for 5-chloro-3-fluoro-2-((1-((1,3,5-trimethyl-1H-pyrazol-4-yl)sulfonyl)piperidin-4-yl)oxy)pyridine (Example 77) using 3,5-dimethyl-1H-pyrazole-4-sulfonyl chloride (Intermediate 3)). $^1$H NMR (400 MHz, DMSO-d$_6$) δ ppm 1.66-1.78 (m, 2H) 2.03 (br. s., 2H) 2.27 (br. s., 3H) 2.37 (br. s., 3H) 2.79-2.89 (m, 2H) 3.23-3.31 (m, 2H) 3.78 (s, 3H) 4.97-5.05 (m, 1H) 7.41-7.44 (m, 1H) 7.67-7.70 (m, 1H) 13.09 (br. s., 1H)

MS: ES+ 401

Example 86 4-(4-Chloro-2-methoxybenzyl)-1-((3,5-dimethyl-1H-pyrazol-4-yl)sulfonyl)-4-methoxypiperidine

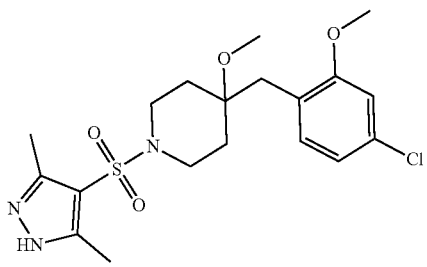 [SMILES: COc1cc(Cl)ccc1CC1(OC)CCN(S(=O)(=O)c2c(C)n[nH]c2C)CC1]

Prepared as described for 4-(3,4-dichlorophenoxy)-1-[(1,3,5-trimethyl-1H-pyrazol-4-yl)sulfonyl]piperidine (Example 1) from 3,5-dimethyl-1H-pyrazole-4-sulfonyl chloride (Intermediate 3) and 4-(4-chloro-2-methoxybenzyl)-4-methoxypiperidine hydrochloride (Intermediate 33).

$^1$H NMR (400 MHz, DMSO-d$_6$) δ ppm 1.38-1.48 (m, 2H) 1.67-1.75 (m, 2H) 2.29 (s, 6H) 2.39-2.48 (m, 2H) 2.72 (s, 2H) 3.14 (s, 3H) 3.26-3.31 (m, 2H) 3.78 (s, 3H) 6.91-6.95 (m, 1H) 7.01-7.03 (m, 1H) 7.07-7.12 (m, 1H) 13.01 (br. s, 1H)

MS: ES+ 428

Example 87 4-(4-Chloro-2-methoxybenzyl)-4-methoxy-1-((1,3,5-trimethyl-1H-pyrazol-4-yl)sulfonyl)piperidine

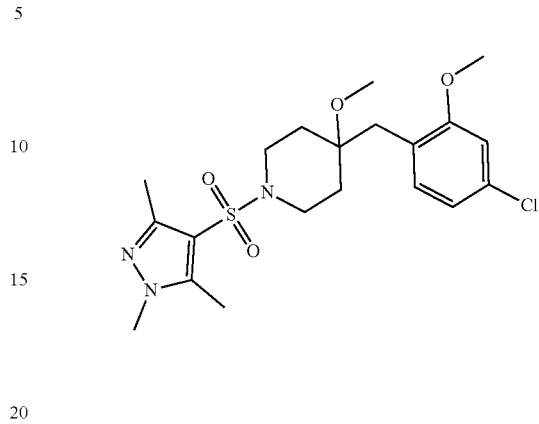

Prepared as described for 4-(3,4-dichlorophenoxy)-1-[(1,3,5-trimethyl-1H-pyrazol-4-yl)sulfonyl]piperidine (Example 1) from 1,3,5-trimethyl-1H-pyrazole-4-sulfonyl chloride and 4-(4-chloro-2-methoxybenzyl)-4-methoxypiperidine hydrochloride (Intermediate 33).

$^1$H NMR (400 MHz, DMSO-d$_6$) δ ppm 1.37-1.48 (m, 2H) 1.67-1.75 (m, 2H) 2.22 (s, 3H) 2.37 (s, 3H) 2.39-2.48 (m, 2H) 2.72 (s, 2H) 3.14 (s, 3H) 3.29 (br. s., 2H) 3.71 (s, 3H) 3.78 (s, 3H) 6.90-6.96 (m, 1H) 7.00-7.05 (m, 1H) 7.07-7.12 (m, 1H)

MS: ES+ 442

Example 88 4-(4-Chloro-2-methoxybenzyl)-1-((1,3,5-trimethyl-1H-pyrazol-4-yl)sulfonyl)piperidin-4-ol

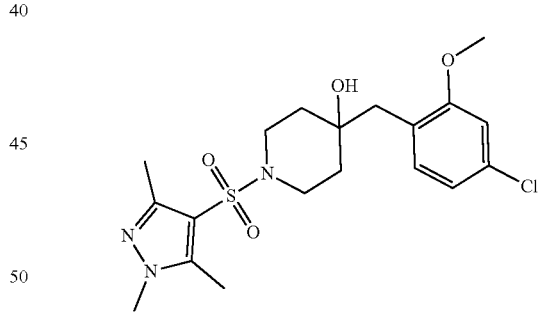

Prepared as described for 4-(3,4-dichlorophenoxy)-1-[(1,3,5-trimethyl-1H-pyrazol-4-yl)sulfonyl]piperidine (Example 1) from 1,3,5-trimethyl-1H-pyrazole-4-sulfonyl chloride and 4-(4-chloro-2-methoxybenzyl)piperidin-4-ol hydrochloride (Intermediate 34).

$^1$H NMR (400 MHz, DMSO-d$_6$) δ ppm 1.40-1.53 (m, 4H) 2.22 (s, 3H) 2.37 (s, 3H) 2.53-2.61 (m, 2H) 2.65 (s, 2H) 3.23-3.30 (m, 2H) 3.71 (s, 3H) 3.77 (s, 3H) 4.29 (s, 1H) 6.89-6.94 (m, 1H) 6.99-7.02 (m, 1H) 7.13-7.18 (m, 1H)

MS: ES+ 428

Example 89 4-(4-Chloro-2-methoxybenzyl)-1-((3,5-dimethyl-1H-pyrazol-4-yl)sulfonyl)piperidin-4-ol

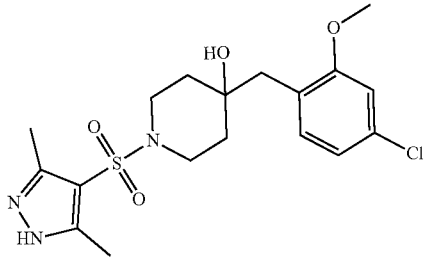 [SMILES: COc1cc(Cl)ccc1CC1(O)CCN(S(=O)(=O)c2c(C)n[nH]c2C)CC1]

Prepared as described for 4-(3,4-dichlorophenoxy)-1-[(1,3,5-trimethyl-1H-pyrazol-4-yl)sulfonyl]piperidine (Example 1) from 3,5-dimethyl-1H-pyrazole-4-sulfonyl chloride (Intermediate 3) and 4-(4-chloro-2-methoxybenzyl)piperidin-4-ol hydrochloride (Intermediate 34).

$^1$H NMR (400 MHz, DMSO-$d_6$) δ ppm 1.38-1.53 (m, 4H) 2.29 (s, 6H) 2.53-2.62 (m, 2H) 2.65 (s, 2H) 3.21-3.30 (m, 2H) 3.77 (s, 3H) 4.29 (s, 1H) 6.89-6.94 (m, 1H) 6.98-7.03 (m, 1H) 7.14-7.19 (m, 1H) 13.02 (br. s, 1H)

MS: ES+ 414

Example 90 4-(4-Chloro-2-methoxybenzyl)-1-((3,5-dimethyl-1H-pyrazol-4-yl)sulfonyl)-4-fluoropiperidine

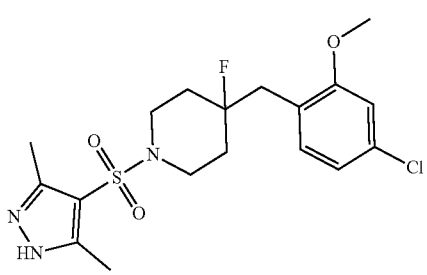 [SMILES: COc1cc(Cl)ccc1CC1(F)CCN(S(=O)(=O)c2c(C)n[nH]c2C)CC1]

Prepared as described for 4-(3,4-dichlorophenoxy)-1-[(1,3,5-trimethyl-1H-pyrazol-4-yl)sulfonyl]piperidine (Example 1) from 3,5-dimethyl-1H-pyrazole-4-sulfonyl chloride (Intermediate 3) and 4-(4-chloro-2-methoxybenzyl)-4-fluoropiperidine hydrochloride (Intermediate 35).

$^1$H NMR (400 MHz, DMSO-$d_6$) δ ppm 1.61-1.71 (m, 1H) 1.71-1.80 (m, 3H) 2.30 (s, 6H) 2.53-2.58 (m, 2H) 2.86-2.95 (m, 2H) 3.37-3.46 (m, 2H) 3.80 (s, 3H) 6.92-6.97 (m, 1H) 7.03-7.07 (m, 1H) 7.11-7.16 (m, 1H) 12.92-13.02 (m, 1H)

MS: ES+ 416

Example 91 4-(4-Chloro-2-methoxybenzyl)-4-fluoro-1-((1,3,5-trimethyl-1H-pyrazol-4-yl)sulfonyl)piperidine

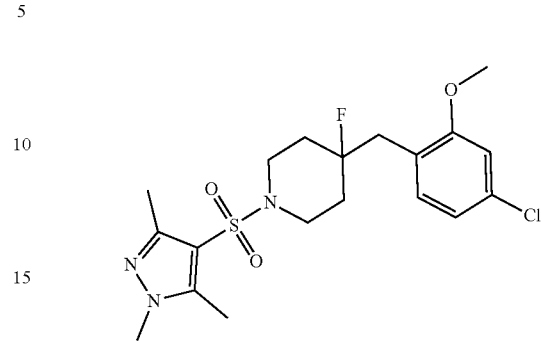

Prepared as described for 4-(3,4-dichlorophenoxy)-1-[(1,3,5-trimethyl-1H-pyrazol-4-yl)sulfonyl]piperidine (Example 1) from 1,3,5-trimethyl-1H-pyrazole-4-sulfonyl chloride and 4-(4-chloro-2-methoxybenzyl)-4-fluoropiperidine hydrochloride (Intermediate 35).

$^1$H NMR (400 MHz, DMSO-$d_6$) δ ppm 1.61-1.70 (m, 1H) 1.70-1.79 (m, 3H) 2.23 (s, 3H) 2.38 (s, 3H) 2.39-2.48 (m, 2H) 2.85-2.94 (m, 2H) 3.38-3.46 (m, 2H) 3.71 (s, 3H) 3.79 (s, 3H) 6.93-6.98 (m, 1H) 7.04-7.09 (m, 1H) 7.10-7.15 (m, 1H)

MS: ES+ 430

Example 92 2-(4-Chloro-2-fluorophenyl)-2-(1-((3,5-dimethyl-1H-pyrazol-4-yl)sulfonyl)piperidin-4-yl)acetonitrile

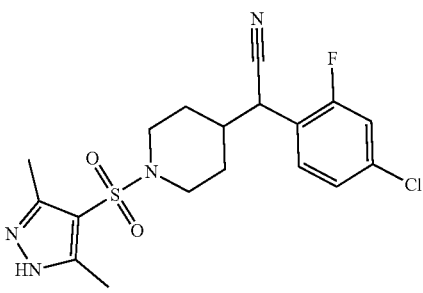 [SMILES: Cc1n[nH]c(C)c1S(=O)(=O)N1CCC(C(C#N)c2ccc(Cl)cc2F)CC1]

Prepared as described for 4-(3,4-dichlorophenoxy)-1-[(1,3,5-trimethyl-1H-pyrazol-4-yl)sulfonyl]piperidine (Example 1) from 3,5-dimethyl-1H-pyrazole-4-sulfonyl chloride (Intermediate 3) and 2-(4-Chloro-2-fluorophenyl)-2-(piperidin-4-yl)acetonitrile hydrochloride (Intermediate 37).

$^1$H NMR (400 MHz, DMSO-$d_6$) δ ppm 1.37-1.44 (m, 1H) 1.46-1.55 (m, 1H) 1.83-1.91 (m, 1H) 2.20-2.28 (m, 5H) 2.33 (s, 5H) 3.53-3.60 (m, 1H) 3.61-3.68 (m, 1H) 4.34-4.41 (m, 1H) 7.37-7.41 (m, 1H) 7.42-7.49 (m, 1H) 7.54-7.59 (m, 1H) 13.05 (br. s., 1H)

MS: ES+ 411

Example 93 2-(4-Chlorophenyl)-2-(1-((3,5-dimethyl-1H-pyrazol-4-yl)sulfonyl)piperidin-4-yl)acetonitrile

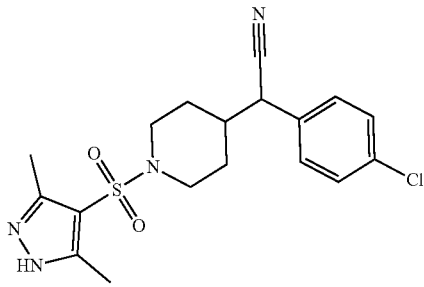 [SMILES: Cc1n[nH]c(C)c1S(=O)(=O)N1CCC(C(C#N)c2ccc(Cl)cc2)CC1]

Prepared as described for 4-(3,4-dichlorophenoxy)-1-[(1,3,5-trimethyl-1H-pyrazol-4-yl)sulfonyl]piperidine (Example 1) from 3,5-dimethyl-1H-pyrazole-4-sulfonyl chloride (Intermediate 3) and 2-(4-chlorophenyl)-2-(piperidin-4-yl)acetonitrile hydrochloride (Intermediate 39).

$^1$H NMR (400 MHz, DMSO-$d_6$) δ ppm 1.20-1.41 (m, 2H) 1.50-1.58 (m, 1H) 1.75-1.92 (m, 2H) 2.17-2.33 (m, 8H) 3.53-3.68 (m, 2H) 4.20-4.27 (m, 1H) 7.33-7.38 (m, 2H) 7.46-7.51 (m, 2H) 13.03 (br. s., 1H)

MS: ES+ 393

Example 94 (4-Chlorophenyl)(1-((3,5-dimethyl-1H-pyrazol-4-yl)sulfonyl)piperidin-4-yl)methanol

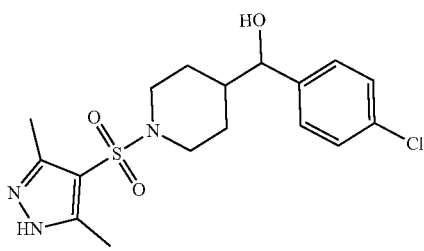 [SMILES: Cc1n[nH]c(C)c1S(=O)(=O)N1CCC(C(O)c2ccc(Cl)cc2)CC1]

Prepared as described for 4-(3,4-dichlorophenoxy)-1-[(1,3,5-trimethyl-1H-pyrazol-4-yl)sulfonyl]piperidine (Example 1) from 3,5-dimethyl-1H-pyrazole-4-sulfonyl chloride (Intermediate 3) and (4-chlorophenyl)(piperidin-4-yl)methanol hydrochloride (Intermediate 42).

$^1$H NMR (400 MHz, DMSO-$d_6$) δ ppm 1.14-1.36 (m, 3H) 1.36-1.51 (m, 1H) 1.75-1.85 (m, 1H) 2.09-2.38 (m, 8H) 3.47-3.66 (m, 2H) 4.24-4.33 (m, 1H) 5.27-5.36 (m, 1H) 7.23-7.31 (m, 2H) 7.32-7.42 (m, 2H) 13.00 (br. s., 1H)

MS: ES+ 384

Example 95 (4-Chlorophenyl)(1-((1,3,5-trimethyl-1H-pyrazol-4-yl)sulfonyl)piperidin-4-yl)methanol

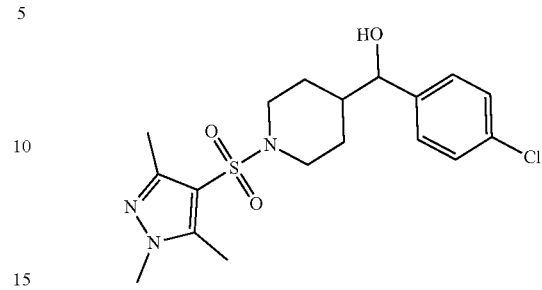

Prepared as described for 4-(3,4-dichlorophenoxy)-1-[(1,3,5-trimethyl-1H-pyrazol-4-yl)sulfonyl]piperidine (Example 1) from 1,3,5-trimethyl-1H-pyrazole-4-sulfonyl chloride and (4-chlorophenyl)(piperidin-4-yl)methanol hydrochloride (Intermediate 42).

$^1$H NMR (400 MHz, DMSO-$d_6$) δ ppm 1.16-1.35 (m, 3H) 1.37-1.49 (m, 1H) 1.74-1.84 (m, 1H) 2.09-2.19 (m, 2H) 2.21 (s, 3H) 2.36 (s, 3H) 3.48-3.63 (m, 2H) 3.69 (s, 3H) 4.25-4.32 (m, 1H) 5.27-5.33 (m, 1H) 7.25-7.31 (m, 2H) 7.33-7.39 (m, 2H)

MS: ES+ 398

Example 96 4-((4-Chlorophenyl)(methoxy)methyl)-1-((3,5-dimethyl-1H-pyrazol-4-yl)sulfonyl)piperidine

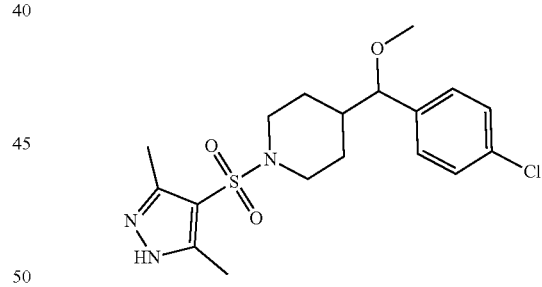

Prepared as described for 4-(3,4-dichlorophenoxy)-1-[(1,3,5-trimethyl-1H-pyrazol-4-yl)sulfonyl]piperidine (Example 1) from 3,5-dimethyl-1H-pyrazole-4-sulfonyl chloride (Intermediate 3) and 4-((4-chlorophenyl)(methoxy)methyl)piperidine hydrochloride (Intermediate 43).

$^1$H NMR (400 MHz, DMSO-$d_6$) δ ppm 1.12-1.30 (m, 3H) 1.45-1.59 (m, 1H) 1.90-1.98 (m, 1H) 2.08-2.37 (m, 8H) 3.07 (s, 3H) 3.46-3.65 (m, 2H) 3.88-3.95 (m, 1H) 7.21-7.29 (m, 2H) 7.37-7.45 (m, 2H) 13.00 (br. s., 1H)

MS: ES+ 398

Example 97 4-((4-Chlorophenyl)(methoxy)methyl)-1-((3,5-dimethyl-1H-pyrazol-4-yl)sulfonyl)piperidine, Enantiomer A

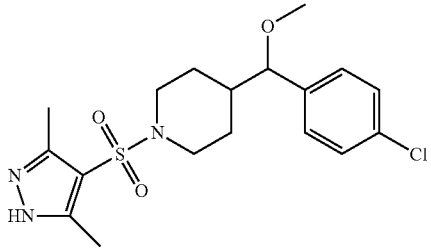 [SMILES: COC(c1ccc(Cl)cc1)C1CCN(S(=O)(=O)c2c(C)n[nH]c2C)CC1]

4-((4-Chlorophenyl)(methoxy)methyl)-1-((3,5-dimethyl-1H-pyrazol-4-yl)sulfonyl)piperidine (Example 96) was separated into its enantiomers by supercritical fluid chromatography using a Daicel AD-H (250 mm×10 mm) column, eluting with 14% MeOH to give 4-((4-chlorophenyl)(methoxy)methyl)-1-((3,5-dimethyl-1H-pyrazol-4-yl)sulfonyl)piperidine, Enantiomer A, as the first eluting peak. e.e. 100%

$^1$H NMR (400 MHz, DMSO-$d_6$) δ ppm 1.12-1.30 (m, 3H) 1.45-1.59 (m, 1H) 1.90-1.98 (m, 1H) 2.08-2.37 (m, 8H) 3.07 (s, 3H) 3.46-3.65 (m, 2H) 3.88-3.95 (m, 1H) 7.21-7.29 (m, 2H) 7.37-7.45 (m, 2H) 13.00 (br. s., 1H)

MS: ES+ 398

Example 98 4-((4-Chlorophenyl)(methoxy)methyl)-1-((3,5-dimethyl-1H-pyrazol-4-yl)sulfonyl)piperidine, Enantiomer B

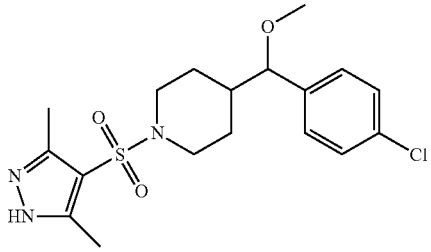 [SMILES: COC(c1ccc(Cl)cc1)C1CCN(S(=O)(=O)c2c(C)n[nH]c2C)CC1]

4-((4-Chlorophenyl)(methoxy)methyl)-1-((3,5-dimethyl-1H-pyrazol-4-yl)sulfonyl)piperidine (Example 96) was separated into its enantiomers by supercritical fluid chromatography using a Daicel AD-H (250 mm×10 mm) column, eluting with 14% MeOH to give 4-((4-chlorophenyl)(methoxy)methyl)-1-((3,5-dimethyl-1H-pyrazol-4-yl)sulfonyl)piperidine, Enantiomer B, as the second eluting peak. e.e. 100%

$^1$H NMR (400 MHz, DMSO-$d_6$) δ ppm 1.12-1.30 (m, 3H) 1.45-1.59 (m, 1H) 1.90-1.98 (m, 1H) 2.08-2.37 (m, 8H) 3.07 (s, 3H) 3.46-3.65 (m, 2H) 3.88-3.95 (m, 1H) 7.21-7.29 (m, 2H) 7.37-7.45 (m, 2H) 13.00 (br. s., 1H)

MS: ES+ 398

Example 99 4-((4-Chlorophenyl)(methoxy)methyl)-1-((1,3,5-trimethyl-1H-pyrazol-4-yl)sulfonyl)piperidine

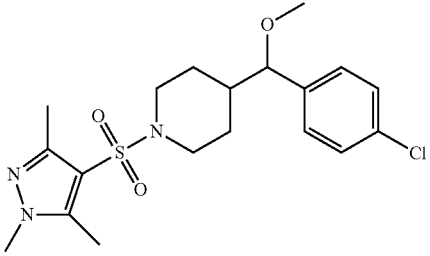 [SMILES: COC(c1ccc(Cl)cc1)C1CCN(S(=O)(=O)c2c(C)nn(C)c2C)CC1]

Prepared as described for 4-(3,4-dichlorophenoxy)-1-[(1,3,5-trimethyl-1H-pyrazol-4-yl)sulfonyl]piperidine (Example 1) from 1,3,5-trimethyl-1H-pyrazole-4-sulfonyl chloride and 4-((4-chlorophenyl)(methoxy)methyl)piperidine hydrochloride (Intermediate 43). $^1$H NMR (400 MHz, DMSO-$d_6$) δ ppm 1.10-1.30 (m, 3H) 1.45-1.57 (m, 1H) 1.86-1.98 (m, 1H) 2.07-2.18 (m, 1H) 2.19-2.23 (m, 4H) 2.36 (s, 3H) 3.07 (s, 3H) 3.46-3.62 (m, 2H) 3.69 (s, 3H) 3.90-3.94 (m, 1H) 7.22-7.28 (m, 2H) 7.38-7.44 (m, 2H)

MS: ES+ 412

Example 100 2-(4-Chlorophenyl)-2-(1-((3,5-dimethyl-1H-pyrazol-4-yl)sulfonyl)piperidin-4-yl)ethanol

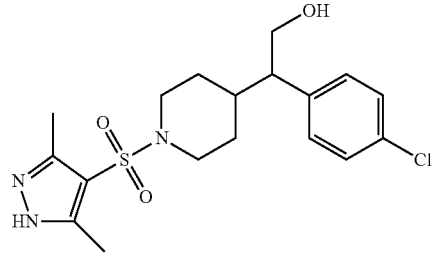 [SMILES: Cc1n[nH]c(C)c1S(=O)(=O)N1CCC(C(CO)c2ccc(Cl)cc2)CC1]

2-(4-Chlorophenyl)-2-(piperidin-4-yl)ethanol hydrochloride (Intermediate 45, 0.7 g, 2.1 mmol) was dissolved in HCl (12% in dioxane, 3 mL) and stirred at room temperature for 4 hours. The reaction was concentrated in vacuo and the crude product was triturated with diethyl ether to give 2-(4-chlorophenyl)-2-(piperidin-4-yl)ethanol hydrochloride (0.4 g, 82%).

The title compound was prepared as described for 4-(3,4-dichlorophenoxy)-1-[(1,3,5-trimethyl-1H-pyrazol-4-yl)sulfonyl]piperidine (Example 1) from 3,5-dimethyl-1H-pyrazole-4-sulfonyl chloride (Intermediate 3) and 2-(4-chlorophenyl)-2-(piperidin-4-yl)ethanol hydrochloride.

$^1$H NMR (400 MHz, DMSO-$d_6$) δ ppm 0.93-1.06 (m, 1H) 1.12-1.37 (m, 3H) 1.54-1.67 (m, 1H) 1.89-1.99 (m, 1H) 2.06-2.15 (m, 1H) 2.18-2.26 (m, 4H) 2.32 (s, 3H) 3.44-3.51 (m, 1H) 3.55-3.68 (m, 3H) 4.50-4.55 (m, 1H) 7.16-7.22 (m, 2H) 7.28-7.35 (m, 2H) 13.04 (s, 1H)

MS: ES+ 398

Example 101 1-(4-Chlorophenyl)-1-(1-((3,5-dimethyl-1H-pyrazol-4-yl)sulfonyl)piperidin-4-yl)ethanol

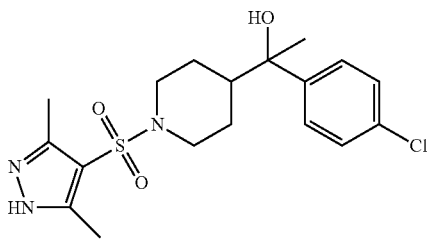 [SMILES: Cc1n[nH]c(C)c1S(=O)(=O)N1CCC(C(C)(O)c2ccc(Cl)cc2)CC1]

Methylmagnesium bromide (3M in ether) (3.09 mL, 9.26 mmol) was added slowly to a solution of tert-butyl 4-(4-chlorobenzoyl)piperidine-1-carboxylate (Intermediate 40, 0.5 g, 1.544 mmol) in THF (10 mL) at 0° C. under nitrogen. The reaction was stirred at room temperature for 2 hours. The reaction was quenched with 2M HCl and partitioned between ethyl acetate and 2M HCl. The phases were separated and the aqueous phase was extracted with ethyl acetate. The combined organics were washed with saturated brine, dried (phase separator) and concentrated in vacuo to afford tert-butyl 4-(1-(4-chlorophenyl)-1-hydroxyethyl)piperidine-1-carboxylate (0.481 g, 1.415 mmol, 92% yield) as a colourless oil.

MS: ES– 338.

Hydrogen chloride (4M in dioxane) (0.309 mL, 1.236 mmol) was added to a solution of tert-butyl 4-(1-(4-chlorophenyl)-1-hydroxyethyl)piperidine-1-carboxylate (0.21 g, 0.618 mmol) in methanol (10 mL). The reaction was stirred at room temperature overnight. The solution was concentrated and azeotroped with toluene to give 1-(4-chlorophenyl)-1-(piperidin-4-yl)ethanol hydrochloride as a white solid (quantitative, MS: ES+ 240).

The title compound was prepared as described for 4-(3,4-dichlorophenoxy)-1-[(1,3,5-trimethyl-1H-pyrazol-4-yl)sulfonyl]piperidine (Example 1) from 3,5-dimethyl-1H-pyrazole-4-sulfonyl chloride (Intermediate 3) and 1-(4-chlorophenyl)-1-(piperidin-4-yl)ethanol hydrochloride.

$^1$H NMR (400 MHz, DMSO-$d_6$) δ ppm 1.15-1.33 (m, 3H) 1.37 (s, 3H) 1.43-1.54 (m, 1H) 1.66-1.77 (m, 1H) 2.01-2.20 (m, 2H) 2.27 (s, 6H) 3.48-3.66 (m, 2H) 4.95 (s, 1H) 7.31-7.35 (m, 2H) 7.36-7.41 (m, 2H) 13.00 (br. s., 1H)

MS: ES+ 398

Example 102 4-(1-(4-Chlorophenyl)ethyl)-1-((3,5-dimethyl-1H-pyrazol-4-yl)sulfonyl)piperidine

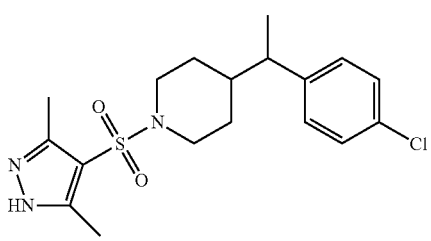 [SMILES: Cc1n[nH]c(C)c1S(=O)(=O)N1CCC(C(C)c2ccc(Cl)cc2)CC1]

p-Toluenesulfonic acid monohydrate (0.963 g, 5.06 mmol) was added to a solution of tert-butyl 4-(1-(4-chlorophenyl)-1-hydroxyethyl)piperidine-1-carboxylate (described in the preparation of Example 101), (0.43 g, 1.265 mmol) in toluene (15 mL) under nitrogen. Magnesium sulfate was added and the reaction was heated to reflux for 5 hours then cooled overnight. The reaction was quenched with 2M NaOH and the mixture was partitioned between ethyl acetate and water. The phases were separated and the aqueous extracted with ethyl acetate, the combined organics were washed with saturated brine, dried (phase separator) and concentrated in vacuo to give crude 4-(1-(4-chlorophenyl)ethylidene)piperidine 4-methylbenzenesulfonate. Triethylamine (0.386 mL, 2.77 mmol) was added to a suspension of crude 4-(1-(4-chlorophenyl)ethylidene)piperidine 4-methylbenzenesulfonate (0.364 g, 0.924 mmol) and 3,5-dimethyl-1H-pyrazole-4-sulfonyl chloride (Intermediate 3, 0.216 g, 1.109 mmol) in dichloromethane (10 mL). The reaction was stirred at room temperature for 4 hours. The mixture was diluted with DCM, washed with water, dried (phase separator) and concentrated in vacuo. The crude product was purified by column chromatography on silica, eluted with 0-100% ethyl acetate/petroleum ether, then by reverse phase preparative HPLC eluted with acetonitrile/water (with 0.1% ammonia) to afford 4-(1-(4-chlorophenyl)ethylidene)-1-((3,5-dimethyl-1H-pyrazol-4-yl)sulfonyl)piperidine. This was then taken in a flask with platinum(IV) oxide (3.47 mg, 0.015 mmol) and evacuated and purged with nitrogen three times. Ethanol (0.5 mL) and ethyl acetate (0.5 mL) were added under vacuum, then the suspension was stirred under an atmosphere of hydrogen for 1 hour. The suspension was filtered through diatomaceous earth and the filtrate concentrated in vacuo. The crude product was purified by reverse phase preparative HPLC eluted with acetonitrile/water (with 0.1% ammonia) to afford 4-(1-(4-chlorophenyl)ethyl)-1-((3,5-dimethyl-1H-pyrazol-4-yl)sulfonyl)piperidine (0.024 g, 0.063 mmol, 41.2% yield) as a white foam.

$^1$H NMR (400 MHz, DMSO-$d_6$) δ ppm 0.97-1.09 (m, 1H) 1.11-1.22 (m, 4H) 1.27-1.43 (m, 2H) 1.84-1.92 (m, 1H) 2.06-2.15 (m, 1H) 2.16-2.25 (m, 1H) 2.26-2.31 (m, 7H) 3.45-3.66 (m, 2H) 7.16-7.21 (m, 2H) 7.30-7.34 (m, 2H) 12.99 (br. s, 1H)

MS: ES+ 382

Example 103 N-(4-Chlorophenyl)-1-((3,5-dimethyl-1H-pyrazol-4-yl)sulfonyl)piperidin-4-amine

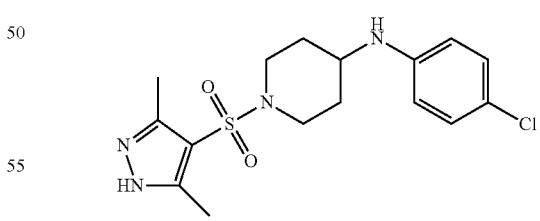

Prepared as described for 4-(3,4-dichlorophenoxy)-1-[(1,3,5-trimethyl-1H-pyrazol-4-yl)sulfonyl]piperidine (Example 1) from 3,5-dimethyl-1H-pyrazole-4-sulfonyl chloride (Intermediate 3) and N-(4-chlorophenyl)piperidin-4-amine hydrochloride.

$^1$H NMR (400 MHz, MeOD-$d_6$) δ ppm 1.32-1.45 (m, 4H) 2.10-2.18 (m, 2H) 2.45 (s, 6H) 2.67-2.80 (m, 2H) 3.62-3.71 (m, 2H) 4.10 (s, 1H) 6.54-6.61 (m, 2H) 7.08-7.12 (m, 2H)

MS: ES+ 369

Example 104 4-((4-Chlorophenyl)(ethoxy)methyl)-1-((3,5-dimethyl-1H-pyrazol-4-yl)sulfonyl)piperidine

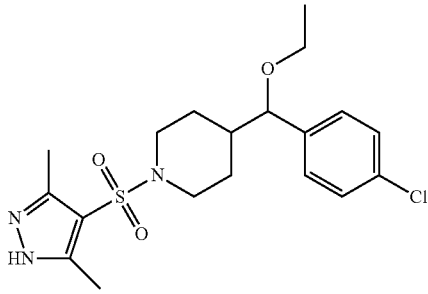 [SMILES: CCOC(c1ccc(Cl)cc1)C1CCN(S(=O)(=O)c2c(C)n[nH]c2C)CC1]

Prepared as described for 4-(3,4-dichlorophenoxy)-1-[(1,3,5-trimethyl-1H-pyrazol-4-yl)sulfonyl]piperidine (Example 1) from 3,5-dimethyl-1H-pyrazole-4-sulfonyl chloride (Intermediate 3) and 4-((4-chlorophenyl)(ethoxy)methyl)piperidine hydrochloride (Intermediate 46).

$^1$H NMR (400 MHz, DMSO-$d_6$) δ ppm 1.01-1.10 (m, 3H) 1.16-1.30 (m, 3H) 1.49 (br. s., 1H) 1.90-1.97 (m, 1H) 2.10-2.24 (m, 2H) 2.24-2.31 (m, 6H) 3.18-3.26 (m, 2H) 3.48-3.63 (m, 2H) 3.99-4.04 (m, 1H) 7.23-7.28 (m, 2H) 7.37-7.43 (m, 2H) 13.00 (br. s., 1H)

MS: ES+ 412

Example 105 4-((4-Chlorophenyl)fluoromethyl)-1-((3,5-dimethyl-1H-pyrazol-4-yl)sulfonyl)piperidine

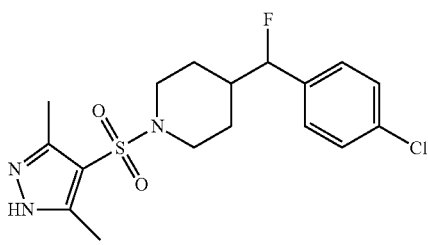 [SMILES: Cc1n[nH]c(C)c1S(=O)(=O)N1CCC(C(F)c2ccc(Cl)cc2)CC1]

Prepared as described for 4-(3,4-dichlorophenoxy)-1-[(1,3,5-trimethyl-1H-pyrazol-4-yl)sulfonyl]piperidine (Example 1) from 3,5-dimethyl-1H-pyrazole-4-sulfonyl chloride (Intermediate 3) and 4-((4-chlorophenyl)fluoromethyl)piperidine hydrochloride (Intermediate 47).

$^1$H NMR (400 MHz, DMSO-$d_6$) δ ppm 1.22-1.41 (m, 3H) 1.79-1.91 (m, 2H) 2.17-2.25 (m, 1H) 2.29 (s, 7H) 3.52-3.67 (m, 2H) 5.23-5.41 (m, 1H) 7.32-7.38 (m, 2H) 7.43-7.49 (m, 2H) 13.0 (br. s, 1H)

MS: ES+ 386

Example 106 4-((4-Chlorophenyl)fluoromethyl)-1-((3,5-dimethyl-1H-pyrazol-4-yl)sulfonyl)piperidine Enantiomer A

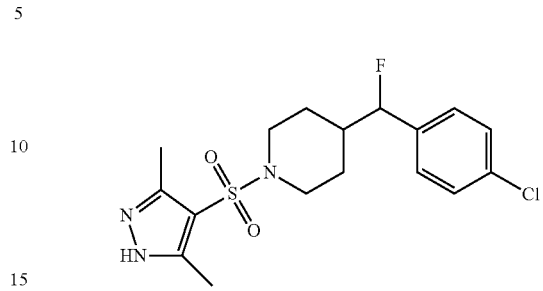

4-((4-Chlorophenyl)fluoromethyl)-1-((3,5-dimethyl-1H-pyrazol-4-yl)sulfonyl)piperidine (Example 105) was separated into its enantiomers by supercritical fluid chromatography using a Chiralpak AD 20×250 mm 5 μm column eluting with 20% methanol to afford 4-((4-chlorophenyl)fluoromethyl)-1-((3,5-dimethyl-1H-pyrazol-4-yl)sulfonyl)piperidine, Enantiomer A, as the first eluting peak.

e.e. 97.9%

$^1$H NMR (400 MHz, DMSO-$d_6$) δ ppm 1.22-1.41 (m, 3H) 1.79-1.91 (m, 2H) 2.17-2.25 (m, 1H) 2.29 (s, 7H) 3.52-3.67 (m, 2H) 5.23-5.41 (m, 1H) 7.32-7.38 (m, 2H) 7.43-7.49 (m, 2H) 13.0 (br. s, 1H)

MS: ES+ 386

Example 107 4-((4-Chlorophenyl)fluoromethyl)-1-((3,5-dimethyl-1H-pyrazol-4-yl)sulfonyl)piperidine Enantiomer B

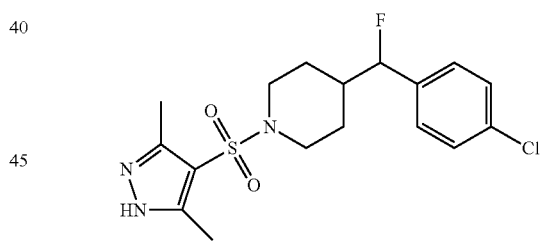

4-((4-Chlorophenyl)fluoromethyl)-1-((3,5-dimethyl-1H-pyrazol-4-yl)sulfonyl)piperidine (Example 105) was separated into its enantiomers by supercritical fluid chromatography using a Chiralpak AD 20×250 mm 5 μm column eluting with 20% methanol to afford 4-((4-chlorophenyl)fluoromethyl)-1-((3,5-dimethyl-1H-pyrazol-4-yl)sulfonyl)piperidine, Enantiomer B, as the second eluting peak.

e.e. 98.1%

$^1$H NMR (400 MHz, DMSO-$d_6$) δ ppm 1.22-1.41 (m, 3H) 1.79-1.91 (m, 2H) 2.17-2.25 (m, 1H) 2.29 (s, 7H) 3.52-3.67 (m, 2H) 5.23-5.41 (m, 1H) 7.32-7.38 (m, 2H) 7.43-7.49 (m, 2H) 13.0 (br. s, 1H)

MS: ES+ 386

Example 108 4-(4-Chlorobenzyl)-1-((3,5-dimethyl-1H-pyrazol-4-yl)sulfonyl)piperidin-4-ol

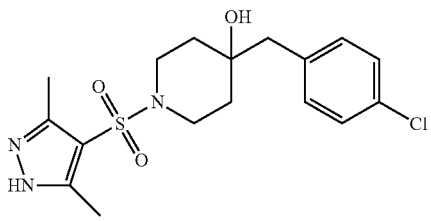 [SMILES: Cc1n[nH]c(C)c1S(=O)(=O)N1CCC(O)(Cc2ccc(Cl)cc2)CC1]

tert-Butyl 4-(4-chlorobenzyl)-4-hydroxypiperidine-1-carboxylate was prepared as described for tert-butyl 4-(3,4-dichlorobenzyl)-4-hydroxypiperidine-1-carboxylate (Intermediate 22). Hydrogen chloride (4M in dioxane) (0.609 mL, 2.437 mmol) was added to a solution of tert-butyl 4-(4-chlorobenzyl)-4-hydroxypiperidine-1-carboxylate (0.25 g, 0.767 mmol) in methanol (5 mL). The reaction was stirred at room temperature overnight, then concentrated and azeotroped with toluene to afford 4-(4-chlorobenzyl)piperidin-4-ol hydrochloride (quantitative). The title compound was prepared as described for 4-(3,4-dichlorophenoxy)-1-[(1,3,5-trimethyl-1H-pyrazol-4-yl)sulfonyl]piperidine (Example 1) from 3,5-dimethyl-1H-pyrazole-4-sulfonyl chloride (Intermediate 3) and 4-(4-chlorobenzyl)piperidin-4-ol hydrochloride.

$^1$H NMR (400 MHz, DMSO-$d_6$) δ ppm 1.36-1.45 (m, 2H) 1.46-1.60 (m, 2H) 2.29 (br. s., 6H) 2.51-2.58 (m, 2H) 2.65 (s, 2H) 3.31-3.37 (m, 2H) 4.33 (s, 1H) 7.17-7.25 (m, 2H) 7.27-7.34 (m, 2H) 13.02 (br. s., 1H)

MS: ES+ 384

Example 109 4-(1-(4-Chlorophenyl)-2-methoxyethyl)-1-((3,5-dimethyl-1H-pyrazol-4-yl)sulfonyl)piperidine

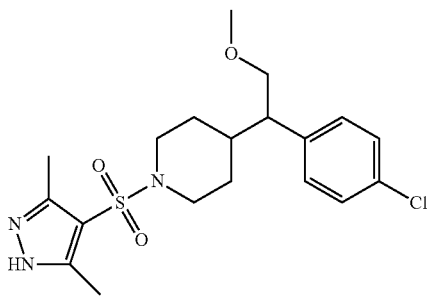 [SMILES: COCC(c1ccc(Cl)cc1)C1CCN(S(=O)(=O)c2c(C)n[nH]c2C)CC1]

Sodium hydride (0.046 g, 1.94 mmol) was added to a solution of tert-butyl 4-(1-(4-chlorophenyl)-2-hydroxyethyl)piperidine-1-carboxylate (Intermediate 45, 0.6 g, 1.76 mmol) in THF (15 mL). The reaction was heated to 60-65° C. for 2 hours then cooled to room temperature. Methyl iodide (0.276 g, 1.94 mmol) and HMPA (0.3 mL) were added and the reaction was refluxed for 15 hours. The reaction was quenched with ice/water and extracted with ethyl acetate. The combined organics were dried (sodium sulfate) and concentrated in vacuo. The crude product was purified by column chromatography on silica, eluted with 0-70% ethyl acetate/n-hexane to afford tert-butyl 4-(1-(4-chlorophenyl)-2-hydroxyethyl)piperidine-1-carboxylate (0.35 g, 56%). This was taken up into dioxane (1 mL), treated with HCl/dioxane (7 mL) and stirred at room temperature overnight. The reaction was concentrated in vacuo and triturated with diethyl ether to afford 4-(1-(4-chlorophenyl)-2-hydroxyethyl)piperidine hydrochloride (0.2 g, 80%). The title compound was prepared as described for 4-(3,4-dichlorophenoxy)-1-[(1,3,5-trimethyl-1H-pyrazol-4-yl)sulfonyl]piperidine (Example 1) from 3,5-dimethyl-1H-pyrazole-4-sulfonyl chloride (Intermediate 3) and 4-(1-(4-chlorophenyl)-2-hydroxyethyl)piperidine hydrochloride.

$^1$H NMR (400 MHz, DMSO-$d_6$) δ ppm 0.95-1.10 (m, 1H) 1.15-1.36 (m, 3H) 1.51-1.64 (m, 1H) 1.85-1.94 (m, 1H) 2.06-2.15 (m, 1H) 2.23 (br. s., 3H) 2.32 (br. s., 3H) 2.58-2.70 (m, 1H) 3.15 (s, 3H) 3.44-3.51 (m, 1H) 3.51-3.56 (m, 2H) 3.57-3.64 (m, 1H) 7.17-7.23 (m, 2H) 7.30-7.35 (m, 2H) 13.03 (br. s., 1H)

MS: ES+ 412

Example 110 1-((3,5-Dimethyl-1H-pyrazol-4-yl)sulfonyl)-4-(methoxy(phenyl)methyl)piperidine

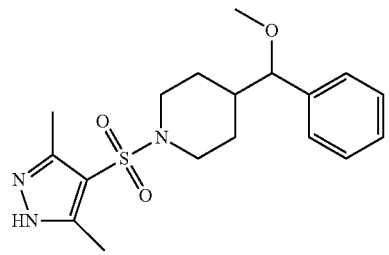 [SMILES: COC(c1ccccc1)C1CCN(S(=O)(=O)c2c(C)n[nH]c2C)CC1]

Prepared as described for 4-(3,4-dichlorophenoxy)-1-[(1,3,5-trimethyl-1H-pyrazol-4-yl)sulfonyl]piperidine (Example 1) from 3,5-dimethyl-1H-pyrazole-4-sulfonyl chloride (Intermediate 3) and 4-(methoxy(phenyl)methyl)piperidine hydrochloride (prepared as described for 4-((4-Chlorophenyl)(methoxy)methyl)piperidine hydrochloride (Intermediate 43) using phenyl(piperidin-4-yl)methanone hydrochloride).

$^1$H NMR (400 MHz, DMSO-$d_6$) δ ppm 1.11-1.31 (m, 3H) 1.48-1.60 (m, 1H) 1.90 (m, 1H) 2.08-2.24 (m, 2H) 2.27 (s, 6H) 3.06 (s, 3H) 3.47-3.63 (m, 2H) 3.84-3.90 (m, 1H) 7.19-7.25 (m, 2H) 7.25-7.31 (m, 1H) 7.32-7.38 (m, 2H) 13.01 (br. s, 1H)

MS: ES+ 364

Example 111 4-(1-(4-Chlorophenyl)-2,2-difluoroethyl)-1-((3,5-dimethyl-1H-pyrazol-4-yl)sulfonyl)piperidine

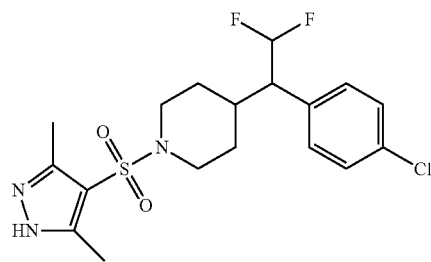 [SMILES: Cc1n[nH]c(C)c1S(=O)(=O)N1CCC(C(c2ccc(Cl)cc2)C(F)F)CC1]

Diethylaminosulfur trifluoride (0.242 mL, 1.835 mmol) was added to a solution of tert-butyl 4-(1-(4-chlorophenyl)-2-oxoethyl)piperidine-1-carboxylate (Intermediate 44, 0.31 g, 0.918 mmol) in DCM (5 mL) under nitrogen at −78° C. The reaction was stirred at −78° C. for 2 hours, then warmed to room temperature overnight. A further portion of diethylaminosulfur trifluoride (0.242 mL, 1.835 mmol) was added and the reaction stirred at room temperature overnight. The reaction was quenched with saturated sodium hydrogen carbonate. The aqueous was extracted with DCM and combined organics were washed with water, dried (phase separator) and concentrated in vacuo. The crude product was purified by column chromatography on silica, eluted with 0-20% ethyl acetate/petroleum ether to afford tert-butyl 4-(1-(4-chlorophenyl)-2,2-difluoroethyl)piperidine-1-carboxylate (0.09 g, 0.250 mmol, 27.3% yield) as a colourless oil. Hydrogen chloride (4M in dioxane) (0.125 mL, 0.500 mmol) was added to a solution of tert-butyl 4-(1-(4-chlorophenyl)-2,2-difluoroethyl)piperidine-1-carboxylate (0.09 g, 0.250 mmol) in methanol (5 mL). The reaction was stirred at room temperature overnight. The solution was concentrated in vacuo and azeotroped with toluene to give 4-(1-(4-chlorophenyl)-2,2-difluoroethyl)piperidine hydrochloride (quantitative) as a colourless oil that was used without further purification. The title compound was prepared as described for 4-(3,4-dichlorophenoxy)-1-[(1,3,5-trimethyl-1H-pyrazol-4-yl)sulfonyl]piperidine (Example 1) from 3,5-dimethyl-1H-pyrazole-4-sulfonyl chloride (Intermediate 3) and 4-(1-(4-chlorophenyl)-2,2-difluoroethyl)piperidine hydrochloride.

$^1$H NMR (400 MHz, DMSO-d$_6$) δ ppm 1.01-1.15 (m, 1H) 1.26-1.40 (m, 2H) 1.77-1.90 (m, 1H) 1.94-2.04 (m, 1H) 2.13-2.22 (m, 1H) 2.28 (s, 7H) 2.96-3.10 (m, 1H) 3.44-3.65 (m, 2H) 6.22-6.55 (m, 1H) 7.24-7.30 (m, 2H) 7.38-7.43 (m, 2H) 13.02 (br. s., 1H)

MS: ES+ 418

3. BIOLOGICAL ASSAY

Prokineticin receptor 1 (PKR1) antagonists may be functionally assessed by measurement of change in intracellular calcium levels induced by Gq mediated increase in inositol triphosphate (IP3) levels. The ability of a compound to block the intracellular release of calcium mediated by PK1 in RBL2H3 cells expressing human PKR1 receptors is determined as a measure of the compound's antagonist activity in vitro.

Approximately 10,000 cells per assay well are seeded in normal culture medium in a 384 well plate (Corning). Twenty-four hours after seeding, the cells are loaded with a calcium sensitive fluorescent dye by replacing the culture medium with assay buffer (1× Hanks buffered saline, mM HEPES, 0.1% w/v fatty acid free BSA (bovine serum albumin), pH 7.4) containing 1 mM probenecid and 1× Calcium 5 Reagent (Molecular Devices). Cells are incubated at 37° C. for 1 hour to allow for dye uptake.

To test for antagonist activity, test compounds at a final concentration range between 0.32 nM-10 μM (diluted in assay buffer) are added to the assay wells and allowed to incubate for 10 minutes prior to stimulation with PK1. After incubation with test compounds the assay plate is placed in a FLIPR Tetra (Molecular Devices) and PK1 (diluted in assay buffer) is added at the determined EC80 concentration (final). Ligand-dependent changes in intracellular calcium levels are determined by measuring changes in fluorescence of the dye at 525 nM following excitation at 485 nM. Readings from wells that do not contain antagonist enable percentage inhibition curves to be plotted using 4-parameter fit algorithm and IC50 values are calculated for each test compound.

Results

| Compound of Example No. | Mean IC$_{50}$ (μM) | Compound of Example No. | Mean IC$_{50}$ (μM) |
|---|---|---|---|
| 1 | 1.4 | 2 | 1 |
| 3 | 1.4 | 4 | 0.82 |
| 5 | 0.53 | 6 | 2.2 |
| 7 | 7.3 | 8 | 1.45 |
| 9 | 2.3 | 10 | 1.7 |
| 11 | 0.86 | 12 | 4.7 |
| 13 | 0.79 | 14 | 0.47 |
| 15 | 2.9 | 16 | 4.6 |
| 17 | 3.6 | 18 | 7 |
| 19 | 5.6 | 20 | 3.6 |
| 21 | 2.1 | 22 | 1.18 |
| 23 | 0.22 | 24 | 1.5 |
| 25 | 1.3 | 26 | 1.7 |
| 27 | 5.6 | 28 | 0.32 |
| 29 | 1.1 | 30 | 0.51 |
| 31 | 0.31 | 32 | 3.4 |
| 33 | 0.44 | 34 | 0.24 |
| 35 | 1.1 | 36 | 1.1 |
| 37 | 7.4 | 38 | 3.2 |
| 39 | 0.21 | 40 | 0.21 |
| 41 | 5.9 | 42 | 5.9 |
| 43 | 6.3 | 44 | 5.1 |
| 45 | 1.4 | 46 | 1 |
| 47 | 1.9 | 48 | 3.8 |
| 49 | 1 | 50 | 2.1 |
| 51 | 1.5 | 52 | 2.7 |
| 53 | 0.9 | 54 | 5.2 |
| 55 | 0.52 | 56 | 0.95 |
| 57 | 1.6 | 58 | 2.4 |
| 59 | 2.4 | 60 | 0.9 |
| 61 | 1.08 | 62 | 0.68 |
| 63 | 0.64 | 64 | 0.89 |
| 65 | 0.94 | 66 | 1.01 |
| 67 | 0.52 | 68 | 2.02 |
| 69 | 6.47 | 70 | 8.62 |
| 71 | 0.78 | 72 | 0.44 |
| 73 | 0.20 | 74 | 0.17 |
| 75 | 6.98 | 76 | 3.73 |
| 77 | 3.19 | 78 | 0.07 |
| 79 | 0.05 | 80 | 0.81 |
| 81 | 0.67 | 82 | 1.02 |
| 83 | 0.73 | 84 | 0.72 |
| 85 | 1.23 | 86 | 4.60 |
| 87 | 5.88 | 88 | 0.20 |
| 89 | 0.41 | 90 | 0.17 |
| 91 | 0.14 | 92 | 1.85 |
| 93 | 0.61 | 94 | 1.74 |
| 95 | 0.71 | 96 | 0.08 |
| 97 | 4.62 | 98 | 0.16 |
| 99 | 0.06 | 100 | 9.42 |
| 101 | 2.38 | 102 | 0.47 |
| 103 | 1.76 | 104 | 0.72 |
| 105 | 0.41 | 106 | 4.00 |
| 107 | 0.31 | 108 | 1.64 |
| 109 | 1.86 | 110 | 3.01 |
| 111 | 0.34 | | |

The compounds tested above exhibit IC$_{50}$ values significantly less than 10 μM, with the most potent compounds showing antagonist activity at the prokineticin receptor with IC$_{50}$ values <1 μM. Accordingly, the compounds of the invention are expected to be useful in the prevention or treatment of conditions in which prokineticin receptor modulation is implicated.

In addition, the compounds of the present invention possess variously advantageous pharmacological and/or toxicological profiles, when tested in a variety of standard tests for such parameters. For example, the compounds of the invention exhibit one or more potentially useful properties for in vivo use, when characterised by pharmacological and/or toxicological tests including: hERG interaction (which is an indication of potential cardiotoxicity, and measures the effects of the compounds on the human ether-a-go-go-related gene, using for example the PatchXpress 7000A platform); CypP450 interactions (which may be measured in accordance with the FDA draft guidelines for drug interaction studies (study design, data analysis and implications for dosing and labeling) (September 2006), see www.fda.gov); phototoxicity (for example using a protocol in accordance with assay details outlined in the OECD guidelines for testing of chemicals: 432 In Vitro 3T3 Neutral Red Uptake phototoxicity test, April 2004); determination of pharmacokinetic parameters (for example following in vivo dosing via multiple routes, with plasma concentrations of compounds being determined from venous blood samples using an LC-MS/MS protocol); and in vivo receptor occupancy (determined, for example, using protocols based on Medhurst et al., *Journal of Pharmacology and Experimental Therapeutics*, 2007, 321, 1032). These standard tests for the characterisation of drug molecules are well known to the skilled person.

The invention claimed is:

1. A method for the treatment of inflammatory pain comprising administering to a patient in need thereof a therapeutically effective amount of a compound selected from the group consisting of:
   4-(3,4-Dichlorophenoxy)-1-((1,3,5-trimethyl-1H-pyrazol-4-yl)sulfonyl)piperidine,
   4-(3,4-Dichlorophenoxy)-1-[(3,5-dimethyl-1H-pyrazol-4-yl)sulfonyl]piperidine,
   4-[4-(Trifluoromethoxy)phenoxy]-1-[(1,3,5-trimethyl-1H-pyrazol-4-yl)sulfonyl]piperidine,
   4-(4-Methylphenoxy)-1-[(1,3,5-trimethyl-1H-pyrazol-4-yl)sulfonyl]piperidine,
   4-(4-Chlorophenoxy)-1-[(1,3,5-trimethyl-1H-pyrazol-4-yl)sulfonyl]piperidine,
   4-(3-Chlorophenoxy)-1-[(1,3,5-trimethyl-1H-pyrazol-4-yl)sulfonyl]piperidine,
   4-({1-[(1,3,5-Trimethyl-1H-pyrazol-4-yl)sulfonyl]piperidin-4-yl}oxy)benzonitrile,
   4-(4-Chlorophenoxy)-1-[(3,5-dimethyl-1H-pyrazol-4-yl)sulfonyl]piperidine,
   1-[(1-Ethyl-3,5-dimethyl-1H-pyrazol-4-yl)sulfonyl]-4-(4-methylphenoxy)piperidine,
   1-{[1,5-Dimethyl-3-(trifluoromethyl)-1H-pyrazol-4-yl]sulfonyl}-4-(4-methylphenoxy)piperidine,
   1-[(5-Chloro-1,3-dimethyl-1H-pyrazol-4-yl)sulfonyl]-4-(4-methylphenoxy)piperidine,
   4-[4-(Trifluoromethyl)phenoxy]-1-[(1,3,5-trimethyl-1H-pyrazol-4-yl)sulfonyl]piperidine,
   4-(2,4-Dichlorophenoxy)-1-[(1,3,5-trimethyl-1H-pyrazol-4-yl)sulfonyl]piperidine,
   4-(4-Bromo-2-fluorophenoxy)-1-[(1,3,5-trimethyl-1H-pyrazol-4-yl)sulfonyl]piperidine,
   1-[(5-Chloro-1,3-dimethyl-1H-pyrazol-4-yl)sulfonyl]-4-(4-chlorophenoxy)piperidine,
   4-(4-Chlorophenoxy)-1-{[1,5-dimethyl-3-(trifluoromethyl)-1H-pyrazol-4-yl]sulfonyl}piperidine,
   4-(3-Methoxyphenoxy)-1-[(1,3,5-trimethyl-1H-pyrazol-4-yl)sulfonyl]piperidine,
   4-(4-Methoxyphenoxy)-1-[(1,3,5-trimethyl-1H-pyrazol-4-yl)sulfonyl]piperidine,
   4-(4-Fluorophenoxy)-1-[(1,3,5-trimethyl-1H-pyrazol-4-yl)sulfonyl]piperidine,
   4-(4-Chlorophenoxy)-3-methyl-1-[(1,3,5-trimethyl-1H-pyrazol-4-yl)sulfonyl]piperidine,
   4-(2,4-Dichlorophenoxy)-1-[(3,5-dimethyl-1H-pyrazol-4-yl)sulfonyl]piperidine,
   4-(4-Chlorophenoxy)-2-methyl-1-[(1,3,5-trimethyl-1H-pyrazol-4-yl)sulfonyl]piperidine,
   1-[(5-Chloro-1,3-dimethyl-1H-pyrazol-4-yl)sulfonyl]-4-(2,4-dichlorophenoxy)piperidine,
   4-(2,4-Dichlorophenoxy)-1-{[1,3-dimethyl-5-(trifluoromethyl)-1H-pyrazol-4-yl]sulfonyl}piperidine,
   4-(2,4-Dichlorophenoxy)-1-[(1,3-dimethyl-1H-pyrazol-4-yl)sulfonyl]piperidine,
   4-(2,4-Dichlorophenoxy)-1-[(3,5-diethyl-1-methyl-1H-pyrazol-4-yl)sulfonyl]piperidine,
   4-(2,4-Dichlorophenoxy)-1-{[1-(difluoromethyl)-3,5-dimethyl-1H-pyrazol-4-yl]sulfonyl}piperidine,
   4-(4-Chloro-2-fluorophenoxy)-1-(trimethyl-1H-pyrazole-4-sulfonyl)piperidine,
   5-Chloro-2-{[1-(trimethyl-1H-pyrazole-4-sulfonyl)piperidin-4-yl]oxy}benzonitrile,
   1-[(3,5-Dimethyl-1H-pyrazol-4-yl)sulfonyl]-4-[4-(trifluoromethoxy)phenoxy]piperidine,
   5-Chloro-2-{[1-(3,5-dimethyl-1H-pyrazole-4-sulfonyl)piperidin-4-yl]oxy}benzonitrile,
   4-(4-Chloro-2-fluorophenoxy)-1-(3,5-dimethyl-1H-pyrazole-4-sulfonyl)piperidine,
   4-(2,4-Dichlorophenoxy)-1-(1,4-dimethyl-1H-pyrazole-5-sulfonyl)piperidine,
   4-(4-Chlorophenoxy)-1-(1,4-dimethyl-1H-pyrazole-5-sulfonyl)piperidine,
   1-(3,5-Dimethyl-1H-pyrazole-4-sulfonyl)-4-(2,6-dimethylphenoxy)piperidine,
   4-[4-Chloro-2-(trifluoromethyl)phenoxy]-1-(trimethyl-1H-pyrazole-4-sulfonyl)piperidine,
   4-[4-Chloro-2-(trifluoromethyl)phenoxy]-1-(3,5-dimethyl-1H-pyrazole-4-sulfonyl)piperidine,
   1-(3,5-Dimethyl-1H-pyrazole-4-sulfonyl)-4-(3-fluoro-4-methoxyphenoxy)piperidine,
   4-(3,5-Difluoro-4-methoxyphenoxy)-1-(3,5-dimethyl-1H-pyrazole-4-sulfonyl)piperidine,
   4-(3-Fluoro-4-methoxyphenoxy)-1-(trimethyl-1H-pyrazole-4-sulfonyl)piperidine,
   4-(3,5-Difluoro-4-methoxyphenoxy)-1-(trimethyl-1H-pyrazole-4-sulfonyl)piperidine,
   4-(4-Chloro-3-fluorophenoxy)-1-(trimethyl-1H-pyrazole-4-sulfonyl)piperidine,
   4-(4-Chloro-2,6-difluorophenoxy)-1-(trimethyl-1H-pyrazole-4-sulfonyl)piperidine,
   4-(4-Chloro-3-fluorophenoxy)-1-(3,5-dimethyl-1H-pyrazole-4-sulfonyl)piperidine,
   5-Chloro-2-((1-((1,3,5-trimethyl-1H-pyrazol-4-yl)sulfonyl)piperidin-4-yl)oxy)pyridine,
   N-(4-Chlorophenyl)-1-((1,3,5-trimethyl-1H-pyrazol-4-yl)sulfonyl)piperidin-4-amine,
   N-(3,4-Dichlorophenyl)-1-((1,3,5-trimethyl-1H-pyrazol-4-yl)sulfonyl)piperidin-4-amine,
   4-Chloro-N-{[1-(trimethyl-1H-pyrazole-4-sulfonyl)piperidin-4-yl]methyl}aniline,
   3,4-Dichloro-N-{[1-(trimethyl-1H-pyrazole-4-sulfonyl)piperidin-4-yl]methyl}aniline,
   4-(4-Chlorobenzyl)-1-((1,3,5-trimethyl-1H-pyrazol-4-yl)sulfonyl)piperidine,
   4-(3,4-Dichlorobenzyl)-1-((1,3,5-trimethyl-1H-pyrazol-4-yl)sulfonyl)piperidine,
   4-(4-Chlorobenzyl)-1-((1,3,5-trimethyl-1H-pyrazol-4-yl)sulfonyl)piperidin-4-ol,
   4-(4-Chlorobenzyl)-4-methoxy-1-((1,3,5-trimethyl-1H-pyrazol-4-yl)sulfonyl)piperidine, 4-(2,4-Dichlorobenzyl)-1-((1,3,5-trimethyl-1H-pyrazol-4-yl)sulfonyl)piperidin-4-ol,
4-(4-Chlorobenzyl)-4-(methoxymethyl)-1-((1,3,5-trimethyl-1H-pyrazol-4-yl)sulfonyl)piperidine,
Ethyl 4-(4-chlorobenzyl)-1-((1,3,5-trimethyl-1H-pyrazol-4-yl)sulfonyl)piperidine-4-carboxylate,
Ethyl 4-(4-bromobenzyl)-1-((3,5-dimethyl-1H-pyrazol-4-yl)sulfonyl)piperidine-4-carboxylate,
Ethyl 4-(4-bromobenzyl)-1-((1,3,5-trimethyl-1H-pyrazol-4-yl)sulfonyl)piperidine-4-carboxylate,
4-(4-Chlorobenzyl)-1-((3,5-dimethyl-1H-pyrazol-4-yl)sulfonyl)piperidine-4-carbonitrile,
4-(2,4-Dichlorobenzyl)-1-((3,5-dimethyl-1H-pyrazol-4-yl)sulfonyl)piperidine-4-carbonitrile,
1-((5-Chloro-1,3-dimethyl-1H-pyrazol-4-yl)sulfonyl)-4-(4 chlorobenzyl)piperidine,
4-(3,4-Dichlorobenzyl)-1-((1,3,5-trimethyl-1H-pyrazol-4-yl)sulfonyl)piperidin-4-ol,
4-(3,4-Dichlorobenzyl)-1-((3,5-dimethyl-1H-pyrazol-4-yl)sulfonyl)piperidin-4-ol,
4-(4-Chloro-3-fluorobenzyl)-1-((1,3,5-trimethyl-1H-pyrazol-4-yl)sulfonyl)piperidine,
4-(4-Chloro-2-methoxyphenoxy)-1-((3,5-dimethyl-1H-pyrazol-4-yl)sulfonyl)piperidine,
4-(4-Chloro-2-methoxyphenoxy)-1-((1,3,5-trimethyl-1H-pyrazol-4-yl)sulfonyl)piperidine,
4-(4-Chloro-2-fluorobenzyl)-1-((3,5-dimethyl-1H-pyrazol-4-yl)sulfonyl)piperidin-4-ol,
1-((3,5-Dimethyl-1H-pyrazol-4-yl)sulfonyl)-4-(2-fluorophenoxy)piperidine,
5-Chloro-3-fluoro-2-((1-((1,3,5-trimethyl-1H-pyrazol-4-yl)sulfonyl)piperidin-4-yl)oxy)pyridine,
4-(4-Chloro-2-methoxybenzyl)-1-((1,3,5-trimethyl-1H-pyrazol-4-yl)sulfonyl)piperidine,
4-(4-Chloro-2-fluorobenzyl)-1-((3,5-dimethyl-1H-pyrazol-4-yl)sulfonyl)-4-fluoropiperidine,
4-(4-Chloro-2-fluorobenzyl)-4-fluoro-1-((1,3,5-trimethyl-1H-pyrazol-4-yl)sulfonyl)piperidine,
4-(4-Chloro-2-fluorobenzyl)-1-((1,3,5-trimethyl-1H-pyrazol-4-yl)sulfonyl)piperidine,
5-Chloro-3-methoxy-2-((1-((1,3,5-trimethyl-1H-pyrazol-4-yl)sulfonyl)piperidin-4-yl)oxy)pyridine,
5-Chloro-2-((1-((3,5-dimethyl-1H-pyrazol-4-yl)sulfonyl)piperidin-4-yl)oxy)-3-methoxypyridine,
4-(4-Chloro-2-methoxybenzyl)-1-((3,5-dimethyl-1H-pyrazol-4-yl)sulfonyl)-4-methoxypiperidine,
4-(4-Chloro-2-methoxybenzyl)-4-methoxy-1-((1,3,5-trimethyl-1H-pyrazol-4-yl)sulfonyl)piperidine,
4-(4-Chloro-2-methoxybenzyl)-1-((1,3,5-trimethyl-1H-pyrazol-4-yl)sulfonyl)piperidin-4-ol,
4-(4-Chloro-2-methoxybenzyl)-1-((3,5-dimethyl-1H-pyrazol-4-yl)sulfonyl)piperidin-4-ol,
4-(4-Chloro-2-methoxybenzyl)-1-((3,5-dimethyl-1H-pyrazol-4-yl)sulfonyl)-4-fluoropiperidine,
4-(4-Chloro-2-methoxybenzyl)-4-fluoro-1-((1,3,5-trimethyl-1H-pyrazol-4-yl)sulfonyl)piperidine,
2-(4-Chloro-2-fluorophenyl)-2-(1-((3,5-dimethyl-1H-pyrazol-4-yl)sulfonyl)piperidin-4-yl)acetonitrile,
2-(4-Chlorophenyl)-2-(1-((3,5-dimethyl-1H-pyrazol-4-yl)sulfonyl)piperidin-4-yl)acetonitrile,
(4-Chlorophenyl)(1-((3,5-dimethyl-1H-pyrazol-4-yl)sulfonyl)piperidin-4-yl)methanol,
(4-Chlorophenyl)(1-((1,3,5-trimethyl-1H-pyrazol-4-yl)sulfonyl)piperidin-4-yl)methanol,
4-((4-Chlorophenyl)(methoxy)methyl)-1-((3,5-dimethyl-1H-pyrazol-4-yl)sulfonyl)piperidine,
4-((4-Chlorophenyl)(methoxy)methyl)-1-((1,3,5-trimethyl-1H-pyrazol-4-yl)sulfonyl)piperidine,
2-(4-Chlorophenyl)-2-(1-((3,5-dimethyl-1H-pyrazol-4-yl)sulfonyl)piperidin-4-yl)ethanol,
1-(4-Chlorophenyl)-1-(1-((3,5-dimethyl-1H-pyrazol-4-yl)sulfonyl)piperidin-4-yl)ethanol,
4-(1-(4-Chlorophenyl)ethyl)-1-((3,5-dimethyl-1H-pyrazol-4-yl)sulfonyl)piperidine,
4-((4-Chlorophenyl)(ethoxy)methyl)-1-((3,5-dimethyl-1H-pyrazol-4-yl)sulfonyl)piperidine,
4-(4-Chlorobenzyl)-1-((3,5-dimethyl-1H-pyrazol-4-yl)sulfonyl)piperidin-4-ol,
4-(1-(4-Chlorophenyl)-2-methoxyethyl)-1-((3,5-dimethyl-1H-pyrazol-4-yl)sulfonyl)piperidine,
4-(1-(4-Chlorophenyl)-2,2-difluoroethyl)-1-((3,5-dimethyl-1H-pyrazol-4-yl)sulfonyl)piperidine, and pharmaceutically acceptable salts of any one thereof.

* * * * *